(12) United States Patent
Muhsin et al.

(10) Patent No.: US 10,307,111 B2
(45) Date of Patent: Jun. 4, 2019

(54) PATIENT POSITION DETECTION SYSTEM

(71) Applicant: Masimo Corporation, Irvine, CA (US)

(72) Inventors: Bilal Muhsin, San Clemente, CA (US); Peter Scott Housel, Irvine, CA (US); Atiyeh Ghoreyshi, Foster City, CA (US); Ammar Al-Ali, San Juan Capistrano, CA (US); Massi Joe E. Kiani, Laguna Niguel, CA (US)

(73) Assignee: MASIMO CORPORATION, Irvine, CA (US)

( * ) Notice: Subject to any disclaimer, the term of this patent is extended or adjusted under 35 U.S.C. 154(b) by 0 days.

(21) Appl. No.: 14/511,974

(22) Filed: Oct. 10, 2014

(65) Prior Publication Data
US 2015/0112151 A1    Apr. 23, 2015

Related U.S. Application Data

(63) Continuation-in-part of application No. 13/762,270, filed on Feb. 7, 2013, now Pat. No. 10,149,616.
(Continued)

(51) Int. Cl.
*A61B 5/00* (2006.01)
*A61B 5/0205* (2006.01)
(Continued)

(52) U.S. Cl.
CPC .............. *A61B 5/746* (2013.01); *A61B 5/002* (2013.01); *A61B 5/0013* (2013.01);
(Continued)

(58) Field of Classification Search
CPC ..... A61B 5/746; A61B 5/0024; A61B 5/0077; A61B 5/015; A61B 5/1115; A61B 5/1117; A61B 5/1121
See application file for complete search history.

(56) References Cited

U.S. PATENT DOCUMENTS 3,646,606 A   2/1972   Buxton et al.
3,690,313 A   9/1972   Weber et al.
(Continued)

FOREIGN PATENT DOCUMENTS

EP        735499 A1     10/1996
EP    2 335 569 A2      6/2011
(Continued)

OTHER PUBLICATIONS

US 8,845,543 B2, 09/2014, Diab et al. (withdrawn)
(Continued)

*Primary Examiner* — Timothy J Neal
*Assistant Examiner* — Jae Woo
(74) *Attorney, Agent, or Firm* — Knobbe Martens Olson & Bear LLP

(57) ABSTRACT

A patient movement detector can receive inputs from position sensors, a thermal imaging camera, a video camera, and/or triangulation data. Based on one or more of these inputs, the patient movement detector can perform one or more of the following: fall prevention detection, bedsore prevention analysis, patient location detection, and patient walk test scoring. The patient movement detector can, for example, output a fall warning alarm, a bedsore warning alarm, patient location information, and walk test scores.

3 Claims, 39 Drawing Sheets

Related U.S. Application Data

(60) Provisional application No. 61/889,939, filed on Oct. 11, 2013, provisional application No. 61/703,713, filed on Sep. 20, 2012, provisional application No. 61/625,584, filed on Apr. 17, 2012, provisional application No. 61/597,126, filed on Feb. 9, 2012.

(51) Int. Cl.
*A61B 5/01* (2006.01)
*A61B 5/11* (2006.01)
*A61B 5/024* (2006.01)
*A61B 5/1455* (2006.01)

(52) U.S. Cl.
CPC .......... *A61B 5/0024* (2013.01); *A61B 5/0077* (2013.01); *A61B 5/015* (2013.01); *A61B 5/02055* (2013.01); *A61B 5/02416* (2013.01); *A61B 5/1115* (2013.01); *A61B 5/1121* (2013.01); *A61B 5/1128* (2013.01); *A61B 5/14551* (2013.01); *A61B 5/7282* (2013.01); *A61B 5/1117* (2013.01); *A61B 5/447* (2013.01); *A61B 5/7246* (2013.01); *A61B 5/7275* (2013.01); *A61B 2560/0266* (2013.01); *A61B 2560/0475* (2013.01)

(56) References Cited

U.S. PATENT DOCUMENTS

| | | |
|---|---|---|
| 3,978,849 A | 9/1976 | Geneen |
| 4,108,166 A | 8/1978 | Schmid |
| 4,129,125 A | 12/1978 | Lester et al. |
| 4,231,354 A | 11/1980 | Kurtz et al. |
| 4,589,415 A | 5/1986 | Haaga |
| 4,662,378 A | 5/1987 | Thomis |
| 4,838,275 A | 6/1989 | Lee |
| 4,852,570 A | 8/1989 | Levine |
| 4,960,128 A | 10/1990 | Gordon et al. |
| 4,964,408 A | 10/1990 | Hink et al. |
| 4,966,154 A | 10/1990 | Cooper et al. |
| 5,041,187 A | 8/1991 | Hink et al. |
| 5,069,213 A | 12/1991 | Polczynski |
| 5,092,340 A | 3/1992 | Yamaguchi et al. |
| 5,140,519 A | 8/1992 | Friesdorf et al. |
| 5,159,932 A | 11/1992 | Zanetti et al. |
| 5,161,539 A | 11/1992 | Evans et al. |
| 5,163,438 A | 11/1992 | Gordon et al. |
| 5,262,944 A | 11/1993 | Weisner et al. |
| 5,277,189 A | 1/1994 | Jacobs |
| 5,278,627 A | 1/1994 | Aoyagi et al. |
| 5,282,474 A | 2/1994 | Valdes Sosa et al. |
| 5,296,688 A | 3/1994 | Hamilton et al. |
| 5,318,037 A | 6/1994 | Evans et al. |
| 5,319,355 A | 6/1994 | Russek |
| 5,331,549 A | 7/1994 | Crawford, Jr. |
| 5,333,106 A | 7/1994 | Lanpher et al. |
| 5,337,744 A | 8/1994 | Branigan |
| 5,341,805 A | 8/1994 | Stavridi et al. |
| 5,348,008 A | 9/1994 | Bornn et al. |
| 5,358,519 A | 10/1994 | Grandjean |
| D353,195 S | 12/1994 | Savage et al. |
| D353,196 S | 12/1994 | Savage et al. |
| 5,375,599 A | 12/1994 | Schimizu |
| 5,377,676 A | 1/1995 | Vari et al. |
| 5,400,794 A | 3/1995 | Gorman |
| 5,416,695 A | 5/1995 | Stutman et al. |
| D359,546 S | 6/1995 | Savage et al. |
| 5,431,170 A | 7/1995 | Mathews |
| 5,434,611 A | 7/1995 | Tamura |
| D361,840 S | 8/1995 | Savage et al. |
| D362,063 S | 9/1995 | Savage et al. |
| 5,452,717 A | 9/1995 | Branigan et al. |
| D363,120 S | 10/1995 | Savage et al. |
| 5,456,252 A | 10/1995 | Vari et al. |
| 5,479,934 A | 1/1996 | Imran |
| 5,482,036 A | 1/1996 | Diab et al. |
| 5,483,968 A | 1/1996 | Adam et al. |
| 5,490,505 A | 2/1996 | Diab et al. |
| 5,494,041 A | 2/1996 | Wilk |
| 5,494,043 A | 2/1996 | O'Sullivan et al. |
| 5,503,149 A | 4/1996 | Beavin |
| 5,505,202 A | 4/1996 | Mogi et al. |
| 5,533,511 A | 7/1996 | Kaspari et al. |
| 5,534,851 A | 7/1996 | Russek |
| 5,544,649 A | 8/1996 | David et al. |
| 5,553,609 A | 9/1996 | Chen et al. |
| 5,558,638 A | 9/1996 | Evers et al. |
| 5,561,275 A | 10/1996 | Savage et al. |
| 5,562,002 A | 10/1996 | Lalin |
| 5,566,676 A | 10/1996 | Rosenfeldt et al. |
| 5,566,678 A | 10/1996 | Rosenfeldt et al. |
| 5,576,952 A | 11/1996 | Stutman et al. |
| 5,579,001 A | 11/1996 | Dempsey et al. |
| 5,590,649 A | 1/1997 | Caro et al. |
| 5,602,924 A | 2/1997 | Durand et al. |
| 5,619,991 A | 4/1997 | Sloane |
| 5,632,272 A | 5/1997 | Diab et al. |
| 5,638,816 A | 6/1997 | Kiani-Azarbayjany et al. |
| 5,638,818 A | 6/1997 | Diab et al. |
| 5,640,967 A | 6/1997 | Fine et al. |
| 5,645,440 A | 7/1997 | Tobler et al. |
| 5,685,299 A | 11/1997 | Diab et al. |
| 5,685,314 A | 11/1997 | Geheb et al. |
| 5,687,717 A | 11/1997 | Halpern et al. |
| 5,694,020 A | 12/1997 | Lang |
| 5,724,580 A | 3/1998 | Levin et al. |
| 5,724,983 A | 3/1998 | Selker et al. |
| 5,725,308 A | 3/1998 | Smith et al. |
| 5,734,739 A | 3/1998 | Sheehan et al. |
| D393,830 S | 4/1998 | Tobler et al. |
| 5,743,262 A | 4/1998 | Lepper, Jr. et al. |
| 5,758,079 A | 5/1998 | Ludwig et al. |
| 5,758,644 A | 6/1998 | Diab et al. |
| 5,760,910 A | 6/1998 | Lepper, Jr. et al. |
| 5,769,785 A | 6/1998 | Diab et al. |
| 5,772,585 A | 6/1998 | Lavin et al. |
| 5,782,757 A | 7/1998 | Diab et al. |
| 5,782,805 A | 7/1998 | Meinzer |
| 5,785,659 A | 7/1998 | Caro et al. |
| 5,791,347 A | 8/1998 | Flaherty et al. |
| 5,801,637 A | 9/1998 | Lomholt |
| 5,810,734 A | 9/1998 | Caro et al. |
| 5,822,544 A | 10/1998 | Chaco et al. |
| 5,822,546 A | 10/1998 | George |
| 5,823,950 A | 10/1998 | Diab et al. |
| 5,830,131 A | 11/1998 | Caro et al. |
| 5,833,618 A | 11/1998 | Caro et al. |
| 5,855,550 A | 1/1999 | Lai et al. |
| 5,860,919 A | 1/1999 | Kiani-Azarbayjany et al. |
| 5,890,929 A | 4/1999 | Mills et al. |
| 5,904,654 A | 5/1999 | Wohltmann et al. |
| 5,910,139 A | 6/1999 | Cochran et al. |
| 5,919,134 A | 7/1999 | Diab |
| 5,921,920 A | 7/1999 | Marshall et al. |
| 5,924,074 A | 7/1999 | Evans |
| 5,931,160 A | 8/1999 | Gilmore et al. |
| 5,934,925 A | 8/1999 | Tobler et al. |
| 5,940,182 A | 8/1999 | Lepper, Jr. et al. |
| 5,941,836 A | 8/1999 | Friedman |
| 5,942,986 A | 8/1999 | Shabot et al. |
| 5,987,519 A | 11/1999 | Peifer et al. |
| 5,995,855 A | 11/1999 | Kiani et al. |
| 5,997,343 A | 12/1999 | Mills et al. |
| 6,002,952 A | 12/1999 | Diab et al. |
| 6,011,986 A | 1/2000 | Diab et al. |
| 6,014,346 A * | 1/2000 | Malone ............... A61B 5/1118 340/573.1 |
| 6,018,673 A | 1/2000 | Chin et al. |
| 6,024,699 A | 2/2000 | Surwit et al. |
| 6,027,452 A | 2/2000 | Flaherty et al. |
| 6,032,678 A | 3/2000 | Rottem |
| 6,035,230 A | 3/2000 | Kang |
| 6,036,642 A | 3/2000 | Diab et al. |

(56) References Cited

U.S. PATENT DOCUMENTS

| | | | |
|---|---|---|---|
| 6,045,509 A | 4/2000 | Caro et al. |
| 6,067,462 A | 5/2000 | Diab et al. |
| 6,081,735 A | 6/2000 | Diab et al. |
| 6,088,607 A | 7/2000 | Diab et al. |
| 6,093,146 A | 7/2000 | Filangeri |
| 6,101,478 A | 8/2000 | Brown |
| 6,106,463 A | 8/2000 | Wilk |
| 6,110,522 A | 8/2000 | Lepper, Jr. et al. |
| 6,124,597 A | 9/2000 | Shehada |
| 6,128,521 A | 10/2000 | Marro et al. |
| 6,129,675 A | 10/2000 | Jay |
| 6,129,686 A | 10/2000 | Friedman |
| 6,132,218 A | 10/2000 | Benja-Athon |
| 6,139,494 A | 10/2000 | Cairnes |
| 6,144,868 A | 11/2000 | Parker |
| 6,151,516 A | 11/2000 | Kiani-Azarbayjany et al. |
| 6,152,754 A | 11/2000 | Gerhardt et al. |
| 6,157,850 A | 12/2000 | Diab et al. |
| 6,165,005 A | 12/2000 | Mills et al. |
| 6,167,258 A | 12/2000 | Schmidt et al. |
| D437,058 S | 1/2001 | Gozani |
| 6,168,563 B1 | 1/2001 | Brown |
| 6,171,237 B1 | 1/2001 | Avitall et al. |
| 6,183,417 B1 | 2/2001 | Gehab et al. |
| 6,184,521 B1 | 2/2001 | Coffin, IV et al. |
| 6,185,448 B1 | 2/2001 | Borovsky |
| 6,195,576 B1 | 2/2001 | John |
| 6,206,830 B1 | 3/2001 | Diab et al. |
| 6,221,012 B1 | 4/2001 | Maschke et al. |
| 6,224,553 B1 | 5/2001 | Nevo |
| 6,229,856 B1 | 5/2001 | Diab et al. |
| 6,230,142 B1 | 5/2001 | Benigno et al. |
| 6,232,609 B1 | 5/2001 | Snyder et al. |
| 6,236,872 B1 | 5/2001 | Diab et al. |
| 6,241,683 B1 | 6/2001 | Macklem et al. |
| 6,253,097 B1 | 6/2001 | Aronow et al. |
| 6,256,523 B1 | 7/2001 | Diab et al. |
| 6,263,222 B1 | 7/2001 | Diab et al. |
| 6,267,723 B1 | 7/2001 | Matsumura et al. |
| 6,269,262 B1 | 7/2001 | Kandori et al. |
| 6,278,522 B1 | 8/2001 | Lepper, Jr. et al. |
| 6,280,213 B1 | 8/2001 | Tobler et al. |
| 6,285,896 B1 | 9/2001 | Tobler et al. |
| 6,301,493 B1 | 10/2001 | Marro et al. |
| 6,312,378 B1 | 11/2001 | Bardy |
| 6,317,627 B1 | 11/2001 | Ennen et al. |
| 6,321,100 B1 | 11/2001 | Parker |
| 6,322,502 B1 | 11/2001 | Schoenberg et al. |
| 6,325,761 B1 | 12/2001 | Jay |
| 6,329,139 B1 | 12/2001 | Nova et al. |
| 6,334,065 B1 | 12/2001 | Al-Ali et al. |
| 6,338,039 B1 | 1/2002 | Lonski et al. |
| 6,343,224 B1 | 1/2002 | Parker |
| 6,349,228 B1 | 2/2002 | Kiani et al. |
| 6,354,235 B1 | 3/2002 | Davies |
| 6,360,114 B1 | 3/2002 | Diab et al. |
| 6,364,834 B1 | 4/2002 | Reuss et al. |
| 6,368,283 B1 | 4/2002 | Xu et al. |
| 6,371,921 B1 | 4/2002 | Caro et al. |
| 6,377,829 B1 | 4/2002 | Al-Ali |
| 6,385,476 B1 | 5/2002 | Osadchy et al. |
| 6,385,589 B1 | 5/2002 | Trusheim et al. |
| 6,388,240 B2 | 5/2002 | Schulz et al. |
| 6,397,091 B2 | 5/2002 | Diab et al. |
| 6,430,437 B1 | 8/2002 | Marro |
| 6,430,525 B1 | 8/2002 | Weber et al. |
| 6,463,311 B1 | 10/2002 | Diab |
| 6,470,199 B1 | 10/2002 | Kopotic et al. |
| 6,470,893 B1 | 12/2002 | Boesen |
| 6,501,975 B2 | 12/2002 | Diab et al. |
| 6,505,059 B1 | 1/2003 | Kollias et al. |
| 6,515,273 B2 | 2/2003 | Al-Ali |
| 6,519,487 B1 | 2/2003 | Parker |
| 6,524,240 B1 | 2/2003 | Thede |
| 6,525,386 B1 | 2/2003 | Mills et al. |
| 6,526,300 B1 | 2/2003 | Kiani et al. |
| 6,541,756 B2 | 4/2003 | Schulz et al. |
| 6,542,764 B1 | 4/2003 | Al-Ali et al. |
| 6,544,174 B2 | 4/2003 | West et al. |
| 6,551,243 B2 | 4/2003 | Bocionek et al. |
| 6,580,086 B1 | 6/2003 | Schulz et al. |
| 6,582,393 B2 | 6/2003 | Sage, Jr. |
| 6,584,336 B1 | 6/2003 | Ali et al. |
| 6,595,316 B2 | 7/2003 | Cybulski et al. |
| 6,597,932 B2 | 7/2003 | Tian et al. |
| 6,597,933 B2 | 7/2003 | Kiani et al. |
| 6,606,511 B1 | 8/2003 | Ali et al. |
| 6,616,606 B1 | 9/2003 | Peterson et al. |
| 6,632,181 B2 | 10/2003 | Flaherty et al. |
| 6,639,668 B1 | 10/2003 | Trepagnier |
| 6,640,116 B2 | 10/2003 | Diab |
| 6,641,533 B2 | 11/2003 | Causey et al. |
| 6,643,530 B2 | 11/2003 | Diab et al. |
| 6,646,556 B1 * | 11/2003 | Smith .................. A61B 5/1115 340/573.1 |
| 6,650,917 B2 | 11/2003 | Diab et al. |
| 6,650,939 B2 | 11/2003 | Takpke, II et al. |
| 6,654,624 B2 | 11/2003 | Diab et al. |
| D483,872 S | 12/2003 | Cruz et al. |
| 6,658,276 B2 | 12/2003 | Diab et al. |
| 6,661,161 B1 | 12/2003 | Lanzo et al. |
| 6,671,531 B2 | 12/2003 | Al-Ali et al. |
| 6,678,543 B2 | 1/2004 | Diab et al. |
| 6,684,090 B2 | 1/2004 | Ali et al. |
| 6,684,091 B2 | 1/2004 | Parker |
| 6,694,180 B1 | 2/2004 | Boesen |
| 6,697,656 B1 | 2/2004 | Al-Ali |
| 6,697,657 B1 | 2/2004 | Shehada et al. |
| 6,697,658 B2 | 2/2004 | Al-Ali |
| RE38,476 E | 3/2004 | Diab et al. |
| 6,699,194 B1 | 3/2004 | Diab et al. |
| 6,714,804 B2 | 3/2004 | Al-Ali et al. |
| RE38,492 E | 4/2004 | Diab et al. |
| 6,719,694 B2 | 4/2004 | Weng et al. |
| 6,721,582 B2 | 4/2004 | Trepagnier et al. |
| 6,721,585 B1 | 4/2004 | Parker |
| 6,725,075 B2 | 4/2004 | Al-Ali |
| 6,728,560 B2 | 4/2004 | Kollias et al. |
| 6,735,459 B2 | 5/2004 | Parker |
| 6,745,060 B2 | 6/2004 | Diab et al. |
| 6,751,492 B2 | 6/2004 | Ben-haim |
| 6,760,607 B2 | 7/2004 | Al-Ali |
| 6,770,028 B1 | 8/2004 | Ali et al. |
| 6,771,994 B2 | 8/2004 | Kiani et al. |
| 6,783,492 B2 | 8/2004 | Dominguez |
| 6,790,178 B1 | 9/2004 | Mault et al. |
| 6,792,300 B1 | 9/2004 | Diab et al. |
| 6,795,724 B2 | 9/2004 | Hogan |
| 6,804,656 B1 | 10/2004 | Rosenfeld |
| 6,807,050 B1 | 10/2004 | Whitehorn et al. |
| 6,813,511 B2 | 11/2004 | Diab et al. |
| 6,816,741 B2 | 11/2004 | Diab |
| 6,817,979 B2 | 11/2004 | Nihtila et al. |
| 6,822,564 B2 | 11/2004 | Al-Ali |
| 6,826,419 B2 | 11/2004 | Diab et al. |
| 6,830,711 B2 | 12/2004 | Mills et al. |
| 6,837,848 B2 | 1/2005 | Bonner et al. |
| 6,841,535 B2 | 1/2005 | Divita et al. |
| 6,850,787 B2 | 2/2005 | Weber et al. |
| 6,850,788 B2 | 2/2005 | Al-Ali |
| 6,852,083 B2 | 2/2005 | Caro et al. |
| 6,855,112 B2 | 2/2005 | Kao et al. |
| 6,860,266 B2 | 3/2005 | Blike |
| 6,861,639 B2 | 3/2005 | Al-Ali |
| 6,897,788 B2 | 5/2005 | Khair et al. |
| 6,898,452 B2 | 5/2005 | Al-Ali et al. |
| 6,907,237 B2 | 6/2005 | Dorenbosch et al. |
| 6,915,149 B2 | 7/2005 | Ben-haim |
| 6,920,345 B2 | 7/2005 | Al-Ali et al. |
| 6,931,268 B1 | 8/2005 | Kiani-Azarbayjany et al. |
| 6,934,570 B2 | 8/2005 | Kiani et al. |
| 6,939,305 B2 | 9/2005 | Flaherty et al. |
| 6,943,348 B1 | 9/2005 | Coffin, IV |
| 6,950,687 B2 | 9/2005 | Al-Ali |

(56) References Cited

U.S. PATENT DOCUMENTS

| | | | |
|---|---|---|---|
| 6,952,340 B2 | 10/2005 | Son | |
| 6,961,598 B2 | 11/2005 | Diab | |
| 6,970,792 B1 | 11/2005 | Diab | |
| 6,979,812 B2 | 12/2005 | Al-Ali | |
| 6,980,419 B2 | 12/2005 | Smith et al. | |
| 6,983,179 B2 | 1/2006 | Ben-haim | |
| 6,985,764 B2 | 1/2006 | Mason et al. | |
| 6,988,989 B2 | 1/2006 | Weiner et al. | |
| 6,990,087 B2 | 1/2006 | Rao et al. | |
| 6,993,371 B2 | 1/2006 | Kiani et al. | |
| 6,996,427 B2 | 2/2006 | Ali et al. | |
| 6,997,884 B2 | 2/2006 | Ulmsten | |
| 6,999,904 B2 | 2/2006 | Weber et al. | |
| 7,003,338 B2 | 2/2006 | Weber et al. | |
| 7,003,339 B2 | 2/2006 | Diab et al. | |
| 7,004,907 B2 | 2/2006 | Banet et al. | |
| 7,015,451 B2 | 2/2006 | Dalke et al. | |
| 7,024,233 B2 | 4/2006 | Ali et al. | |
| 7,025,729 B2 | 4/2006 | De Chazal et al. | |
| 7,027,849 B2 | 4/2006 | Al-Ali | |
| 7,030,749 B2 | 4/2006 | Al-Ali | |
| 7,033,761 B2 | 4/2006 | Shafer | |
| 7,035,686 B2 | 4/2006 | Hogan | |
| 7,039,449 B2 | 5/2006 | Al-Ali | |
| 7,041,060 B2 | 5/2006 | Flaherty et al. | |
| 7,044,918 B2 | 5/2006 | Diab | |
| 7,063,666 B2 | 6/2006 | Weng et al. | |
| 7,067,893 B2 | 6/2006 | Mills et al. | |
| 7,079,035 B2 | 7/2006 | Bock et al. | |
| 7,096,052 B2 | 8/2006 | Mason et al. | |
| 7,096,054 B2 | 8/2006 | Abdul-Hafiz et al. | |
| 7,132,641 B2 | 11/2006 | Schulz et al. | |
| 7,142,901 B2 | 11/2006 | Kiani et al. | |
| 7,149,561 B2 | 12/2006 | Diab | |
| 7,179,228 B2 | 2/2007 | Banet | |
| 7,186,966 B2 | 3/2007 | Al-Ali | |
| 7,188,621 B2 | 3/2007 | DeVries et al. | |
| 7,190,261 B2 | 3/2007 | Al-Ali | |
| 7,208,119 B1 | 4/2007 | Kurtock et al. | |
| 7,215,984 B2 | 5/2007 | Diab | |
| 7,215,986 B2 | 5/2007 | Diab | |
| 7,221,971 B2 | 5/2007 | Diab | |
| 7,225,006 B2 | 5/2007 | Al-Ali et al. | |
| 7,225,007 B2 | 5/2007 | Al-Ali | |
| RE39,672 E | 6/2007 | Shehada et al. | |
| 7,229,415 B2 | 6/2007 | Schwartz | |
| 7,238,159 B2 | 7/2007 | Banet et al. | |
| 7,239,905 B2 | 7/2007 | Kiani-Azarbayjany et al. | |
| 7,241,287 B2 | 7/2007 | Shehada et al. | |
| 7,244,251 B2 | 7/2007 | Shehada et al. | |
| 7,245,953 B1 | 7/2007 | Parker | |
| 7,252,659 B2 | 8/2007 | Shehada et al. | |
| 7,254,429 B2 | 8/2007 | Schurman et al. | |
| 7,254,431 B2 | 8/2007 | Al-Ali | |
| 7,254,433 B2 | 8/2007 | Diab et al. | |
| 7,254,434 B2 | 8/2007 | Schulz et al. | |
| 7,256,708 B2 | 8/2007 | Rosenfeld | |
| 7,264,616 B2 | 9/2007 | Shehada et al. | |
| 7,267,671 B2 | 9/2007 | Shehada et al. | |
| 7,268,859 B2 | 9/2007 | Sage, Jr. et al. | |
| 7,272,425 B2 | 9/2007 | Al-Ali | |
| 7,274,955 B2 | 9/2007 | Kiani et al. | |
| D554,263 S | 10/2007 | Al-Ali | |
| 7,280,858 B2 | 10/2007 | Al-Ali et al. | |
| 7,285,090 B2 | 10/2007 | Stivoric | |
| 7,289,835 B2 | 10/2007 | Mansfield et al. | |
| 7,292,883 B2 | 11/2007 | De Felice et al. | |
| 7,295,866 B2 | 11/2007 | Al-Ali | |
| 7,307,543 B2 | 12/2007 | Rosenfeld | |
| 7,313,423 B2 | 12/2007 | Griffin et al. | |
| 7,314,446 B2 | 1/2008 | Byrd et al. | |
| 7,315,825 B2 | 1/2008 | Rosenfeld | |
| 7,321,862 B2 | 1/2008 | Rosenfeld | |
| 7,322,971 B2 | 1/2008 | Shehada et al. | |
| 7,328,053 B1 | 2/2008 | Diab et al. | |
| 7,332,784 B2 | 2/2008 | Mills et al. | |
| 7,336,187 B2 | 2/2008 | Hubbard, Jr. et al. | |
| 7,340,287 B2 | 3/2008 | Mason et al. | |
| 7,341,559 B2 | 3/2008 | Schulz et al. | |
| 7,343,186 B2 | 3/2008 | Lamego et al. | |
| D566,282 S | 4/2008 | Al-Ali et al. | |
| 7,355,512 B1 | 4/2008 | Al-Ali | |
| 7,356,178 B2 | 4/2008 | Ziel et al. | |
| 7,356,365 B2 | 4/2008 | Schurman | |
| 7,361,155 B2 | 4/2008 | Sage, Jr. et al. | |
| 7,371,981 B2 | 5/2008 | Abdul-Hafiz | |
| 7,373,193 B2 | 5/2008 | Al-Ali et al. | |
| 7,373,194 B2 | 5/2008 | Weber et al. | |
| 7,376,453 B1 | 5/2008 | Diab et al. | |
| 7,377,794 B2 | 5/2008 | Al Ali et al. | |
| 7,377,899 B2 | 5/2008 | Weber et al. | |
| 7,378,975 B1 * | 5/2008 | Smith | A61B 5/1126 340/573.1 |
| 7,382,247 B2 | 6/2008 | Welch et al. | |
| 7,383,070 B2 | 6/2008 | Diab et al. | |
| 7,395,216 B2 | 7/2008 | Rosenfeld | |
| 7,396,330 B2 | 7/2008 | Banet et al. | |
| 7,411,509 B2 | 8/2008 | Rosenfeld | |
| 7,413,546 B2 | 8/2008 | Agutter et al. | |
| 7,415,297 B2 | 8/2008 | Al-Ali et al. | |
| 7,419,483 B2 | 9/2008 | Shehada | |
| 7,428,432 B2 | 9/2008 | Ali et al. | |
| 7,433,827 B2 | 10/2008 | Rosenfeld | |
| 7,438,683 B2 | 10/2008 | Al-Ali et al. | |
| 7,439,856 B2 | 10/2008 | Weiner et al. | |
| 7,440,787 B2 | 10/2008 | Diab | |
| 7,454,240 B2 | 11/2008 | Diab et al. | |
| 7,454,359 B2 | 11/2008 | Rosenfeld | |
| 7,454,360 B2 | 11/2008 | Rosenfeld | |
| 7,462,151 B2 | 12/2008 | Childre et al. | |
| 7,467,002 B2 | 12/2008 | Weber et al. | |
| 7,467,094 B2 | 12/2008 | Rosenfeld | |
| 7,469,157 B2 | 12/2008 | Diab et al. | |
| 7,471,969 B2 | 12/2008 | Diab et al. | |
| 7,471,971 B2 | 12/2008 | Diab et al. | |
| 7,475,019 B2 | 1/2009 | Rosenfeld | |
| 7,481,772 B2 | 1/2009 | Banet | |
| 7,483,729 B2 | 1/2009 | Al-Ali et al. | |
| 7,483,730 B2 | 1/2009 | Diab et al. | |
| 7,489,250 B2 | 2/2009 | Bock et al. | |
| 7,489,958 B2 | 2/2009 | Diab et al. | |
| 7,496,391 B2 | 2/2009 | Diab et al. | |
| 7,496,393 B2 | 2/2009 | Diab et al. | |
| D587,657 S | 3/2009 | Al-Ali et al. | |
| 7,497,828 B1 | 3/2009 | Wilk et al. | |
| 7,499,741 B2 | 3/2009 | Diab et al. | |
| 7,499,835 B2 | 3/2009 | Weber et al. | |
| 7,500,950 B2 | 3/2009 | Al-Ali et al. | |
| 7,509,154 B2 | 3/2009 | Diab et al. | |
| 7,509,494 B2 | 3/2009 | Al-Ali | |
| 7,510,849 B2 | 3/2009 | Schurman et al. | |
| 7,526,328 B2 | 4/2009 | Diab et al. | |
| 7,530,942 B1 | 5/2009 | Diab | |
| 7,530,949 B2 | 5/2009 | Al Ali et al. | |
| 7,530,955 B2 | 5/2009 | Diab et al. | |
| 7,549,961 B1 | 6/2009 | Hwang | |
| 7,551,717 B2 | 6/2009 | Tome et al. | |
| 7,559,520 B2 | 7/2009 | Quijano et al. | |
| 7,563,110 B2 | 7/2009 | Al-Ali et al. | |
| 7,577,475 B2 | 8/2009 | Consentino et al. | |
| 7,588,558 B2 | 9/2009 | Sage, Jr. et al. | |
| 7,590,950 B2 | 9/2009 | Collins et al. | |
| 7,596,398 B2 | 9/2009 | Al-Ali et al. | |
| 7,597,665 B2 | 10/2009 | Wilk et al. | |
| 7,612,999 B2 | 11/2009 | Clark et al. | |
| 7,618,375 B2 | 11/2009 | Flaherty | |
| D606,659 S | 12/2009 | Kiani et al. | |
| 7,639,145 B2 | 12/2009 | Lawson et al. | |
| 7,647,083 B2 | 1/2010 | Al-Ali et al. | |
| 7,650,291 B2 | 1/2010 | Rosenfeld | |
| D609,193 S | 2/2010 | Al-Ali et al. | |
| 7,654,966 B2 | 2/2010 | Westinskow et al. | |
| 7,658,716 B2 | 2/2010 | Banet et al. | |
| 7,684,845 B2 | 3/2010 | Juan | |

(56) References Cited

U.S. PATENT DOCUMENTS

| | | |
|---|---|---|
| 7,689,437 B1 | 3/2010 | Teller et al. |
| RE41,236 E | 4/2010 | Seely |
| D614,305 S | 4/2010 | Al-Ali et al. |
| 7,693,697 B2 | 4/2010 | Westinskow et al. |
| RE41,317 E | 5/2010 | Parker |
| 7,729,733 B2 | 6/2010 | Al-Ali et al. |
| 7,734,320 B2 | 6/2010 | Al-Ali |
| 7,736,318 B2 | 6/2010 | Consentino et al. |
| 7,761,127 B2 | 7/2010 | Al-Ali et al. |
| 7,761,128 B2 | 7/2010 | Al-Ali et al. |
| 7,763,420 B2 | 7/2010 | Strizker et al. |
| 7,764,982 B2 | 7/2010 | Dalke et al. |
| D621,515 S | 8/2010 | Chua et al. |
| D621,516 S | 8/2010 | Kiani et al. |
| 7,766,818 B2 | 8/2010 | Iketani et al. |
| 7,774,060 B2 | 8/2010 | Westenskow et al. |
| 7,778,851 B2 | 8/2010 | Schoenberg et al. |
| 7,783,879 B2 | 8/2010 | Krummel et al. |
| 7,791,155 B2 | 9/2010 | Diab |
| 7,794,407 B2 | 9/2010 | Rothenberg |
| 7,801,581 B2 | 9/2010 | Diab |
| 7,803,120 B2 | 9/2010 | Banet et al. |
| 7,820,184 B2 | 10/2010 | Strizker et al. |
| 7,822,452 B2 | 10/2010 | Schurman et al. |
| RE41,912 E | 11/2010 | Parker |
| 7,831,450 B2 | 11/2010 | Schoenberg |
| 7,841,986 B2 | 11/2010 | He et al. |
| 7,844,313 B2 | 11/2010 | Kiani et al. |
| 7,844,314 B2 | 11/2010 | Al-Ali |
| 7,844,315 B2 | 11/2010 | Al-Ali |
| 7,848,935 B2 | 12/2010 | Gotlib |
| 7,858,322 B2 | 12/2010 | Tymianski et al. |
| 7,865,222 B2 | 1/2011 | Weber et al. |
| 7,865,232 B1 | 1/2011 | Krishnaswamy et al. |
| 7,873,497 B2 | 1/2011 | Weber et al. |
| 7,880,606 B2 | 2/2011 | Al-Ali |
| 7,880,626 B2 | 2/2011 | Al-Ali et al. |
| 7,890,156 B2 | 2/2011 | Ooi et al. |
| 7,891,355 B2 | 2/2011 | Al-Ali et al. |
| 7,894,868 B2 | 2/2011 | Al-Ali et al. |
| 7,899,507 B2 | 3/2011 | Al-Ali et al. |
| 7,899,518 B2 | 3/2011 | Trepagnier et al. |
| 7,904,132 B2 | 3/2011 | Weber et al. |
| 7,909,772 B2 | 3/2011 | Popov et al. |
| 7,910,875 B2 | 3/2011 | Al-Ali |
| 7,914,514 B2 | 3/2011 | Calderon |
| 7,919,713 B2 | 4/2011 | Al-Ali et al. |
| 7,937,128 B2 | 5/2011 | Al-Ali |
| 7,937,129 B2 | 5/2011 | Mason et al. |
| 7,937,130 B2 | 5/2011 | Diab et al. |
| 7,941,199 B2 | 5/2011 | Kiani |
| 7,951,086 B2 | 5/2011 | Flaherty et al. |
| 7,957,780 B2 | 6/2011 | Lamego et al. |
| 7,962,188 B2 | 6/2011 | Kiani et al. |
| 7,962,190 B1 | 6/2011 | Diab et al. |
| 7,963,927 B2 | 6/2011 | Kelleher et al. |
| 7,967,749 B2 | 6/2011 | Hutchinson et al. |
| 7,976,472 B2 | 7/2011 | Kiani |
| 7,988,637 B2 | 8/2011 | Diab |
| 7,988,639 B2 | 8/2011 | Starks |
| 7,990,382 B2 | 8/2011 | Kiani |
| 7,991,446 B2 | 8/2011 | Al-Ali et al. |
| 7,991,463 B2 | 8/2011 | Kelleher et al. |
| 7,991,625 B2 | 8/2011 | Rosenfeld |
| 7,993,275 B2 | 8/2011 | Banet et al. |
| 8,000,761 B2 | 8/2011 | Al-Ali |
| 8,008,088 B2 | 8/2011 | Bellott et al. |
| RE42,753 E | 9/2011 | Kiani-Azarbayjany et al. |
| 8,019,400 B2 | 9/2011 | Diab et al. |
| 8,027,846 B2 | 9/2011 | Schoenberg |
| 8,028,701 B2 | 10/2011 | Al-Ali et al. |
| 8,029,765 B2 | 10/2011 | Bellott et al. |
| 8,033,996 B2 | 10/2011 | Behar |
| 8,036,727 B2 | 10/2011 | Schurman et al. |
| 8,036,728 B2 | 10/2011 | Diab et al. |
| 8,036,736 B2 | 10/2011 | Snyder et al. |
| 8,038,625 B2 | 10/2011 | Afonso et al. |
| 8,046,040 B2 | 10/2011 | Ali et al. |
| 8,046,041 B2 | 10/2011 | Diab et al. |
| 8,046,042 B2 | 10/2011 | Diab et al. |
| 8,048,040 B2 | 11/2011 | Kiani |
| 8,050,728 B2 | 11/2011 | Al-Ali et al. |
| 8,068,104 B2 | 11/2011 | Rampersad |
| 8,073,707 B2 | 12/2011 | Teller et al. |
| 8,094,013 B1 | 1/2012 | Lee et al. |
| RE43,169 E | 2/2012 | Parker |
| 8,118,620 B2 | 2/2012 | Al-Ali et al. |
| 8,126,528 B2 | 2/2012 | Diab et al. |
| 8,128,572 B2 | 3/2012 | Diab et al. |
| 8,130,105 B2 | 3/2012 | Al-Ali et al. |
| 8,145,287 B2 | 3/2012 | Diab et al. |
| 8,150,487 B2 | 4/2012 | Diab et al. |
| D659,836 S | 5/2012 | Bensch et al. |
| 8,170,887 B2 | 5/2012 | Rosenfeld |
| 8,175,672 B2 | 5/2012 | Parker |
| 8,175,895 B2 | 5/2012 | Rosenfeld |
| 8,180,420 B2 | 5/2012 | Diab et al. |
| 8,180,440 B2 | 5/2012 | McCombie et al. |
| 8,182,443 B1 | 5/2012 | Kiani |
| 8,185,180 B2 | 5/2012 | Diab et al. |
| 8,190,223 B2 | 5/2012 | Al-ali et al. |
| 8,190,227 B2 | 5/2012 | Diab et al. |
| 8,200,321 B2 | 6/2012 | McCombie et al. |
| 8,203,438 B2 | 6/2012 | Kiani et al. |
| 8,203,704 B2 | 6/2012 | Merritt et al. |
| 8,204,566 B2 | 6/2012 | Schurman et al. |
| 8,206,312 B2 | 6/2012 | Farquhar |
| 8,219,172 B2 | 7/2012 | Schurman et al. |
| 8,224,411 B2 | 7/2012 | Al-Ali et al. |
| 8,228,181 B2 | 7/2012 | Al-Ali |
| 8,229,533 B2 | 7/2012 | Diab et al. |
| 8,233,955 B2 | 7/2012 | Al-Ali et al. |
| 8,235,907 B2 | 8/2012 | Wilk et al. |
| 8,239,010 B2 | 8/2012 | Banet et al. |
| 8,239,780 B2 | 8/2012 | Manetta et al. |
| 8,241,213 B2 | 8/2012 | Lynn et al. |
| 8,244,325 B2 | 8/2012 | Al-Ali et al. |
| 8,249,815 B2 | 8/2012 | Taylor |
| 8,255,026 B1 | 8/2012 | Al-Ali |
| 8,255,027 B2 | 8/2012 | Al-Ali et al. |
| 8,255,028 B2 | 8/2012 | Al-Ali et al. |
| 8,260,577 B2 | 9/2012 | Weber et al. |
| 8,265,723 B1 | 9/2012 | McHale et al. |
| 8,274,360 B2 | 9/2012 | Sampath et al. |
| 8,294,588 B2 | 10/2012 | Fisher et al. |
| 8,294,716 B2 | 10/2012 | William et al. |
| 8,301,217 B2 | 10/2012 | Al-Ali et al. |
| 8,306,596 B2 | 11/2012 | Schurman et al. |
| 8,310,336 B2 | 11/2012 | Muhsin et al. |
| 8,311,747 B2 | 11/2012 | Taylor |
| 8,311,748 B2 | 11/2012 | Taylor et al. |
| 8,315,683 B2 | 11/2012 | Al-Ali et al. |
| 8,315,812 B2 | 11/2012 | Taylor |
| 8,315,813 B2 | 11/2012 | Taylor et al. |
| 8,315,814 B2 | 11/2012 | Taylor et al. |
| 8,321,004 B2 | 11/2012 | Moon et al. |
| 8,321,150 B2 | 11/2012 | Taylor |
| RE43,860 E | 12/2012 | Parker |
| 8,326,649 B2 | 12/2012 | Rosenfeld |
| 8,337,403 B2 | 12/2012 | Al-Ali et al. |
| 8,346,330 B2 | 1/2013 | Lamego |
| 8,353,842 B2 | 1/2013 | Al-Ali et al. |
| 8,355,766 B2 | 1/2013 | MacNeish, III et al. |
| 8,359,080 B2 | 1/2013 | Diab et al. |
| 8,360,936 B2 | 1/2013 | Dibenedetto et al. |
| 8,364,223 B2 | 1/2013 | Al-Ali et al. |
| 8,364,226 B2 | 1/2013 | Diab et al. |
| 8,364,250 B2 | 1/2013 | Moon et al. |
| 8,374,665 B2 | 2/2013 | Lamego |
| 8,385,995 B2 | 2/2013 | Al-ali et al. |
| 8,385,996 B2 | 2/2013 | Smith et al. |
| D679,018 S | 3/2013 | Fullerton et al. |
| 8,388,353 B2 | 3/2013 | Kiani et al. |
| 8,399,822 B2 | 3/2013 | Al-Ali |

(56) References Cited

U.S. PATENT DOCUMENTS

| | | |
|---|---|---|
| 8,401,602 B2 | 3/2013 | Kiani |
| 8,401,874 B2 | 3/2013 | Rosenfeld |
| 8,405,608 B2 | 3/2013 | Al-Ali et al. |
| 8,414,499 B2 | 4/2013 | Al-Ali et al. |
| 8,418,524 B2 | 4/2013 | Al-Ali |
| 8,419,649 B2 | 4/2013 | Banet et al. |
| 8,423,106 B2 | 4/2013 | Lamego et al. |
| 8,428,967 B2 | 4/2013 | Olsen et al. |
| 8,430,817 B1 | 4/2013 | Al-Ali et al. |
| 8,437,824 B2 | 5/2013 | Moon et al. |
| 8,437,825 B2 | 5/2013 | Dalvi et al. |
| 8,442,607 B2 | 5/2013 | Banet et al. |
| 8,449,469 B2 | 5/2013 | Banet et al. |
| 8,455,290 B2 | 6/2013 | Siskavich |
| 8,457,703 B2 | 6/2013 | Al-Ali |
| 8,457,707 B2 | 6/2013 | Kiani |
| 8,463,349 B2 | 6/2013 | Diab et al. |
| 8,466,286 B2 | 6/2013 | Bellot et al. |
| 8,471,713 B2 | 6/2013 | Poeze et al. |
| 8,473,020 B2 | 6/2013 | Kiani et al. |
| 8,475,370 B2 | 7/2013 | McCombie et al. |
| 8,483,787 B2 | 7/2013 | Al-Ali et al. |
| 8,489,364 B2 | 7/2013 | Weber et al. |
| 8,498,684 B2 | 7/2013 | Weber et al. |
| 8,504,128 B2 | 8/2013 | Blank et al. |
| 8,506,480 B2 | 8/2013 | Banet et al. |
| 8,509,867 B2 | 8/2013 | Workman et al. |
| 8,515,509 B2 | 8/2013 | Bruinsma et al. |
| 8,523,781 B2 | 9/2013 | Al-Ali |
| 8,527,038 B2 | 9/2013 | Moon et al. |
| 8,529,301 B2 | 9/2013 | Al-Ali et al. |
| 8,532,727 B2 | 9/2013 | Ali et al. |
| 8,532,728 B2 | 9/2013 | Diab et al. |
| D692,145 S | 10/2013 | Al-Ali et al. |
| 8,545,417 B2 | 10/2013 | Banet et al. |
| 8,547,209 B2 | 10/2013 | Kiani et al. |
| 8,548,548 B2 | 10/2013 | Al-Ali |
| 8,548,549 B2 | 10/2013 | Schurman et al. |
| 8,548,550 B2 | 10/2013 | Al-Ali et al. |
| 8,554,297 B2 | 10/2013 | Moon et al. |
| 8,560,032 B2 | 10/2013 | Al-Ali et al. |
| 8,560,034 B1 | 10/2013 | Diab et al. |
| 8,570,167 B2 | 10/2013 | Al-Ali |
| 8,570,503 B2 | 10/2013 | Vo et al. |
| 8,571,617 B2 | 10/2013 | Reichgott et al. |
| 8,571,618 B1 | 10/2013 | Lamego et al. |
| 8,571,619 B2 | 10/2013 | Al-Ali et al. |
| 8,584,345 B2 | 10/2013 | Al-Ali et al. |
| 8,574,161 B2 | 11/2013 | Banet et al. |
| 8,577,431 B2 | 11/2013 | Lamego et al. |
| 8,579,813 B2 | 11/2013 | Causey |
| 8,581,732 B2 | 11/2013 | Al-Ali et al. |
| 8,588,880 B2 | 11/2013 | Abdul-Hafiz et al. |
| 8,588,924 B2 | 11/2013 | Dion |
| 8,591,411 B2 | 11/2013 | Banet et al. |
| 8,594,776 B2 | 11/2013 | McCombie et al. |
| 8,600,467 B2 | 12/2013 | Al-Ali et al. |
| 8,600,777 B2 | 12/2013 | Schoenberg |
| 8,602,997 B2 | 12/2013 | Banet et al. |
| 8,606,342 B2 | 12/2013 | Diab |
| 8,620,678 B2 | 12/2013 | Gotlib |
| 8,622,922 B2 | 1/2014 | Banet et al. |
| 8,626,255 B2 | 1/2014 | Al-Ali et al. |
| 8,630,691 B2 | 1/2014 | Lamego et al. |
| 8,634,889 B2 | 1/2014 | Al-Ali et al. |
| 8,641,631 B2 | 2/2014 | Sierra et al. |
| 8,652,060 B2 | 2/2014 | Al-Ali |
| 8,663,107 B2 | 3/2014 | Kiani |
| 8,666,468 B1 | 3/2014 | Al-Ali |
| 8,667,967 B2 | 3/2014 | Al-Ali et al. |
| 8,670,811 B2 | 3/2014 | O'Reilly |
| 8,670,814 B2 | 3/2014 | Diab et al. |
| 8,672,854 B2 | 3/2014 | McCombie et al. |
| 8,676,286 B2 | 3/2014 | Weber et al. |
| 8,682,407 B2 | 3/2014 | Al-Ali |
| RE44,823 E | 4/2014 | Parker |
| RE44,875 E | 4/2014 | Kiani et al. |
| 8,690,799 B2 | 4/2014 | Telfort et al. |
| 8,700,112 B2 | 4/2014 | Kiani |
| 8,702,627 B2 | 4/2014 | Telfort et al. |
| 8,706,179 B2 | 4/2014 | Parker |
| 8,712,494 B1 | 4/2014 | MacNeish, III et al. |
| 8,715,206 B2 | 5/2014 | Telfort et al. |
| 8,718,735 B2 | 5/2014 | Lamego et al. |
| 8,718,737 B2 | 5/2014 | Diab et al. |
| 8,718,738 B2 | 5/2014 | Blank et al. |
| 8,720,249 B2 | 5/2014 | Al-Ali |
| 8,721,541 B2 | 5/2014 | Al-Ali et al. |
| 8,721,542 B2 | 5/2014 | Al-Ali et al. |
| 8,723,677 B1 | 5/2014 | Kiani |
| 8,727,977 B2 | 5/2014 | Banet et al. |
| 8,738,118 B2 | 5/2014 | Moon et al. |
| 8,740,792 B1 | 6/2014 | Kiani et al. |
| 8,740,802 B2 | 6/2014 | Banet et al. |
| 8,740,807 B2 | 6/2014 | Banet et al. |
| 8,747,330 B2 | 6/2014 | Banet et al. |
| 8,754,776 B2 | 6/2014 | Poeze et al. |
| 8,755,535 B2 | 6/2014 | Telfort et al. |
| 8,755,856 B2 | 6/2014 | Diab et al. |
| 8,755,872 B1 | 6/2014 | Marinow |
| 8,761,850 B2 | 6/2014 | Lamego |
| D709,846 S | 7/2014 | Oswaks |
| 8,764,671 B2 | 7/2014 | Kiani |
| 8,768,423 B2 | 7/2014 | Shakespeare et al. |
| 8,771,204 B2 | 7/2014 | Telfort et al. |
| 8,777,634 B2 | 7/2014 | Kiani et al. |
| 8,781,543 B2 | 7/2014 | Diab et al. |
| 8,781,544 B2 | 7/2014 | Al-Ali et al. |
| 8,781,549 B2 | 7/2014 | Al-Ali et al. |
| 8,788,003 B2 | 7/2014 | Schurman et al. |
| 8,790,268 B2 | 7/2014 | Al-Ali |
| 8,801,613 B2 | 8/2014 | Al-Ali et al. |
| 8,808,188 B2 | 8/2014 | Banet et al. |
| 8,821,397 B2 | 9/2014 | Al-Ali et al. |
| 8,821,415 B2 | 9/2014 | Al-Ali et al. |
| 8,830,449 B1 | 9/2014 | Lamego et al. |
| 8,831,700 B2 | 9/2014 | Schurman et al. |
| 8,840,549 B2 | 9/2014 | Al-Ali |
| 8,847,740 B2 | 9/2014 | Kiani et al. |
| 8,849,365 B2 | 9/2014 | Smith et al. |
| 8,852,094 B2 | 10/2014 | Al-Ali et al. |
| 8,852,994 B2 | 10/2014 | Wojtczuk et al. |
| 8,866,620 B2 * | 10/2014 | Amir ........................ 340/573.1 |
| 8,868,147 B2 | 10/2014 | Stippick et al. |
| 8,868,150 B2 | 10/2014 | Al-Ali et al. |
| 8,870,792 B2 | 10/2014 | Al-Ali et al. |
| 8,878,888 B2 | 11/2014 | Rosenfeld |
| 8,886,271 B2 | 11/2014 | Kiani et al. |
| 8,888,539 B2 | 11/2014 | Al-Ali et al. |
| 8,888,700 B2 | 11/2014 | Banet et al. |
| 8,888,708 B2 | 11/2014 | Diab et al. |
| 8,892,180 B2 | 11/2014 | Weber et al. |
| 8,897,847 B2 | 11/2014 | Al-Ali |
| 8,907,287 B2 * | 12/2014 | Vanderpohl .......... A61B 5/0077 250/349 |
| 8,909,310 B2 | 12/2014 | Lamego et al. |
| 8,909,330 B2 | 12/2014 | McCombie et al. |
| 8,911,377 B2 | 12/2014 | Al-Ali |
| 8,912,909 B2 | 12/2014 | Al-Ali et al. |
| 8,920,317 B2 | 12/2014 | Al-Ali et al. |
| 8,921,699 B2 | 12/2014 | Al-Ali et al. |
| 8,922,382 B2 | 12/2014 | Al-Ali et al. |
| 8,929,964 B2 | 1/2015 | Al-Ali et al. |
| 8,942,777 B2 | 1/2015 | Diab et al. |
| 8,948,834 B2 | 2/2015 | Diab et al. |
| 8,948,835 B2 | 2/2015 | Diab |
| 8,956,293 B2 | 2/2015 | McCombie et al. |
| 8,956,294 B2 | 2/2015 | McCombie et al. |
| 8,965,471 B2 | 2/2015 | Lamego |
| 8,979,765 B2 | 3/2015 | Banet et al. |
| 8,983,564 B2 | 3/2015 | Al-Ali |
| 8,989,831 B2 | 3/2015 | Al-Ali et al. |
| 8,996,085 B2 | 3/2015 | Kiani et al. |
| 8,998,809 B2 | 4/2015 | Kiani |

(56) References Cited

U.S. PATENT DOCUMENTS

| | | |
|---|---|---|
| 9,028,429 B2 | 5/2015 | Telfort et al. |
| 9,037,207 B2 | 5/2015 | Al-Ali et al. |
| 9,055,928 B2 | 6/2015 | McCombie et al. |
| 9,060,721 B2 | 6/2015 | Reichgott et al. |
| 9,066,666 B2 | 6/2015 | Kiani |
| 9,066,680 B1 | 6/2015 | Al-Ali et al. |
| 9,072,474 B2 | 7/2015 | Al-Ali et al. |
| 9,078,560 B2 | 7/2015 | Schurman et al. |
| 9,084,569 B2 | 7/2015 | Weber et al. |
| 9,095,316 B2 | 8/2015 | Welch et al. |
| 9,106,038 B2 | 8/2015 | Telfort et al. |
| 9,107,625 B2 | 8/2015 | Telfort et al. |
| 9,107,626 B2 | 8/2015 | Al-Ali et al. |
| 9,113,831 B2 | 8/2015 | Al-Ali |
| 9,113,832 B2 | 8/2015 | Al-Ali |
| 9,119,595 B2 | 9/2015 | Lamego |
| 9,131,881 B2 | 9/2015 | Diab et al. |
| 9,131,882 B2 | 9/2015 | Al-Ali et al. |
| 9,131,883 B2 | 9/2015 | Al-Ali |
| 9,131,917 B2 | 9/2015 | Telfort et al. |
| 9,138,180 B1 | 9/2015 | Coverston et al. |
| 9,138,182 B2 | 9/2015 | Al-Ali et al. |
| 9,138,192 B2 | 9/2015 | Weber et al. |
| 9,142,117 B2 | 9/2015 | Muhsin et al. |
| 9,149,192 B2 | 10/2015 | Banet et al. |
| 9,153,112 B1 | 10/2015 | Kiani et al. |
| 9,153,121 B2 | 10/2015 | Kiani et al. |
| 9,161,696 B2 | 10/2015 | Al-Ali et al. |
| 9,161,700 B2 | 10/2015 | Banet et al. |
| 9,161,713 B2 | 10/2015 | Al-Ali et al. |
| 9,167,995 B2 | 10/2015 | Lamego et al. |
| 9,173,593 B2 | 11/2015 | Banet et al. |
| 9,173,594 B2 | 11/2015 | Banet et al. |
| 9,176,141 B2 | 11/2015 | Al-Ali et al. |
| 9,186,102 B2 | 11/2015 | Bruinsma et al. |
| D745,167 S | 12/2015 | Canas et al. |
| 9,215,986 B2 | 12/2015 | Banet et al. |
| 9,307,915 B2 | 4/2016 | McCombie et al. |
| 9,339,209 B2 | 5/2016 | Banet et al. |
| 9,339,211 B2 | 5/2016 | Banet et al. |
| 9,364,158 B2 | 6/2016 | Banet et al. |
| 9,380,952 B2 | 7/2016 | Banet et al. |
| 9,408,573 B2 | 8/2016 | Welch et al. |
| 9,439,574 B2 | 9/2016 | McCombie et al. |
| 2001/0011355 A1 | 8/2001 | Kawai |
| 2001/0046366 A1 | 11/2001 | Susskind |
| 2002/0045836 A1 | 4/2002 | Alkawwas |
| 2002/0052311 A1 | 5/2002 | Solomon et al. |
| 2002/0063690 A1 | 5/2002 | Chung et al. |
| 2002/0140675 A1 | 10/2002 | Ali et al. |
| 2002/0177758 A1 | 11/2002 | Schoenberg |
| 2003/0027326 A1 | 2/2003 | Ulmsten et al. |
| 2003/0052787 A1 | 3/2003 | Zerhusen et al. |
| 2003/0058838 A1 | 3/2003 | Wengrovitz |
| 2003/0158466 A1 | 8/2003 | Lynn et al. |
| 2003/0216670 A1* | 11/2003 | Beggs ................ A61B 5/1115 600/595 |
| 2004/0013647 A1 | 1/2004 | Solomon et al. |
| 2004/0015103 A1 | 1/2004 | Aminian et al. |
| 2004/0073095 A1 | 4/2004 | Causey et al. |
| 2004/0090742 A1 | 5/2004 | Son et al. |
| 2004/0122787 A1 | 6/2004 | Avinash et al. |
| 2004/0126007 A1 | 7/2004 | Ziel et al. |
| 2004/0147818 A1 | 7/2004 | Levy et al. |
| 2004/0152957 A1 | 8/2004 | Stivoric et al. |
| 2004/0179332 A1 | 9/2004 | Smith et al. |
| 2004/0186357 A1 | 9/2004 | Soderberg et al. |
| 2004/0230179 A1 | 11/2004 | Shehada et al. |
| 2004/0243017 A1 | 12/2004 | Causevic |
| 2004/0254431 A1 | 12/2004 | Shehada et al. |
| 2004/0254432 A1 | 12/2004 | Shehada et al. |
| 2005/0005710 A1 | 1/2005 | Sage, Jr. |
| 2005/0009926 A1 | 1/2005 | Kreye et al. |
| 2005/0020918 A1 | 1/2005 | Wilk et al. |
| 2005/0038332 A1 | 2/2005 | Saidara et al. |
| 2005/0038680 A1 | 2/2005 | McMahon |
| 2005/0065417 A1 | 3/2005 | Ali et al. |
| 2005/0080336 A1 | 4/2005 | Byrd et al. |
| 2005/0096542 A1 | 5/2005 | Weng et al. |
| 2005/0113653 A1 | 5/2005 | Fox et al. |
| 2005/0124864 A1* | 6/2005 | Mack .................. A61B 5/024 600/300 |
| 2005/0125256 A1 | 6/2005 | Schoenberg |
| 2005/0148882 A1 | 7/2005 | Banet et al. |
| 2005/0164933 A1 | 7/2005 | Tymianski et al. |
| 2005/0191294 A1 | 9/2005 | Arap et al. |
| 2005/0208648 A1 | 9/2005 | Sage, Jr. et al. |
| 2005/0209518 A1 | 9/2005 | Sage, Jr. et al. |
| 2005/0228244 A1 | 10/2005 | Banet |
| 2005/0228299 A1 | 10/2005 | Banet |
| 2005/0242946 A1 | 11/2005 | Hubbard, Jr. et al. |
| 2005/0245831 A1 | 11/2005 | Banet |
| 2005/0245839 A1 | 11/2005 | Stivoric et al. |
| 2005/0261594 A1 | 11/2005 | Banet |
| 2005/0261598 A1 | 11/2005 | Banet et al. |
| 2005/0268401 A1* | 12/2005 | Dixon ................ A61B 5/1115 5/655.3 |
| 2005/0277872 A1 | 12/2005 | Colby et al. |
| 2006/0009697 A1 | 1/2006 | Banet et al. |
| 2006/0009698 A1 | 1/2006 | Banet et al. |
| 2006/0049936 A1* | 3/2006 | Collins, Jr. ......... A61B 5/1115 340/539.11 |
| 2006/0058647 A1 | 3/2006 | Strommer et al. |
| 2006/0084878 A1 | 4/2006 | Banet et al. |
| 2006/0089543 A1 | 4/2006 | Kim et al. |
| 2006/0094936 A1 | 5/2006 | Russ |
| 2006/0149393 A1 | 7/2006 | Calderon |
| 2006/0155175 A1 | 7/2006 | Ogino et al. |
| 2006/0200009 A1 | 9/2006 | Wekell et al. |
| 2006/0217684 A1 | 9/2006 | Shehada et al. |
| 2006/0217685 A1 | 9/2006 | Shehada et al. |
| 2006/0224413 A1 | 10/2006 | Kim et al. |
| 2006/0235300 A1 | 10/2006 | Weng et al. |
| 2006/0253042 A1 | 11/2006 | Stahmann et al. |
| 2007/0000490 A1 | 1/2007 | DeVries et al. |
| 2007/0021675 A1 | 1/2007 | Childre et al. |
| 2007/0027368 A1 | 2/2007 | Collins et al. |
| 2007/0032733 A1 | 2/2007 | Burton et al. |
| 2007/0055116 A1 | 3/2007 | Clark et al. |
| 2007/0055544 A1 | 3/2007 | Jung et al. |
| 2007/0060798 A1 | 3/2007 | Krupnik et al. |
| 2007/0088406 A1 | 4/2007 | Bennett et al. |
| 2007/0096897 A1 | 5/2007 | Weiner |
| 2007/0100222 A1 | 5/2007 | Mastrototaro et al. |
| 2007/0118399 A1 | 5/2007 | Avinash et al. |
| 2007/0140475 A1 | 6/2007 | Kurtock et al. |
| 2007/0142715 A1 | 6/2007 | Banet et al. |
| 2007/0156033 A1 | 7/2007 | Causey et al. |
| 2007/0159332 A1* | 7/2007 | Koblasz ............ G06F 19/3456 340/572.1 |
| 2007/0163589 A1 | 7/2007 | DeVries et al. |
| 2007/0185390 A1 | 8/2007 | Perkins et al. |
| 2007/0185393 A1 | 8/2007 | Zhou et al. |
| 2007/0232941 A1 | 10/2007 | Rabinovich |
| 2007/0244724 A1 | 10/2007 | Pendergast et al. |
| 2007/0250286 A1 | 10/2007 | Duncan et al. |
| 2007/0254593 A1 | 11/2007 | Jollota et al. |
| 2007/0255114 A1 | 11/2007 | Ackermann et al. |
| 2007/0255116 A1 | 11/2007 | Mehta et al. |
| 2007/0255250 A1 | 11/2007 | Moberg |
| 2007/0276261 A1 | 11/2007 | Banet et al. |
| 2007/0276262 A1 | 11/2007 | Banet et al. |
| 2007/0276632 A1 | 11/2007 | Banet et al. |
| 2008/0000479 A1 | 1/2008 | Elaz et al. |
| 2008/0003200 A1 | 1/2008 | Arap et al. |
| 2008/0021854 A1 | 1/2008 | Jung et al. |
| 2008/0033661 A1 | 2/2008 | Syroid et al. |
| 2008/0051670 A1 | 2/2008 | Banet et al. |
| 2008/0053438 A1 | 3/2008 | DeVries et al. |
| 2008/0058614 A1 | 3/2008 | Banet et al. |
| 2008/0058657 A1 | 3/2008 | Schwartz et al. |
| 2008/0082004 A1 | 4/2008 | Banet et al. |
| 2008/0090626 A1 | 4/2008 | Griffin et al. |
| 2008/0091089 A1 | 4/2008 | Guillory et al. |

(56) References Cited

U.S. PATENT DOCUMENTS

| | | |
|---|---|---|
| 2008/0091090 A1 | 4/2008 | Guillory et al. |
| 2008/0091471 A1 | 4/2008 | Michon et al. |
| 2008/0097167 A1 | 4/2008 | Yudkovitch et al. |
| 2008/0099366 A1 | 5/2008 | Niemiec et al. |
| 2008/0108884 A1 | 5/2008 | Kiani |
| 2008/0119412 A1 | 5/2008 | Tymianski et al. |
| 2008/0138278 A1 | 6/2008 | Scherz et al. |
| 2008/0169922 A1 | 7/2008 | Issokson |
| 2008/0171919 A1 | 7/2008 | Stivoric et al. |
| 2008/0188795 A1 | 8/2008 | Katz et al. |
| 2008/0194918 A1 | 8/2008 | Kulik et al. |
| 2008/0208912 A1 | 8/2008 | Garibaldi |
| 2008/0221396 A1 | 9/2008 | Garces et al. |
| 2008/0221399 A1 | 9/2008 | Zhou et al. |
| 2008/0221461 A1 | 9/2008 | Zhou et al. |
| 2008/0228077 A1 | 9/2008 | Wilk et al. |
| 2008/0275309 A1 | 11/2008 | Stivoric et al. |
| 2008/0281167 A1 | 11/2008 | Soderberg et al. |
| 2008/0281168 A1 | 11/2008 | Gibson et al. |
| 2008/0281181 A1 | 11/2008 | Manzione et al. |
| 2008/0287751 A1 | 11/2008 | Stivoric et al. |
| 2008/0292172 A1 | 11/2008 | Assmann et al. |
| 2008/0139354 A1 | 12/2008 | Bell et al. |
| 2008/0300020 A1 | 12/2008 | Nishizawa et al. |
| 2008/0312542 A1 | 12/2008 | Banet et al. |
| 2008/0319275 A1 | 12/2008 | Chiu et al. |
| 2008/0319327 A1 | 12/2008 | Banet et al. |
| 2008/0319354 A1 | 12/2008 | Bell et al. |
| 2009/0005651 A1 | 1/2009 | Ward et al. |
| 2009/0018422 A1 | 1/2009 | Banet et al. |
| 2009/0018453 A1 | 1/2009 | Banet et al. |
| 2009/0018808 A1 | 1/2009 | Bronstein et al. |
| 2009/0024008 A1 | 1/2009 | Brunner et al. |
| 2009/0052623 A1 | 2/2009 | Tome et al. |
| 2009/0054735 A1 | 2/2009 | Higgins et al. |
| 2009/0054743 A1 | 2/2009 | Stewart |
| 2009/0062682 A1 | 3/2009 | Bland et al. |
| 2009/0069642 A1 | 3/2009 | Gao et al. |
| 2009/0069868 A1 | 3/2009 | Bengtsson et al. |
| 2009/0099480 A1* | 4/2009 | Salgo ................ A61B 5/103 600/595 |
| 2009/0112072 A1 | 4/2009 | Banet et al. |
| 2009/0118628 A1 | 5/2009 | Zhou et al. |
| 2009/0119330 A1 | 5/2009 | Sampath et al. |
| 2009/0119843 A1* | 5/2009 | Rodgers ............. A61B 5/1115 5/611 |
| 2009/0124867 A1 | 5/2009 | Hirsch et al. |
| 2009/0131759 A1 | 5/2009 | Sims et al. |
| 2009/0143832 A1 | 6/2009 | Saba |
| 2009/0157058 A1 | 6/2009 | Ferren et al. |
| 2009/0171170 A1* | 7/2009 | Li ..................... A61B 5/00 600/301 |
| 2009/0171225 A1 | 7/2009 | Gadodia et al. |
| 2009/0177090 A1 | 7/2009 | Grunwald et al. |
| 2009/0182287 A1 | 7/2009 | Kassab |
| 2009/0226372 A1 | 9/2009 | Ruoslahti et al. |
| 2009/0247924 A1 | 10/2009 | Lamego et al. |
| 2009/0247984 A1 | 10/2009 | Lamego et al. |
| 2009/0264778 A1 | 10/2009 | Markowitz et al. |
| 2009/0275844 A1 | 11/2009 | Al-Ali |
| 2009/0281462 A1 | 11/2009 | Heliot et al. |
| 2009/0299157 A1 | 12/2009 | Telfort et al. |
| 2009/0309755 A1 | 12/2009 | Williamson et al. |
| 2009/0322540 A1 | 12/2009 | Richardson et al. |
| 2010/0004518 A1 | 1/2010 | Vo et al. |
| 2010/0030040 A1 | 2/2010 | Poeze et al. |
| 2010/0030094 A1 | 2/2010 | Lundback |
| 2010/0036209 A1 | 2/2010 | Ferren et al. |
| 2010/0069725 A1 | 3/2010 | Al-Ali |
| 2010/0125217 A1 | 5/2010 | Kuo et al. |
| 2010/0130875 A1 | 5/2010 | Banet et al. |
| 2010/0144627 A1 | 6/2010 | Vitek et al. |
| 2010/0160794 A1 | 6/2010 | Banet et al. |
| 2010/0160795 A1 | 6/2010 | Banet et al. |
| 2010/0160796 A1 | 6/2010 | Banet et al. |
| 2010/0160797 A1 | 6/2010 | Banet et al. |
| 2010/0160798 A1 | 6/2010 | Banet et al. |
| 2010/0168536 A1 | 7/2010 | Banet et al. |
| 2010/0168589 A1 | 7/2010 | Banet et al. |
| 2010/0185101 A1 | 7/2010 | Sakai et al. |
| 2010/0198622 A1 | 8/2010 | Gajic et al. |
| 2010/0210958 A1 | 8/2010 | Manwaring et al. |
| 2010/0261979 A1 | 10/2010 | Kiani |
| 2010/0261982 A1 | 10/2010 | Noury et al. |
| 2010/0298650 A1 | 11/2010 | Moon et al. |
| 2010/0298651 A1 | 11/2010 | Moon et al. |
| 2010/0298652 A1 | 11/2010 | McCombie et al. |
| 2010/0298653 A1 | 11/2010 | McCombie et al. |
| 2010/0298654 A1 | 11/2010 | McCombie et al. |
| 2010/0298655 A1 | 11/2010 | McCombie et al. |
| 2010/0298656 A1 | 11/2010 | McCombie et al. |
| 2010/0298657 A1 | 11/2010 | McCombie et al. |
| 2010/0298659 A1 | 11/2010 | Mccombie et al. |
| 2010/0298660 A1 | 11/2010 | McCombie et al. |
| 2010/0298661 A1 | 11/2010 | Mccombie et al. |
| 2010/0298742 A1 | 11/2010 | Perlman et al. |
| 2010/0305412 A1 | 12/2010 | Darrah et al. |
| 2010/0312103 A1 | 12/2010 | Gorek et al. |
| 2010/0317936 A1 | 12/2010 | Al-Ali et al. |
| 2010/0317951 A1 | 12/2010 | Rutkowski et al. |
| 2010/0324384 A1 | 12/2010 | Moon et al. |
| 2010/0324385 A1 | 12/2010 | Moon et al. |
| 2010/0324386 A1 | 12/2010 | Moon et al. |
| 2010/0324387 A1 | 12/2010 | Moon et al. |
| 2010/0324388 A1 | 12/2010 | Moon et al. |
| 2010/0324389 A1 | 12/2010 | Moon et al. |
| 2011/0001605 A1 | 1/2011 | Kiani et al. |
| 2011/0021930 A1 | 1/2011 | Mazzeo et al. |
| 2011/0023130 A1 | 1/2011 | Gudgel et al. |
| 2011/0028809 A1 | 2/2011 | Goodman |
| 2011/0046495 A1 | 2/2011 | Osypka |
| 2011/0066051 A1* | 3/2011 | Moon ................. A61B 5/0002 600/509 |
| 2011/0077473 A1 | 3/2011 | Lisogurski |
| 2011/0077488 A1 | 3/2011 | Buxton et al. |
| 2011/0078596 A1 | 3/2011 | Rawlins et al. |
| 2011/0080294 A1 | 4/2011 | Tanishima et al. |
| 2011/0082711 A1 | 4/2011 | Poeze et al. |
| 2011/0087084 A1 | 4/2011 | Jeong et al. |
| 2011/0087117 A1 | 4/2011 | Tremper et al. |
| 2011/0087756 A1 | 4/2011 | Biondi |
| 2011/0098583 A1 | 4/2011 | Pandia et al. |
| 2011/0105854 A1 | 5/2011 | Kiani et al. |
| 2011/0105956 A1 | 5/2011 | Hirth |
| 2011/0118573 A1 | 5/2011 | Mckenna |
| 2011/0152629 A1 | 6/2011 | Eaton et al. |
| 2011/0172967 A1 | 7/2011 | Al-Ali et al. |
| 2011/0184252 A1 | 7/2011 | Archer et al. |
| 2011/0184253 A1 | 7/2011 | Archer et al. |
| 2011/0208015 A1 | 8/2011 | Welch et al. |
| 2011/0208018 A1 | 8/2011 | Kiani |
| 2011/0208073 A1 | 8/2011 | Matsukawa et al. |
| 2011/0209915 A1 | 9/2011 | Telfort et al. |
| 2011/0212090 A1 | 9/2011 | Pedersen et al. |
| 2011/0213212 A1 | 9/2011 | Al-Ali |
| 2011/0224498 A1 | 9/2011 | Banet et al. |
| 2011/0224499 A1 | 9/2011 | Banet et al. |
| 2011/0224500 A1 | 9/2011 | Banet et al. |
| 2011/0224506 A1 | 9/2011 | Moon et al. |
| 2011/0224507 A1 | 9/2011 | Banet et al. |
| 2011/0224508 A1 | 9/2011 | Moon et al. |
| 2011/0224556 A1 | 9/2011 | Moon et al. |
| 2011/0224557 A1 | 9/2011 | Banet et al. |
| 2011/0224564 A1 | 9/2011 | Moon et al. |
| 2011/0227739 A1 | 9/2011 | Gilham et al. |
| 2011/0230733 A1 | 9/2011 | Al-Ali |
| 2011/0237911 A1 | 9/2011 | Lamego et al. |
| 2011/0257489 A1 | 10/2011 | Banet et al. |
| 2011/0257544 A1 | 10/2011 | Kaasinen et al. |
| 2011/0257551 A1 | 10/2011 | Banet et al. |
| 2011/0257552 A1 | 10/2011 | Banet et al. |
| 2011/0257553 A1 | 10/2011 | Banet et al. |
| 2011/0257554 A1 | 10/2011 | Banet et al. |
| 2011/0257555 A1 | 10/2011 | Banet et al. |

(56) References Cited

U.S. PATENT DOCUMENTS

| | | | |
|---|---|---|---|
| 2011/0263950 A1* | 10/2011 | Larson | A61B 5/024 600/301 |
| 2011/0288421 A1 | 11/2011 | Banet et al. | |
| 2011/0295094 A1 | 12/2011 | Doyle et al. | |
| 2012/0001751 A1 | 1/2012 | Baker et al. | |
| 2012/0004579 A1 | 1/2012 | Luo et al. | |
| 2012/0029300 A1* | 2/2012 | Paquet | A61B 5/6833 600/300 |
| 2012/0029304 A1 | 2/2012 | Medina et al. | |
| 2012/0029879 A1* | 2/2012 | Sing | A61B 5/1116 702/189 |
| 2012/0059230 A1 | 3/2012 | Teller et al. | |
| 2012/0059267 A1 | 3/2012 | Lamego et al. | |
| 2012/0071771 A1 | 3/2012 | Behar | |
| 2012/0075464 A1* | 3/2012 | Derenne | A61B 5/0013 348/135 |
| 2012/0095778 A1 | 4/2012 | Gross et al. | |
| 2012/0101353 A1 | 4/2012 | Reggiardo et al. | |
| 2012/0108983 A1 | 5/2012 | Banet et al. | |
| 2012/0116175 A1 | 5/2012 | Al-Ali et al. | |
| 2012/0117209 A1* | 5/2012 | Sinha | G06F 21/88 709/221 |
| 2012/0123799 A1 | 5/2012 | Nolen et al. | |
| 2012/0136221 A1 | 5/2012 | Killen et al. | |
| 2012/0179006 A1 | 7/2012 | Jansen et al. | |
| 2012/0179011 A1 | 7/2012 | Moon et al. | |
| 2012/0184120 A1 | 7/2012 | Basta et al. | |
| 2012/0190949 A1 | 7/2012 | McCombie et al. | |
| 2012/0197619 A1 | 8/2012 | Namer Yelin et al. | |
| 2012/0203078 A1* | 8/2012 | Sze | G06F 19/3418 600/301 |
| 2012/0209082 A1 | 8/2012 | Al-Ali | |
| 2012/0209084 A1 | 8/2012 | Olsen et al. | |
| 2012/0226160 A1 | 9/2012 | Kudoh | |
| 2012/0227739 A1 | 9/2012 | Kiani | |
| 2012/0239434 A1 | 9/2012 | Breslow et al. | |
| 2012/0242501 A1* | 9/2012 | Tran | A61B 5/0024 340/870.02 |
| 2012/0265039 A1 | 10/2012 | Kiani | |
| 2012/0282583 A1 | 11/2012 | Thaler et al. | |
| 2012/0283524 A1 | 11/2012 | Kiani et al. | |
| 2012/0284053 A1 | 11/2012 | Rosenfeld | |
| 2012/0286955 A1 | 11/2012 | Welch et al. | |
| 2012/0294801 A1 | 11/2012 | Scherz et al. | |
| 2012/0296178 A1 | 11/2012 | Lamego et al. | |
| 2012/0302894 A1 | 11/2012 | Diab et al. | |
| 2012/0319816 A1 | 12/2012 | Al-Ali | |
| 2012/0330112 A1 | 12/2012 | Lamego et al. | |
| 2013/0006131 A1 | 1/2013 | Narayan et al. | |
| 2013/0006151 A1 | 1/2013 | Main et al. | |
| 2013/0023775 A1 | 1/2013 | Lamego et al. | |
| 2013/0035603 A1 | 2/2013 | Jarausch et al. | |
| 2013/0045685 A1 | 2/2013 | Kiani | |
| 2013/0046197 A1 | 2/2013 | Dlugos et al. | |
| 2013/0046204 A1 | 2/2013 | Lamego et al. | |
| 2013/0041591 A1 | 3/2013 | Lamego | |
| 2013/0060108 A1 | 3/2013 | Schurman et al. | |
| 2013/0060147 A1 | 3/2013 | Welch et al. | |
| 2013/0079610 A1 | 3/2013 | Al-Ali | |
| 2013/0096405 A1 | 4/2013 | Garfio | |
| 2013/0096936 A1 | 4/2013 | Sampath et al. | |
| 2013/0109929 A1 | 5/2013 | Menzel | |
| 2013/0109935 A1 | 5/2013 | Al-Ali et al. | |
| 2013/0109937 A1 | 5/2013 | Banet et al. | |
| 2013/0116515 A1 | 5/2013 | Banet et al. | |
| 2013/0155889 A1* | 6/2013 | Brownworth | H04W 36/0083 370/252 |
| 2013/0162433 A1 | 6/2013 | Muhsin et al. | |
| 2013/0178749 A1 | 7/2013 | Lamego | |
| 2013/0190581 A1 | 7/2013 | Al-Ali et al. | |
| 2013/0197328 A1 | 8/2013 | Diab et al. | |
| 2013/0211214 A1 | 8/2013 | Olsen | |
| 2013/0243021 A1 | 9/2013 | Siskavich | |
| 2013/0253334 A1 | 9/2013 | Al-Ali et al. | |
| 2013/0261494 A1* | 10/2013 | Bloom | A61B 5/447 600/549 |
| 2013/0262730 A1 | 10/2013 | Al-Ali et al. | |
| 2013/0274571 A1 | 10/2013 | Diab et al. | |
| 2013/0296672 A1 | 11/2013 | O'Neil et al. | |
| 2013/0317327 A1 | 11/2013 | Al-Ali et al. | |
| 2013/0317370 A1 | 11/2013 | Dalvi et al. | |
| 2013/0317393 A1* | 11/2013 | Weiss | G06F 19/3406 600/587 |
| 2013/0324808 A1 | 12/2013 | Al-Ali et al. | |
| 2013/0324817 A1 | 12/2013 | Diab | |
| 2013/0331670 A1 | 12/2013 | Kiani | |
| 2013/0338461 A1 | 12/2013 | Lamego et al. | |
| 2013/0340176 A1* | 12/2013 | Stevens | A61G 7/057 5/710 |
| 2013/0342691 A1 | 12/2013 | Lewis et al. | |
| 2014/0005502 A1 | 1/2014 | Klap et al. | |
| 2014/0012100 A1 | 1/2014 | Al-Ali et al. | |
| 2014/0022081 A1* | 1/2014 | Ribble | A61B 5/746 340/573.4 |
| 2014/0025010 A1 | 1/2014 | Stroup et al. | |
| 2014/0025306 A1 | 1/2014 | Weber et al. | |
| 2014/0031650 A1 | 1/2014 | Weber et al. | |
| 2014/0034353 A1 | 2/2014 | Al-Ali et al. | |
| 2014/0046674 A1 | 2/2014 | Rosenfeld | |
| 2014/0051952 A1 | 2/2014 | Reichgott et al. | |
| 2014/0051953 A1 | 2/2014 | Lamego et al. | |
| 2014/0051954 A1 | 2/2014 | Al-Ali et al. | |
| 2014/0058230 A1 | 2/2014 | Abdul-Hafiz et al. | |
| 2014/0066783 A1 | 3/2014 | Kiani et al. | |
| 2014/0073167 A1 | 3/2014 | Al-Ali et al. | |
| 2014/0077956 A1 | 3/2014 | Sampath et al. | |
| 2014/0081097 A1 | 3/2014 | Al-Ali et al. | |
| 2014/0081099 A1 | 3/2014 | Banet et al. | |
| 2014/0081100 A1 | 3/2014 | Muhsin et al. | |
| 2014/0081175 A1 | 3/2014 | Telfort | |
| 2014/0088385 A1 | 3/2014 | Moon et al. | |
| 2014/0094667 A1 | 4/2014 | Schurman et al. | |
| 2014/0100434 A1 | 4/2014 | Diab et al. | |
| 2014/0114199 A1 | 4/2014 | Lamego et al. | |
| 2014/0120564 A1 | 5/2014 | Workman et al. | |
| 2014/0121482 A1 | 5/2014 | Merritt et al. | |
| 2014/0121483 A1 | 5/2014 | Kiani | |
| 2014/0125495 A1 | 5/2014 | Al-Ali | |
| 2014/0127137 A1 | 5/2014 | Bellott et al. | |
| 2014/0128696 A1 | 5/2014 | Al-Ali | |
| 2014/0128699 A1 | 5/2014 | Al-Ali et al. | |
| 2014/0129702 A1 | 5/2014 | Lamego et al. | |
| 2014/0135588 A1 | 5/2014 | Al-Ali et al. | |
| 2014/0142399 A1 | 5/2014 | Al-Ali et al. | |
| 2014/0142401 A1 | 5/2014 | Al-Ali et al. | |
| 2014/0142402 A1 | 5/2014 | Al-Ali et al. | |
| 2014/0142445 A1 | 5/2014 | Banet et al. | |
| 2014/0152673 A1 | 6/2014 | Lynn et al. | |
| 2014/0155712 A1 | 6/2014 | Lamego et al. | |
| 2014/0163344 A1 | 6/2014 | Al-Ali | |
| 2014/0163393 A1 | 6/2014 | McCombie et al. | |
| 2014/0163402 A1 | 6/2014 | Lamego et al. | |
| 2014/0166076 A1 | 6/2014 | Kiani et al. | |
| 2014/0171763 A1 | 6/2014 | Diab | |
| 2014/0180038 A1 | 6/2014 | Kiani | |
| 2014/0180154 A1 | 6/2014 | Sierra et al. | |
| 2014/0194709 A1 | 7/2014 | Al-Ali et al. | |
| 2014/0194711 A1 | 7/2014 | Al-Ali | |
| 2014/0194766 A1 | 7/2014 | Al-Ali et al. | |
| 2014/0200415 A1 | 7/2014 | McCombie et al. | |
| 2014/0200420 A1 | 7/2014 | Al-Ali | |
| 2014/0200422 A1 | 7/2014 | Weber et al. | |
| 2014/0206963 A1 | 7/2014 | Al-Ali | |
| 2014/0213864 A1 | 7/2014 | Abdul-Hafiz et al. | |
| 2014/0235964 A1 | 8/2014 | Banet et al. | |
| 2014/0243627 A1 | 8/2014 | Diab et al. | |
| 2014/0249431 A1 | 9/2014 | Banet et al. | |
| 2014/0249432 A1 | 9/2014 | Banet et al. | |
| 2014/0249433 A1 | 9/2014 | Banet et al. | |
| 2014/0249434 A1 | 9/2014 | Banet et al. | |
| 2014/0249435 A1 | 9/2014 | Banet et al. | |
| 2014/0249440 A1 | 9/2014 | Banet et al. | |
| 2014/0249441 A1 | 9/2014 | Banet et al. | |

(56) References Cited

U.S. PATENT DOCUMENTS

| | | | |
|---|---|---|---|
| 2014/0249442 A1 | 9/2014 | Banet et al. | |
| 2014/0257056 A1 | 9/2014 | Moon et al. | |
| 2014/0257057 A1* | 9/2014 | Reis Cunha | A61B 5/1116 600/301 |
| 2014/0266787 A1* | 9/2014 | Tran | A61B 5/0022 340/870.07 |
| 2014/0266790 A1 | 9/2014 | Al-Ali et al. | |
| 2014/0275808 A1 | 9/2014 | Poeze et al. | |
| 2014/0275835 A1 | 9/2014 | Lamego et al. | |
| 2014/0275871 A1 | 9/2014 | Lamego et al. | |
| 2014/0275872 A1 | 9/2014 | Merritt et al. | |
| 2014/0275881 A1 | 9/2014 | Lamego et al. | |
| 2014/0276145 A1 | 9/2014 | Banet et al. | |
| 2014/0276175 A1 | 9/2014 | Banet et al. | |
| 2014/0288400 A1 | 9/2014 | Diab et al. | |
| 2014/0296664 A1 | 10/2014 | Bruinsma et al. | |
| 2014/0301893 A1 | 10/2014 | Stroup et al. | |
| 2014/0303520 A1 | 10/2014 | Telfort et al. | |
| 2014/0309506 A1 | 10/2014 | Lamego et al. | |
| 2014/0309559 A1 | 10/2014 | Telfort et al. | |
| 2014/0316228 A1 | 10/2014 | Blank et al. | |
| 2014/0323825 A1 | 10/2014 | Al-Ali et al. | |
| 2014/0330092 A1 | 11/2014 | Al-Ali et al. | |
| 2014/0330098 A1 | 11/2014 | Merritt et al. | |
| 2014/0330099 A1 | 11/2014 | Al-Ali et al. | |
| 2014/0333440 A1 | 11/2014 | Kiani | |
| 2014/0336481 A1 | 11/2014 | Shakespeare et al. | |
| 2014/0343436 A1 | 11/2014 | Kiani | |
| 2014/0343889 A1* | 11/2014 | Ben Shalom | G06F 19/3431 702/139 |
| 2014/0357966 A1 | 12/2014 | Al-Ali | |
| 2014/0375428 A1 | 12/2014 | Park | |
| 2015/0018650 A1 | 1/2015 | Al-Ali et al. | |
| 2015/0094618 A1* | 4/2015 | Russell | A61B 5/447 600/587 |
| 2015/0097701 A1 | 4/2015 | Al-Ali et al. | |
| 2015/0106121 A1 | 4/2015 | Muhsin et al. | |
| 2015/0164437 A1 | 6/2015 | McCombie et al. | |
| 2015/0282717 A1 | 10/2015 | McCombie et al. | |
| 2016/0022224 A1 | 1/2016 | Banet et al. | |
| 2016/0045163 A1 | 2/2016 | Weisner et al. | |
| 2016/0143546 A1 | 5/2016 | McCombie et al. | |
| 2017/0055851 A1 | 3/2017 | Al-Ali | |
| 2017/0055882 A1 | 3/2017 | Al-Ali et al. | |
| 2017/0055887 A1 | 3/2017 | Al-Ali | |
| 2017/0055896 A1 | 3/2017 | Al-Ali et al. | |

FOREIGN PATENT DOCUMENTS

| | | |
|---|---|---|
| EP | 2 766 834 | 8/2014 |
| EP | 2811894 | 12/2014 |
| JP | 10-336064 | 12/1998 |
| JP | 2002-513602 | 5/2002 |
| JP | 2002-542493 | 12/2002 |
| JP | 2005-218036 | 8/2005 |
| JP | 2005-295375 | 10/2005 |
| JP | 2007-095365 | 4/2007 |
| JP | 2007-174051 | 7/2007 |
| JP | 2008-519635 | 6/2008 |
| JP | 2009-017959 | 1/2009 |
| JP | 2010-524510 | 7/2010 |
| JP | 2014/533997 | 12/2014 |
| WO | WO 98/29790 | 7/1998 |
| WO | WO 99/13766 | 3/1999 |
| WO | WO 00/063713 | 10/2000 |
| WO | WO 2004/056266 | 7/2004 |
| WO | WO 2004/059551 | 7/2004 |
| WO | WO 2011/002904 | 1/2011 |
| WO | WO 2013/056160 | 4/2013 |
| WO | WO 2013/119982 | 8/2013 |
| WO | WO 2015/054665 | 4/2015 |
| WO | WO 2017/040700 | 3/2017 |

OTHER PUBLICATIONS

Capuano et at. "Remote Telemetry—New Twists for Old Technology." Nursing Management. vol. 26, No. 7. Jul. 1995.

Elmer-Dewitt, Philip, Apple's iWatch: The killer apps may be in hospitals, not health clubs, Fortune.com, Feb. 3, 2014, http://fortune.com/2014/02/03/apples-iwatch-the-killer-apps-may-be-in-hospitals-not-health-clubs/, in 4 pages.

EP Office Action dated Jun. 15, 2015. EP App. No. 10195398.2.

Grundy et al. "Telemedicine in Critical Care: An Experiment in Health Care Delivery." Oct. 1977.

Grundy et al. "Telemedicine in Critical Care: Problems in design, implementation and assessment." vol. 10, No. 7. Jul. 1982.

Rysavy, "Making the Call with Two-Way Paging", Network Computing, Published Jan. 15, 1997, www.rysavy.com/Articles/twoway.htm.

Extended European Search Report for European Application No. 10195398.2 dated Jul. 5, 2012.

PCT International Search Report & Written Opinion, App. No. PCT/US2012/060109, dated Jun. 5, 2013.

PCT International Preliminary Report on Patentability for Application No. PCT/US2012/060109, dated Apr. 24, 2014.

PCT International Search Report & Written Opinion, App. No. PCT/US2014/060177, dated Dec. 19, 2014.

Wachter, S. Blake; Journal of the American Medical Informatics Association; The Employment of an Iterative Design Process to Develop a Pulmonary Graphical Display; vol. 10, No. 4, Jul./Aug. 2003; pp. 363-372.

PCT International Search Report and Written Opinion, App. No. PCT/US2013/025384, dated Aug. 6, 2013.

U.S. Appl. No. 15/253,567, Wireless Patient Monitoring Systems and Methods, filed Aug. 31, 2016.

U.S. Appl. No. 15/253,482, Systems and Methods to Monitor Repositioning of a Patient, filed Aug. 31, 2016.

U.S. Appl. No. 15/253,355, Systems and Methods for Patient Fall Detection, filed Aug. 31, 2016.

U.S. Appl. No. 15/253,536, Patient-Worn Wireless Physiological Sensor, filed Aug. 31, 2016.

Aminian et al., "Spatio-Temporal Parameters of Gait Measured by an Ambulatory System Using Miniature Gyroscopes", Journal of Biomechanics, 2002, vol. 35, pp. 689-699.

Anliker et al., "AMON: A Wearable Multiparameter Medical Monitoring and Alert System", IEEE Transactions on Information Technology in Biomedicine, vol. 8, No. 4, Dec. 2004, pp. 415-427.

Asada et al., "Mobile Monitoring with Wearable Photoplethysmographic Biosensors", IEEE Engineering in Medicine and Biology Magazine, May/Jun. 2003, pp. 28-40.

Ayello et al., "How and Why to Do Pressure Ulcer Risk Assessment", Advances in Skin & Wound Care, May/Jun. 2002, vol. 15, No. 3., pp. 125-133.

Bergstrom et al., "A Prospective Study of Pressure Sore Risk Among Institutionalized Elderly", Journal of the American Geriatrics Society, Aug. 1992, vol. 40, No. 8, pp. 747-758.

Bourke et al., "Evaluation of a Threshold-Based Tri-Axial Accelerometer Fall Detection Algoithm", Gait & Posture, vol. 26, 2007, pp. 194-199.

Campo et al., "Wireless Fall Sensor with GPS Location for Monitoring the Elderly", 30th Annual International IEEE EMBS Conference Vancouver, British Columbia, Canada, Aug. 20-24, 2008, pp. 498-501.

Caporusso et al., "A Pervasive Solution for Risk Awareness in the Context of Fall Prevention", Pervasive Health, 2009, pp. 8.

Chen et al., "In-Bed Fibre Optic Breathing and Movement Sensor for Non-Intrusive Monitoring", Proceedings of SPIE vol. 7173, 2009, pp. 6.

Chen et al., "Wearable Sensors for Reliable Fall Detection", Proceedings of the 2005 IEEE Engineering in Medicine and Biology 27th Annual Conference, Shanghai, China, Sep. 1-4, 2005, pp. 3551-3554.

Degen et al., "Speedy: A Fall Detector in a Wrist Watch", Proceedings of the Seventh IEEE International Symposium on Wearable Computers (ISWC'03), 2003, pp. 184-187.

(56) References Cited

OTHER PUBLICATIONS

Di Rienzo et al., "MagIC System: a New Textile-BasedWearable Device for Biological Signal Monitoring. Applicability in Daily Life and Clinical Setting", Proceedings of the 2005 IEEE Engineering in Medicine and Biology 27th Annual Conference Shanghai, China, Sep. 1-4, 2005, pp. 7167-7169.

Dinh et al, "A Fall and Near-Fall Assessment and Evaluation System", The Open Biomedical Engineering Journal, 2009, vol. 3, pp. 1-7.

Giansanti et al., "Assessment of Fall-Risk by Means of a Neural Network Based on Parameters Assessed by a Wearable Device During Posturography", Medical Engineering & Physics, vol. 30, 2008, pp. 367-372.

Giansanti, Daniele, "Investigation of Fall-Risk Using a Wearable Device with Accelerometers and Rate Gyroscopes", Institute of Physics Publishing, Physiological Measurement, vol. 27, 2006, pp. 1081-1090.

Gunningberg et al., "Accuracy in the Recording of Pressure Ulcers and Prevention after Implementing an Electronic Health Record in Hospital Care", Quality Safe Health Care, 2008, vol. 17, pp. 281-285.

Harada et al., "Portable Orientation Estimation Device Based on Accelerometers, Magnetometers and Gyroscope Sensors for Sensor Network", IEEE Conference on Multisensor Fusion and Integration for Intelligent Systems 2003, 2003, pp. 191-196.

Hwang et al., "Development of Novel Algorithm and Real-time Monitoring Ambulatory System Using Bluetooth Module for Fall Detection in the Elderly", Proceedings of the 26th Annual International Conference of the IEEE EMBS, Sep. 1-5, 2004, pp. 2204-2207.

Kang et al., "A Wrist-Worn Integrated Health Monitoring Instrument with a Tele-Reporting Device for Telemedicine and Telecare", IEEE Transaction on Instrumentation and Measurement, vol. 55, No. 5, Oct. 2006, pp. 1655-1661.

Kärki et al., "Pressure Mapping System for Physiological Measurements", XVIII IMEKO World Congress, Metrology for a Sustainable Development, Sep. 17-22, 2006, Rio de Janeiro, Brazil, pp. 5.

Lindemann et al., "Evaluation of a Fall Detector Based on Accelerometers: A Pilot Study", Medical & Biological Engineering & Computing, vol. 43, 2005, pp. 548-551.

Linder-Ganz et al., "Real-Time Continuous Monitoring of Sub-Dermal Tissue Stresses Under the Ischial Tuberosities in Individuals with Spinal Cord Injury", Proceedings of the ASME 2008 Summer Bioengineering Conference (SBC2008), Jun. 25-29, 2008, Marriott Resort, Marco Island, Florida, pp. 2.

Luo et al., "A Dynamic Motion Pattern Analysis Approach to Fall Detection", 2004 IEEE International Workshop on Biomedical Circuits & Systems, Dec. 1-3, 2004, pp. S2.1-5-S2.1-8.

Mathie et al., "A System for Monitoring Posture and Physical Activity Using Accelerometers", Engineering in Medicine and Biology Society, 2001. Proceedings of the 23rd Annual International Conference of the IEEE, Oct. 25-28, 2001, pp. 3654-3657.

McInerney, Joan A., "Reducing Hospital-Acquired Pressure Ulcer Prevalence Through a Focused Prevention Program", Advances in Skin & Wound Care, vol. 21, No. 2, Feb. 2008, pp. 75-78.

Merbitz et al., "Wheelchair Push-ups: Measuring Pressure Relief Frequency", Archives of Physical Medicine and Rehabilitation, vol. 66, No. 7, Jul. 1985, pp. 433-438.

Narayanan et al., "Falls Management: Detection and Prevention, Using a Waist-Mounted Triaxial Accelerometer", Proceedings of the 29th Annual International Conference of the IEEE EMBS Cité Internationale, Lyon, France, Aug. 23-26, 2007, pp. 4037-4040.

Noury, Norbert, "A Smart Sensor for the Remote Follow Up of Activity and Fall Detection of the Elderly", 2nd Annual International IEEE-EMBS Special Topic Conference on Microtechnologies in Medicine & Biology, May 2-4, 2002, pp. 314-317.

Nyan et al., "A Wearable System for Pre-Impact Fall Detection", Journal of Biomechanics, vol. 41, 2008, pp. 3475-3481.

Nyan et al., "Garment-Based Detection of Falls and Activities of Daily Living Using 3-Axis MEMS Accelerometer", Institute of Physics Publishing, International MEMS Conference 2006, Journal of Physics: Conference Series 34, 2006, pp. 1059-1067.

O'Donovan et al., "A Context Aware Wireless Body Area Network", Pervasive Health, 2009, pp. 8.

Pérolle et al., "Automatic Fall Detection and Activity Monitoring for Elderly", Jan. 2007, pp. 6.

Po et al., "Overview of MEMSWear II—Incorporating MEMS Technology Into Smart Shirt for Geriatric Care", Institute of Physics Publishing, International MEMS Conference 2006, Journal of Physics: Conference Series 34, 2006, pp. 1079-1085.

Prado et al., "Distributed Intelligent Architecture for Falling Detection and Physical Activity Analysis in the Elderly", Proceedings of the Second Joint EMBS/BMES Conference, Oct. 23-26, 2002, pp. 1910-1911.

Rithalia et al., "Quantification of Pressure Relief Using Interface Pressure and Tissue Perfusion in Alternating Pressure Air Mattresses", Archives of Physical Medicine and Rehabilitation, vol. 81, Oct. 2000, pp. 1364-1369.

Sakai et al., "Continuous Monitoring of Interface Pressure Distribution in Intensive Care Patients for Pressure Ulcer Prevention", Journal of Advanced Nursing, vol. 65, No. 4, 2009, pp. 809-817.

Spillman Jr., et al., "A 'Smart' Bed for Non-Intrusive Monitoring of Patient Physiological Factors", Measurement Science and Technology, Aug. 2004, vol. 15, No. 8, pp. 1614-1620.

Webster, John G., "A Pressure Mat for Preventing Pressure Sores", IEEE Engineering in Medicine & Bioloogy Society 11th Annual International Conference, 1989, pp. 2.

Williams et al., "A Remote Electronic Monitoring System for the Prevention of Pressure Sores", Proceedings of the 19th International Conference, IEEE/EMBS Oct. 30-Nov. 2, 1997, Chicago, IL, pp. 1076-1079.

Wu et al., "Portable Preimpact Fall Detector With Inertial Sensors", IEEE Transactions on Neural Systems and Rehabilitation Engineering, vol. 16, No. 2, Apr. 2008, pp. 178-183.

Dhillon et al., "Towards the Prevention of Pressure Ulcers with a Wearable Patient Posture Monitor Based on Adaptive Accelerometer Alignment", 34th Annual International Conference of the IEEE EMBS, San Diego, CA, Aug. 28-Sep. 1, 2012, pp. 4513-4516.

Gunningberg et al., "Improved Quality and Comprehensiveness in Nursing Documentation of Pressure Ulcers after Implementing an Electronic Health Record in Hospital Care", Journal of Clinical Nursing, 2009, vol. 18, pp. 1557-1564.

International Preliminary Report on Patentability & Written Opinion in PCT Application No. PCT/US2014/060177, dated Apr. 21, 2016.

International Search Report & Written Opinion in PCT Application No. PCT/US2016/049751, dated Mar. 13, 2017.

Invitation to Pay Additional Fees in PCT Application No. PCT/US2016/049751, dated Jan. 18, 2017.

Li et al., "Accurate, Fast Fall Detection Using Gyroscopes and Accelerometer-Derived Posture Information", Conference Paper, Sixth International Workshop on Wearable and Implantable Body Sensor Networks, BSN 2009, Berkeley, CA, USA, Jun. 3-5, 2009, pp. 6.

* cited by examiner

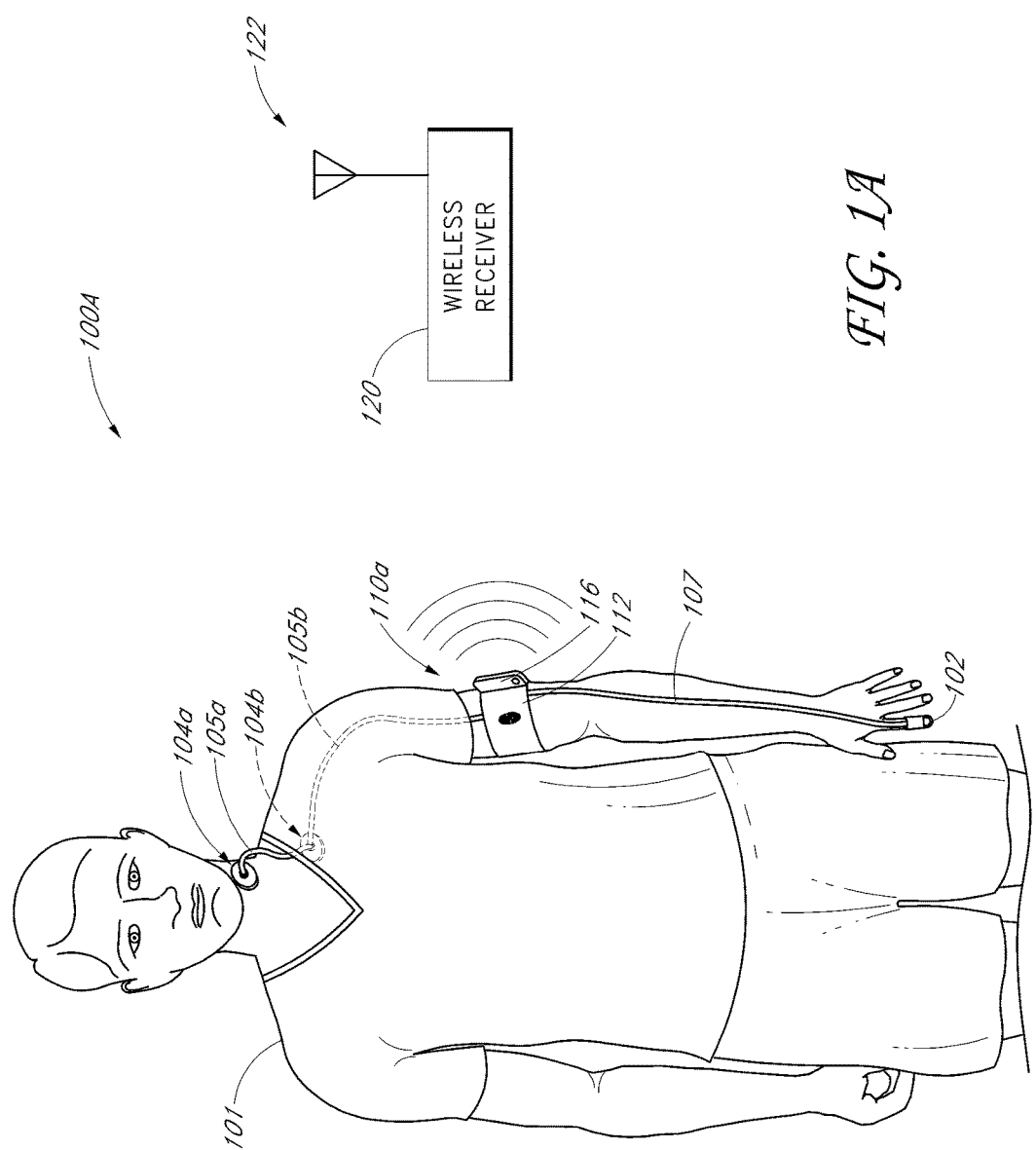

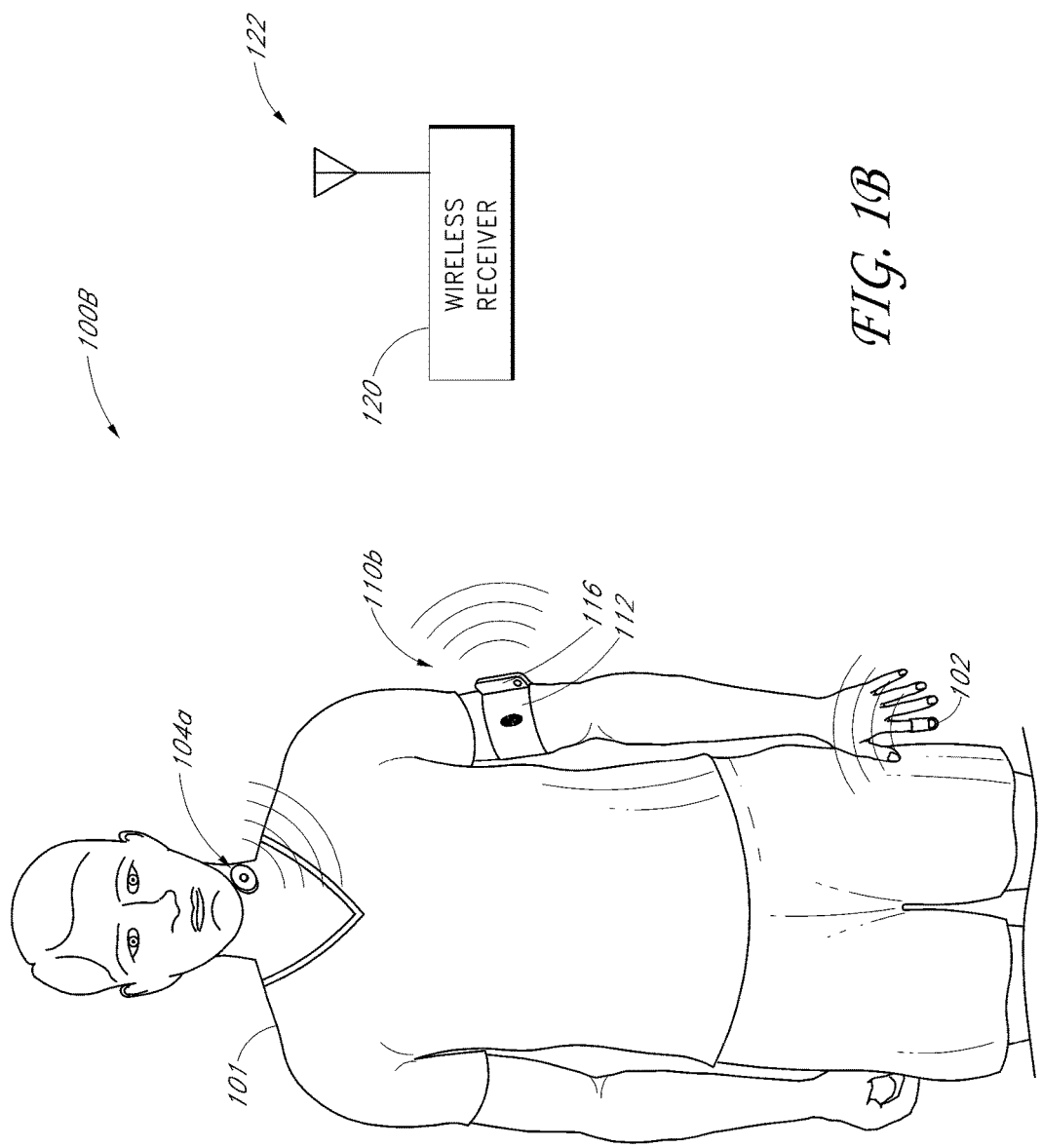

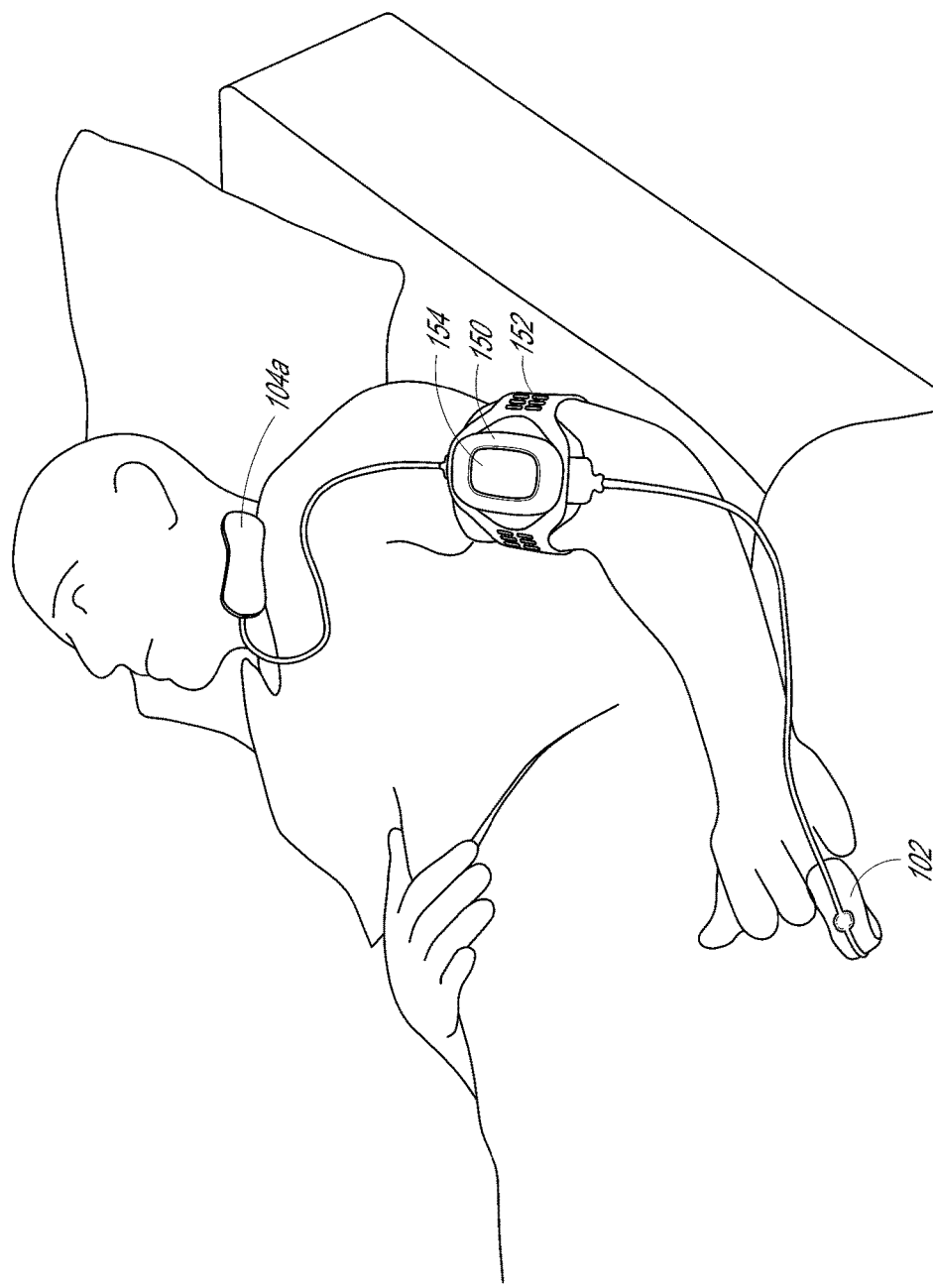

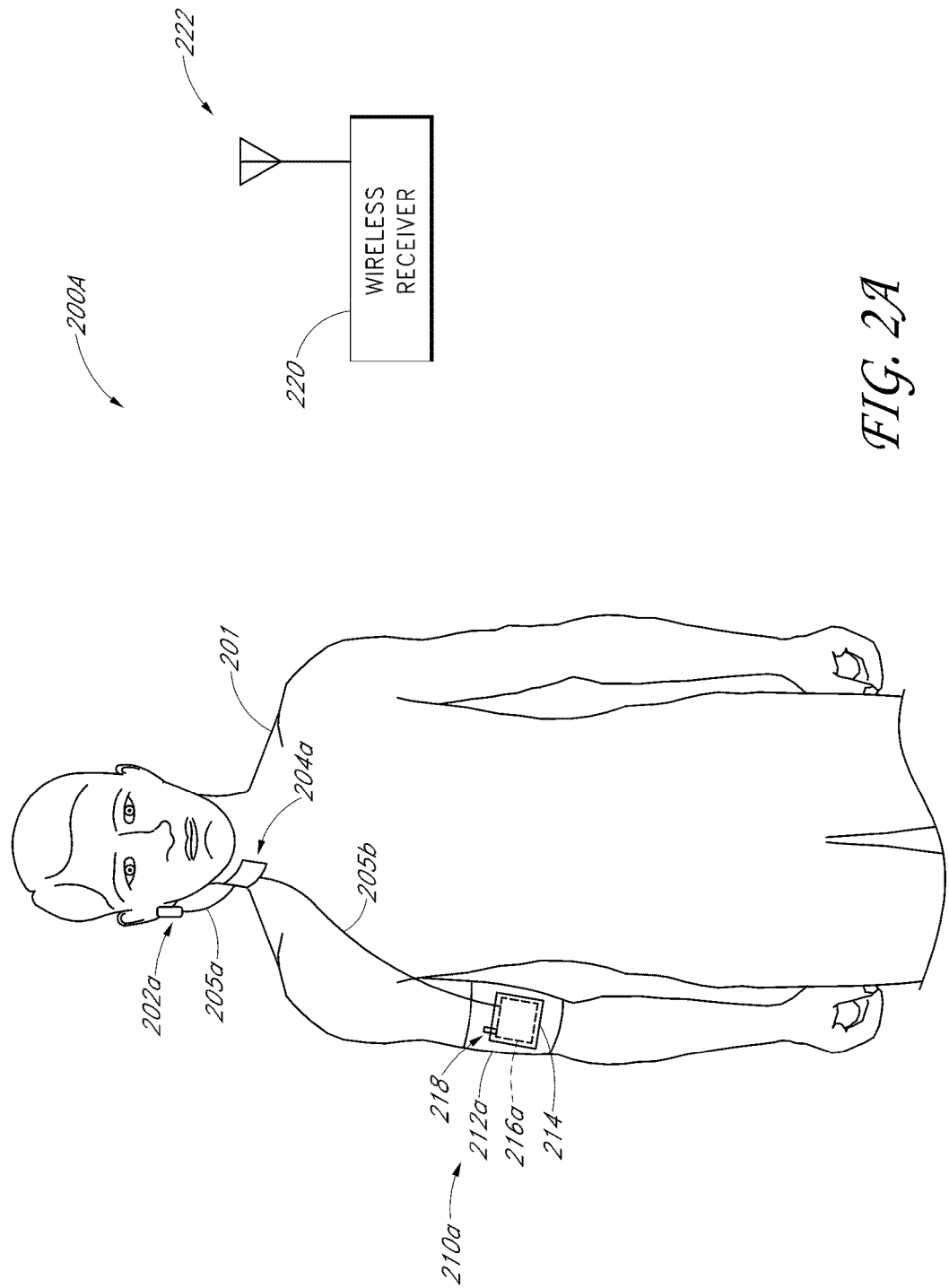

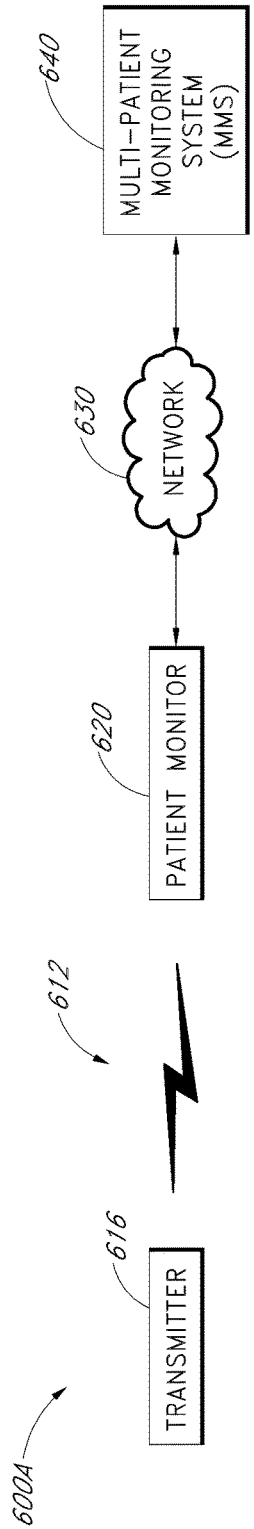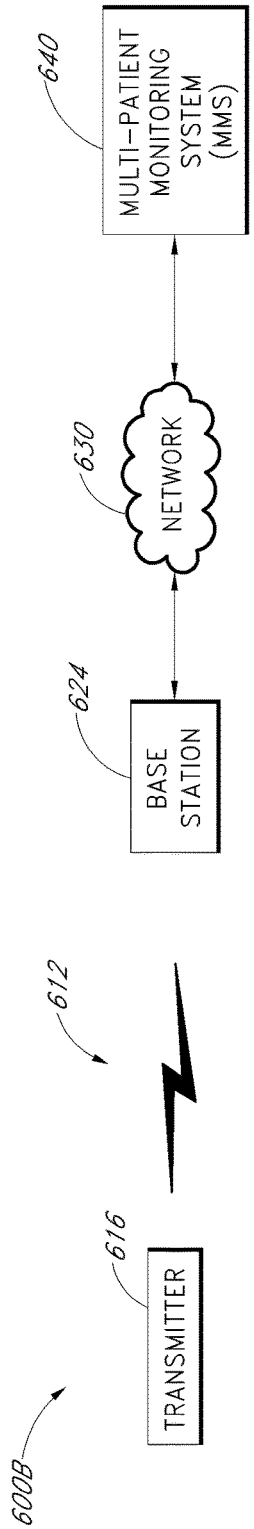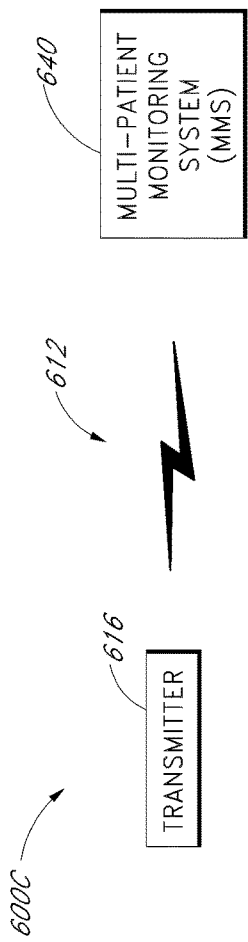
FIG. 6A
FIG. 6B
FIG. 6C

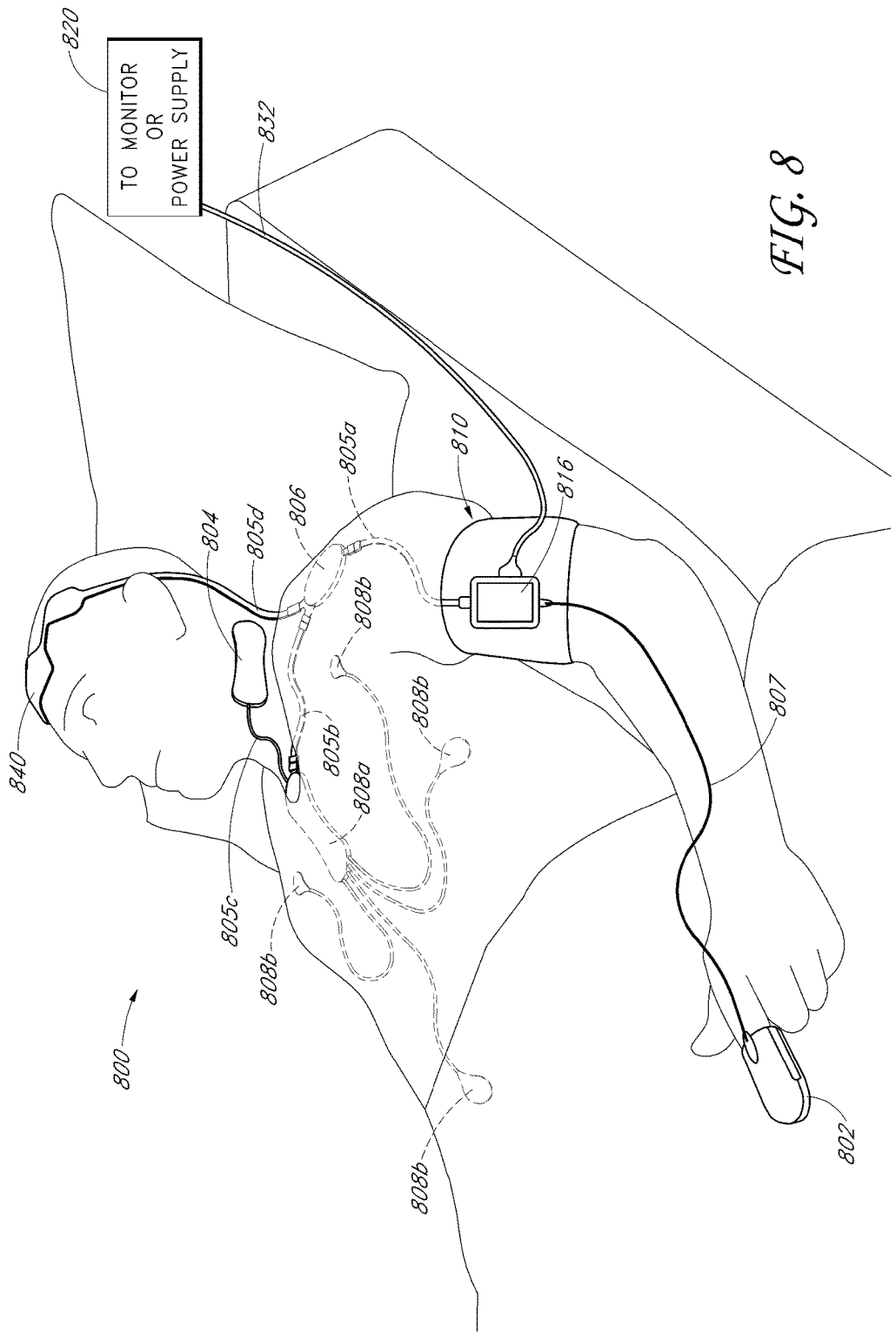

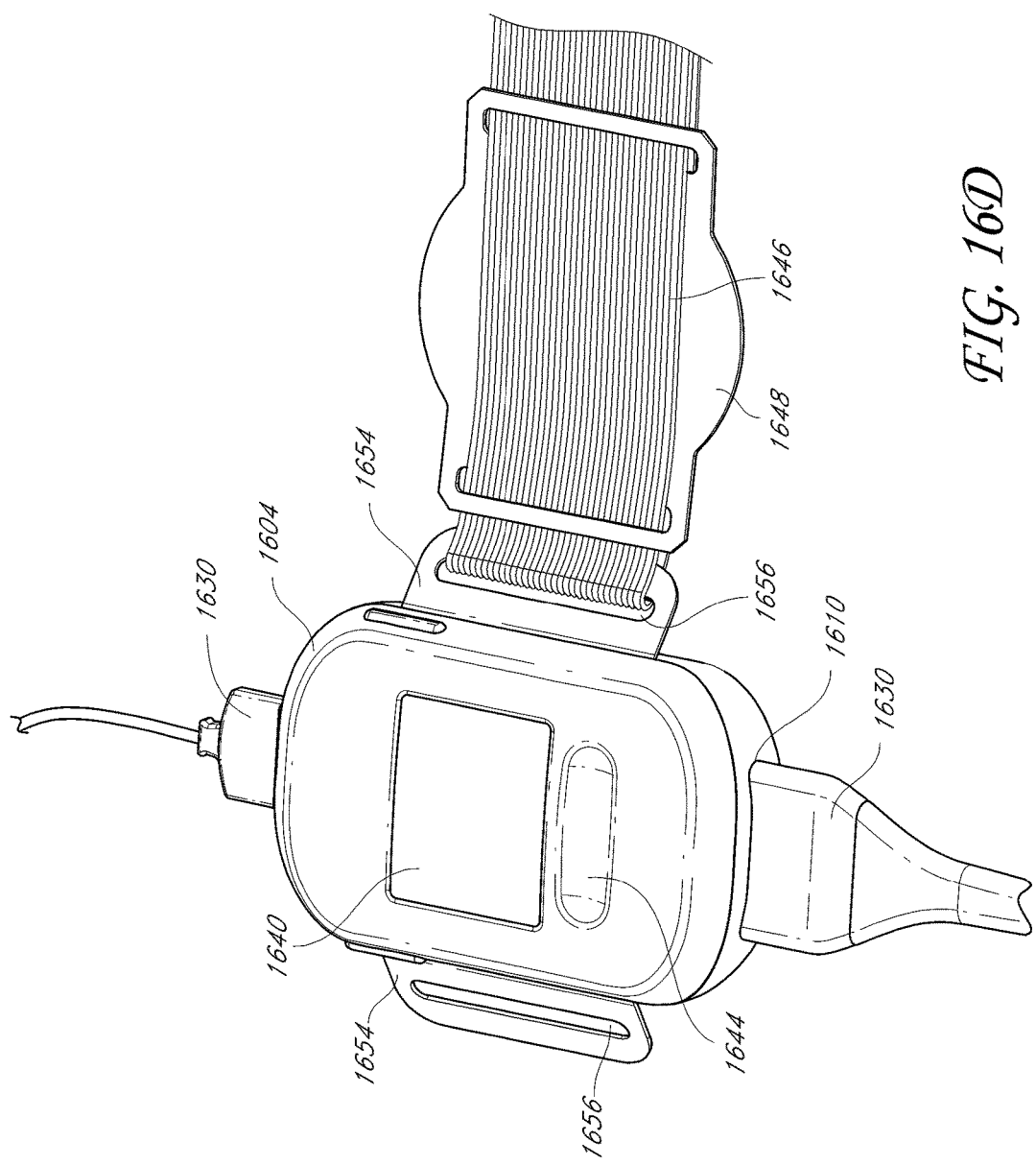

PATIENT POSITION DETECTION SYSTEM

RELATED APPLICATIONS

The present application claims priority to U.S. Provisional Patent Application Ser. No. 61/889,939, filed Oct. 11, 2013, titled Patient Position Detection System, and is a continuation-in-part of U.S. patent application Ser. No. 13/762,270, filed Feb. 7, 2013, titled Wireless Patient Monitoring Device, which claims priority as a non-provisional of U.S. Provisional Patent Application Ser. No. 61/597,126, filed Feb. 9, 2012, titled Wireless Patient Monitoring System, U.S. Provisional Patent Application Ser. No. 61/625,584, filed Apr. 17, 2012, titled Wireless Patient Monitoring Device, and U.S. Provisional Patent Application Ser. No. 61/703,713, filed Sep. 20, 2012, titled Wireless Patient Monitoring Device. All of the foregoing applications are hereby incorporated by reference in their entirety.

BACKGROUND

Hospitals, nursing homes, and other patient care facilities typically include patient monitoring devices at one or more bedsides in the facility. Patient monitoring devices generally include sensors, processing equipment, and displays for obtaining and analyzing a medical patient's physiological parameters such as blood oxygen saturation level, respiratory rate, and the like. Clinicians, including doctors, nurses, and other medical personnel, use the physiological parameters obtained from patient monitors to diagnose illnesses and to prescribe treatments. Clinicians also use the physiological parameters to monitor patients during various clinical situations to determine whether to increase the level of medical care given to patients.

For example, the patient monitoring devices can be used to monitor a pulse oximeter. Pulse oximetry is a widely accepted noninvasive procedure for measuring the oxygen saturation level of arterial blood, an indicator of a person's oxygen supply. A typical pulse oximetry system utilizes an optical sensor clipped onto a fingertip to measure the relative volume of oxygenated hemoglobin in pulsatile arterial blood flowing within the fingertip. Oxygen saturation ($SpO_2$), pulse rate, a plethysmograph waveform, perfusion index (PI), pleth variability index (PVI), methemoglobin (MetHb), carboxyhemoglobin (CoHb), total hemoglobin (tHb), glucose, and/or otherwise can be displayed on a monitor accordingly.

The patient monitoring devices can also communicate with an acoustic sensor comprising an acoustic transducer, such as a piezoelectric element. The acoustic sensor can detect respiratory and other biological sounds of a patient and provide signals reflecting these sounds to a patient monitor. An example of such an acoustic sensor, which can implement any of the acoustic sensing functions described herein, is described in U.S. application Ser. No. 12/643,939, filed Dec. 21, 2009, titled "Acoustic Sensor Assembly," and in U.S. Application No. 61/313,645, filed Mar. 12, 2010, titled "Acoustic Respiratory Monitoring Sensor Having Multiple Sensing Elements," the disclosures of which are hereby incorporated by reference in their entirety.

Blood pressure is another example of a physiological parameter that can be monitored. Many devices allow blood pressure to be measured by sphygmomanometer systems that utilize an inflatable cuff applied to a person's arm. The cuff is inflated to a pressure level high enough to occlude a major artery. When air is slowly released from the cuff, blood pressure can be estimated by detecting "Korotkoff" sounds using a stethoscope or other detection means placed over the artery. Other Examples of physiological parameters that can be measured include respiration rate, blood analyte measurements, such as oxygen saturation, and ECG.

SUMMARY

One aspect of the disclosure is a wireless patient monitoring device including one or more sensors configured to obtain physiological information. The one or more sensors can include an optical sensor, an acoustic respiratory sensor, and/or a blood pressure measurement device. Other sensors, including but not limited to, an EEG, ECG, and/or a sedation state sensor can also be used with the present disclosure. The one or more sensors are connected to a wireless monitor configured to receive the sensor data and to wirelessly transmit sensor data or physiological parameters reflective of the sensor data to a bedside monitor. The bedside monitor can be configured to output the physiological parameters, communication channel, and/or communication status.

Another aspect of the disclosure is directed toward a system configured to wirelessly communicate physiological information, the system including a battery, a housing, a rechargeable electrical storage module, and a memory module configured to store wireless communication information.

In some aspects of the disclosure, the wireless communication information stored on the data storage component facilitates communication between the wireless monitor and the bedside monitor. The information may be a unique identifier used to pair the wireless monitor with the bedside monitor. The information may be a password used to make sure only the correct receiver has access to the transmitted physiological data. The information may be channel information to make certain the wireless monitor and bedside monitor communicate on the same channel.

In some aspects of the disclosure, the bedside monitor can be configured to receive and recharge the removable battery. The battery may include a data storage component configured to store wireless communication information. In some embodiments, the bedside monitor communicates wireless communication information to the battery through a hard wired connection, and the battery stores the information. In some embodiments, the battery communicates wireless communication information to the bedside monitor through a hard wired connection.

Another aspect of the disclosure is directed toward a bedside monitor configured to receive the wireless monitor. In some embodiments, the bedside monitor communicates wireless communication information to the wireless monitor when the wireless monitor is physically and electrically connected with the bedside monitor. In some embodiments, the wireless monitor communicates information to the bedside monitor when the wireless monitor is physically and electrically connected with the bedside monitor.

In another aspect of the disclosure, the wireless monitor can be configured to transmit physiological data over a first wireless technology when a signal strength of the first wireless technology is sufficiently strong and transmit physiological data over a second wireless technology when the signal strength of the first wireless technology is not sufficiently strong.

In yet another aspect of the disclosure, the wireless monitor can be configured to transmit physiological data over a first wireless technology when the wireless monitor is within a pre-determined distance from the wireless receiver and transmit physiological data over a second wireless technology when the wireless monitor is not within a pre-determined distance from the bedside monitor.

In another aspect of the disclosure, the battery includes a display. The display can be configured to activate when the wireless transmitter transmits physiological data over a first wireless technology and deactivate when the wireless transmitter transmits physiological data over a second wireless technology.

One aspect of the disclosure is a method of wirelessly monitoring physiological information. The method includes providing a battery including a data storage component, physically connecting the battery to a bedside monitor, storing data on the data storage component of the battery, connecting the battery to a wireless monitor, and transmitting physiological data from the wireless monitor to the bedside monitor.

In another aspect of the disclosure, transmitting physiological data from the wireless monitor to the bedside monitor includes transmitting physiological data over a first wireless technology when the wireless monitor is within a pre-determined distance from the bedside monitor and transmitting physiological data over a second wireless technology when the wireless monitor is not within a pre-determined distance from the bedside monitor. In some embodiments of the disclosure, the first wireless technology is Bluetooth or ZigBee, and the second wireless technology is Wi-Fi or cellular telephony.

In yet another aspect of the disclosure, transmitting physiological data from the wireless monitor to the bedside monitor includes transmitting physiological data over a first wireless technology when a signal strength of the first wireless technology is sufficiently strong and transmitting physiological data over a second wireless technology when the signal strength of the first wireless technology is not sufficiently strong.

In some aspects of the disclosure, the wireless monitor can be configured to be coupled to an arm band attached to the patient. Alternatively, the wireless monitor can be configured to be coupled to a patient's belt, can be carried by the patient (e.g., via a shoulder strap or handle), or can be placed on the patient's bed next to the patient, among other locations.

In another aspect of the disclosure, the wireless monitor battery includes a display screen. When the wireless monitor is within a pre-determined distance from the bedside monitor and transmits data over Bluetooth or Zigbee, the display screen deactivates. When the wireless monitor is not within a pre-determined distance from the bedside monitor and transmits data over Wi-Fi or cellular telephony, the display screen activates. Alternatively, independent of the communication protocol used by the device, when the wireless monitor is a pre-determined distance from the bedside monitor, the display screen activates. Similarly when the wireless monitor is within a pre-determined distance to the bedside monitor, the display screen deactivates.

In certain aspects of the disclosure, a blood pressure device can be used. The blood pressure device can be coupled to a medical patient and a wireless transceiver electrically coupled with the blood pressure device. The wireless transceiver can wirelessly transmit blood pressure data received by the blood pressure device and physiological data received from one or more physiological sensors coupled to the blood pressure device. To further increase patient mobility, in some embodiments, a single cable can be provided for connecting multiple different types of sensors together.

In certain aspects of the disclosure, a wireless patient monitoring device for measuring one or more parameters can be secured to an arm of the patient. For example, a wireless measurement device for measuring oxygen saturation and respiration rate can be secured to the arm of a patient. The wireless monitoring device can connect to an oximeter probe and an acoustic respiration probe. The monitor can have a display screen and/or can transmit wireless information to a bedside monitor. In an embodiment, a docking station can be provided for the wireless monitoring device to dock it to a docking station forming a bedside monitor.

In some aspects of the disclosure, the patient monitoring devices can be coupled to a blood pressure cuff and measure blood pressure.

In some aspects of the disclosure, the patient monitoring system can include a sensor configured to obtain physiological information, an anchor connected to the sensor, and a wireless transceiver connected to the anchor. A first cable can connect the sensor to the anchor and a second cable can connect the anchor to the wireless transceiver. In certain aspects, the anchor can adhere to the patient or be carried by the patient in any manner discussed herein.

In some aspects of the disclosure, the patient monitoring system can include one or more sensors configured to obtain physiological information and a wireless transceiver configured to receive the physiological information. The wireless transceiver can include a housing having a first side and a second side. At least one connector can be positioned on the first side and at least one connector can be positioned on the second side. In certain aspects, the first side of housing can be opposite the second side of the housing.

In some aspects of the disclosure, a docking station can include a bedside monitor having a docking port configured to receive a first patient monitor and a docking station adapter configured to adapt the docking port to receive a second patient monitor. The second patient monitor can be a different size than the first patient monitor. In certain aspects, the first patient monitor can communicate with the bedside monitor over a wired connection when the first patient monitor is connected to the docking port. In certain aspects, the second patient monitor can communicate with the bedside monitor over a wired connection when the second patient monitor is connected to the docking station adapter and the docking station adapter is connected to the docking port.

In some aspects of the disclosure, a patient monitoring system can include a first sensor, a second sensor, and a wireless patient monitor configured to receive physiological information from the first sensor and the second sensor. The patient monitoring system can include a single cable connecting the first sensor and the second sensor to the wireless patient monitor. In certain aspects, the single cable can include a first cable section connecting the wireless patient monitor and the first sensor and a second cable section connecting the first sensor and the second sensor. In certain aspects, the first sensor and the second sensor can be powered by a shared power line and/or can transmit signals over a shared signal line.

In some aspects of the disclosure, a patient monitoring system can include one or more sensors configured to obtain physiological information, a patient monitor configured to receive the physiological information, and a cable hub having one or more inlet connectors connected to the one or more sensors and an outlet connector connected to the patient monitor. In certain aspects, the one or more inlet connectors can be positioned on a first end of the cable hub and the outlet connector can be positioned on a second end of the cable hub, opposite the first end. In certain aspects, the patient monitor can include a wireless transceiver. In certain aspects, the patient monitor can be configured to be worn by the patient. In certain aspects, the cable hub can be configured to adhere to the patient. In certain aspects, a first cable extends from at least one of the one or more sensors to one of the one or more inlet connectors, and a second cable extends from the outlet connector to the patient monitor.

Some aspects of the disclosure describe a method of using a patient monitoring system. The method can include providing a wireless transceiver having a first end and a second end opposite the first end, a first connector positioned on the first end, and a second connector positioned on the second end. The method can include connecting a first end of a first cable to the first connector, and connecting a first end of a second cable to the second connector. In certain aspects, the method can include connecting a second end of the first cable to a first sensor. In certain aspects, the method can include connecting a second end of the second cable to a second sensor or a cable hub connected to one or more sensors. In certain aspects, the method can include connecting a third sensor and/or anchor to the second cable. In certain aspects, the method can include connecting a third cable to a third connector on the second end of the wireless transceiver.

Certain aspects of this disclosure are directed toward a wireless monitor including a housing, a battery, and a strap. The housing can include one or more outlets configured to receive one or more sensors. The battery can be configured to removably engage the housing. A portion of the strap can be disposed between the housing and the battery when the housing is engaged with the battery. In certain aspects, the portion of the strap disposed between the housing and the battery can be a separately formed component from a remainder of the strap. In certain aspects, the portion of the strap can include one or more mating features configured to mate with corresponding features of the housing. In certain aspects, the one or more mating features are flush with the corresponding features of the housing. In certain aspects, the housing can include a recessed portion for receiving the strap.

For purposes of summarizing the disclosure, certain aspects, advantages and novel features of the inventions have been described herein. It is to be understood that not necessarily all such advantages can be achieved in accordance with any particular embodiment of the inventions disclosed herein. Thus, the inventions disclosed herein can be embodied or carried out in a manner that achieves or optimizes one advantage or group of advantages as taught herein without necessarily achieving other advantages as can be taught or suggested herein.

BRIEF DESCRIPTION OF THE DRAWINGS

Various embodiments will be described hereinafter with reference to the accompanying drawings. These embodiments are illustrated and described by example only, and are not intended to limit the scope of the disclosure. In the drawings, similar elements have similar reference numerals.

FIGS. 1A and 1B illustrate embodiments of wireless patient monitoring systems.

FIGS. 1C and 1D illustrate further embodiments of wireless patient monitoring systems.

FIGS. 2A and 2B illustrate embodiments of wireless patient monitoring systems having a single cable connection system.

FIGS. 6A through 6C illustrate additional embodiments of patient monitoring systems.

FIG. 8 illustrates a further embodiment of a patient monitoring system.

FIGS. 16A-16G illustrate another embodiment of a wireless patient monitoring system.

DETAILED DESCRIPTION

I. Introduction

Figure 1D:
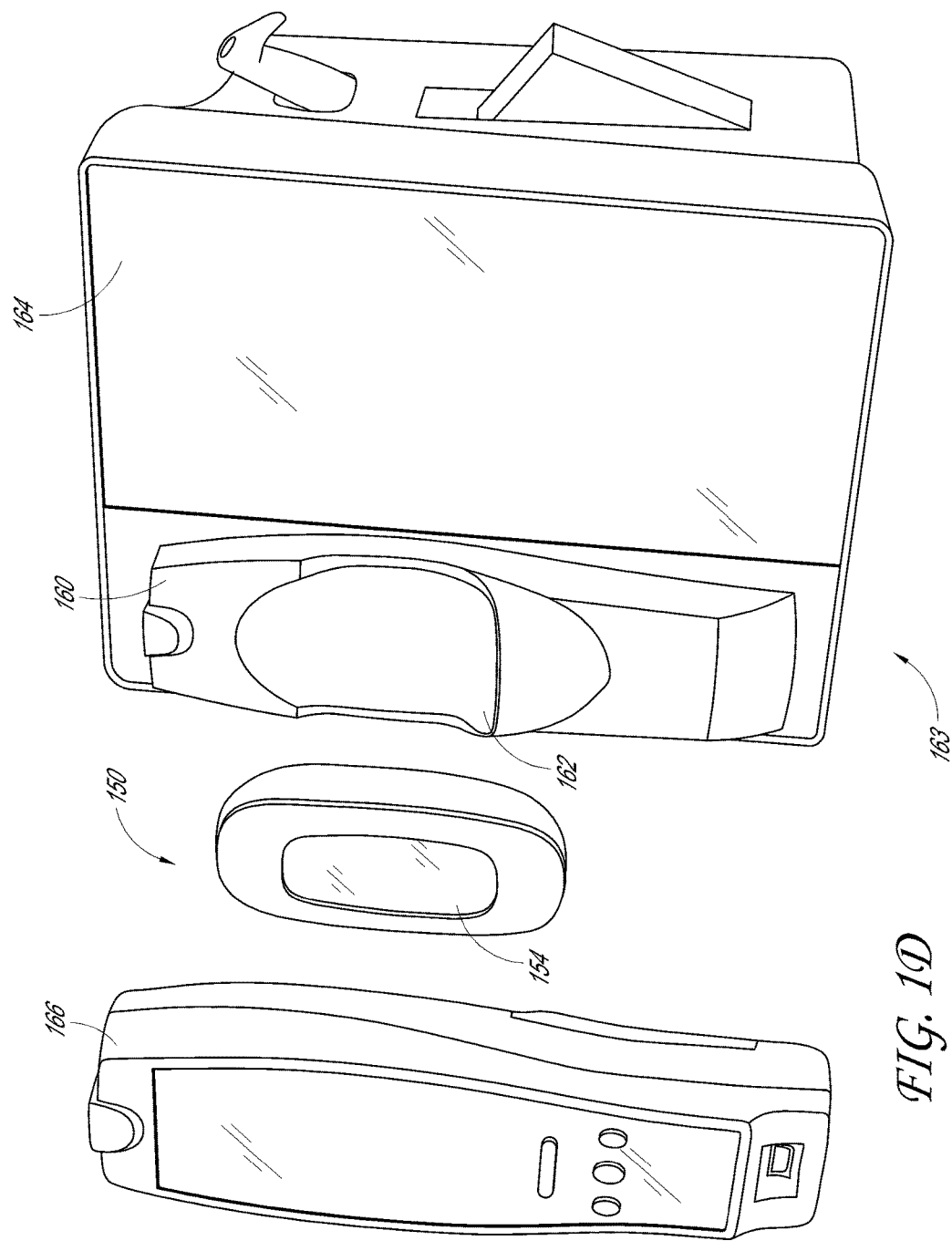

In clinical settings, medical sensors are often attached to patients to monitor physiological parameters of the patients. Some examples of medical sensors include, but are not limited to, blood oxygen sensors, such as pulse oximetry sensors, acoustic respiratory sensors, EEGs, ECGs, blood pressure sensors, sedation state sensors, etc. Typically, each sensor attached to a patient is connected to a bedside monitoring device with a cable. The cables limit the patient's freedom of movement and impede a care providers access to the patient. The cables connecting the patient to the bedside monitoring device also make it more difficult to move the patient from room to room or switch to different bedside monitors.

This disclosure describes embodiments of wireless patient monitoring systems that include a wireless device coupled to a patient and to one or more sensors. In one embodiment, the wireless device transmits sensor data obtained from the sensors to a patient monitor. By transmitting the sensor data wirelessly, these patient monitoring systems can advantageously replace some or all cables that connect patients to bedside monitoring devices. To further increase patient mobility and comfort, in some embodiments, a single cable connection system is also provided for connecting multiple different types of sensors together.

These patient monitoring systems are primarily described in the context of an example blood pressure cuff that includes a wireless transceiver. The blood pressure cuff and/or wireless transceiver can also be coupled to additional sensors, such as optical sensors, acoustic sensors, and/or electrocardiograph sensors. The wireless transceiver can transmit blood pressure data and sensor data from the other sensors to a wireless receiver, which can be a patient monitor. These and other features described herein can be applied to a variety of sensor configurations, including configurations that do not include a blood pressure cuff. In an embodiment, an arm band without a blood pressure cuff can be used to secure a wireless patient monitor connected to various sensors.

II. Example Embodiments

FIGS. 1A and 1B illustrate embodiments of wireless patient monitoring systems 100A, 100B, respectively. In the wireless patient monitoring systems 100 shown, a blood pressure device 110 is connected to a patient 101. The blood pressure device 110 includes a wireless transceiver 116, which can transmit sensor data obtained from the patient 101 to a wireless transceiver 120. Thus, the patient 101 is advantageously not physically coupled to a bedside monitor in the depicted embodiment and can therefore have greater freedom of movement.

Referring to FIG. 1A, the blood pressure device 110a includes an inflatable cuff 112, which can be an oscillometric cuff that is actuated electronically (e.g., via intelligent cuff inflation and/or based on a time interval) to obtain blood pressure information. The cuff 112 is coupled to a wireless transceiver 116. The blood pressure device 110a is also coupled to a fingertip optical sensor 102 via a cable 107. The optical sensor 102 can include one or more emitters and detectors for obtaining physiological information indicative of one or more blood parameters of the patient 101. These parameters can include various blood analytes such as oxygen, carbon monoxide, methemoglobin, total hemoglobin, glucose, proteins, glucose, lipids, a percentage thereof (e.g., concentration or saturation), and the like. The optical sensor 102 can also be used to obtain a photoplethysmograph, a measure of plethysmograph variability, pulse rate, a measure of blood perfusion, and the like.

Additionally, the blood pressure device 110a is coupled to an acoustic sensor 104a via a cable 105. The cable 105 connecting the acoustic sensor 104a to the blood pressure device 110 includes two portions, namely a cable 105a and a cable 105b. The cable 105a connects the acoustic sensor 104a to an anchor 104b, which is coupled to the blood pressure device 110a via the cable 105b. The anchor 104b can be adhered to the patient's skin to reduce noise due to accidental tugging of the acoustic sensor 104a.

The acoustic sensor 104a can be a piezoelectric sensor or the like that obtains physiological information reflective of one or more respiratory parameters of the patient 101. These parameters can include, for example, respiratory rate, inspiratory time, expiratory time, inspiration-to-expiration ratio, inspiratory flow, expiratory flow, tidal volume, minute volume, apnea duration, breath sounds, rales, rhonchi, stridor, and changes in breath sounds such as decreased volume or change in airflow. In addition, in some cases the respiratory sensor 104a, or another lead of the respiratory sensor 104a (not shown), can measure other physiological sounds such as heart rate (e.g., to help with probe-off detection), heart sounds (e.g., S1, S2, S3, S4, and murmurs), and changes in heart sounds such as normal to murmur or split heart sounds indicating fluid overload. In some implementations, a second acoustic respiratory sensor can be provided over the patient's 101 chest for additional heart sound detection. In one embodiment, the acoustic sensor 104 can include any of the features described in U.S. patent application Ser. No. 12/643,939, filed Dec. 21, 2009, titled "Acoustic Sensor Assembly," the disclosure of which is hereby incorporated by reference in its entirety.

The acoustic sensor 104 can be used to generate an exciter waveform that can be detected by the optical sensor 102 at the fingertip, by an optical sensor attached to an ear of the patient (see FIGS. 2A, 3), by an ECG sensor (see FIG. 2C), or by another acoustic sensor (not shown). The velocity of the exciter waveform can be calculated by a processor (such as a processor in the wireless transceiver 120, described below). From this velocity, the processor can derive a blood pressure measurement or blood pressure estimate. The processor can output the blood pressure measurement for display. The processor can also use the blood pressure measurement to determine whether to trigger the blood pressure cuff 112.

In another embodiment, the acoustic sensor 104 placed on the upper chest can be advantageously combined with an ECG electrode (such as in structure 208 of FIG. 2B), thereby providing dual benefit of two signals generated from a single mechanical assembly. The timing relationship from fidicial markers from the ECG signal, related cardiac acoustic signal and the resulting peripheral pulse from the finger pulse oximeters produces a transit time that correlates to the cardiovascular performance such as blood pressure, vascular tone, vascular volume and cardiac mechanical function. Pulse wave transit time or PWTT in currently available systems depends on ECG as the sole reference point, but such systems may not be able to isolate the transit time variables associated to cardiac functions, such as the pre-ejection period (PEP). In certain embodiments, the addition of the cardiac acoustical signal allows isolation of the cardiac functions and provides additional cardiac performance metrics. Timing calculations can be performed by the processor in the wireless transceiver 120 or a in distributed processor found in an on-body structure (e.g., such as any of the devices herein or below: 112, 210, 230, 402, 806).

In certain embodiments, the wireless patient monitoring system 100 uses some or all of the velocity-based blood pressure measurement techniques described in U.S. Pat. No. 5,590,649, filed Apr. 15, 1994, titled "Apparatus and Method for Measuring an Induced Perturbation to Determine Blood Pressure," or in U.S. Pat. No. 5,785,659, filed Jan. 17, 1996, titled "Automatically Activated Blood Pressure Measurement Device," the disclosures of which are hereby incorporated by reference in their entirety. An example display related to such blood pressure calculations is described below with respect to FIG. 7.

The wireless transceiver 116 can transmit data using any of a variety of wireless technologies, such as Wi-Fi (802.11x), Bluetooth (802.15.2), Zigbee (802.15.4), cellular telephony, infrared, RFID, satellite transmission, proprietary protocols, combinations of the same, and the like. The wireless transceiver 116 can perform solely telemetry functions, such as measuring and reporting information about the patient 101. Alternatively, the wireless transceiver 116 can be a transceiver that also receives data and/or instructions, as will be described in further detail below.

The wireless receiver 120 receives information from and/or sends information to the wireless transceiver via an antenna 122. In certain embodiments, the wireless receiver 120 is a patient monitor. As such, the wireless receiver 120 can include one or more processors that process sensor signals received from the wireless transceiver 116 corresponding to the sensors 102a, 102b, 104, and/or 106 in order to derive any of the physiological parameters described above. The wireless transceiver 120 can also display any of these parameters, including trends, waveforms, related alarms, and the like. The wireless receiver 120 can further include a computer-readable storage medium, such as a physical storage device, for storing the physiological data. The wireless transceiver 120 can also include a network interface for communicating the physiological data to one or more hosts over a network, such as to a nurse's station computer in a hospital network.

Moreover, in certain embodiments, the wireless transceiver 116 can send raw data for processing to a central nurse's station computer, to a clinician device, and/or to a bedside device (e.g., the receiver 116). The wireless transceiver 116 can also send raw data to a central nurse's station computer, clinician device, and/or to a bedside device for calculation, which retransmits calculated measurements back to the blood pressure device 110 (or to the bedside device). The wireless transceiver 116 can also calculate measurements from the raw data and send the measurements to a central nurse's station computer, to a pager or other clinician device, or to a bedside device (e.g., the receiver 116). Many other configurations of data transmission are possible.

In addition to deriving any of the parameters mentioned above from the data obtained from the sensors 102a, 102b, 104, and/or 106, the wireless transceiver 120 can also determine various measures of data confidence, such as the data confidence indicators described in U.S. Pat. No. 7,024,233 entitled "Pulse oximetry data confidence indicator," the disclosure of which is hereby incorporated by reference in its entirety. The wireless transceiver 120 can also determine a perfusion index, such as the perfusion index described in U.S. Pat. No. 7,292,883 entitled "Physiological assessment system," the disclosure of which is hereby incorporated by reference in its entirety. Moreover, the wireless transceiver 120 can determine a plethysmograph variability index (PVI), such as the PVI described in U.S. Publication No. 2008/0188760 entitled "Plethysmograph variability processor," the disclosure of which is hereby incorporated by reference in its entirety.

In addition, the wireless transceiver 120 can send data and instructions to the wireless transceiver 116 in some embodiments. For instance, the wireless transceiver 120 can intelligently determine when to inflate the cuff 112 and can send inflation signals to the transceiver 116. Similarly, the wireless transceiver 120 can remotely control any other sensors that can be attached to the transceiver 116 or the cuff 112. The transceiver 120 can send software or firmware updates to the transceiver 116. Moreover, the transceiver 120 (or the transceiver 116) can adjust the amount of signal data transmitted by the transceiver 116 based at least in part on the acuity of the patient, using, for example, any of the techniques described in U.S. Patent Publication No. 2009/0119330, filed Jan. 7, 2009, titled "Systems and Methods for Storing, Analyzing, and Retrieving Medical Data," the disclosure of which is hereby incorporated by reference in its entirety.

In alternative embodiments, the wireless transceiver 116 can perform some or all of the patient monitor functions described above, instead of or in addition to the monitoring functions described above with respect to the wireless transceiver 120. In some cases, the wireless transceiver 116 might also include a display that outputs data reflecting any of the parameters described above (see, e.g., FIG. 5). Thus, the wireless transceiver 116 can either send raw signal data to be processed by the wireless transceiver 120, can send processed signal data to be displayed and/or passed on by the wireless transceiver 120, or can perform some combination of the above. Moreover, in some implementations, the wireless transceiver 116 can perform at least some front-end processing of the data, such as bandpass filtering, analog-to-digital conversion, and/or signal conditioning, prior to sending the data to the transceiver 120. An alternative embodiment may include at least some front end processing embedded in any of the sensors described herein (such as sensors 102, 104, 204, 202, 208, 412, 804, 840, 808) or cable hub 806 (see FIG. 8).

In certain embodiments, the cuff 112 is a reusable, disposable, or resposable device. Similarly, any of the sensors 102, 104a or cables 105, 107 can be disposable or resposable. Resposable devices can include devices that are partially disposable and partially reusable. Thus, for example, the acoustic sensor 104a can include reusable electronics but a disposable contact surface (such as an adhesive) where the sensor 104a comes into contact with the patient's skin. Generally, any of the sensors, cuffs, and cables described herein can be reusable, disposable, or resposable.

The cuff 112 can also can have its own power (e.g., via batteries) either as extra power or as a sole source of power for the transceiver 116. The batteries can be disposable or reusable. In some embodiments, the cuff 112 can include one or more photovoltaic solar cells or other power sources. Likewise, batteries, solar sources, or other power sources can be provided for either of the sensors 102, 104a.

Referring to FIG. 1B, another embodiment of the system 100B is shown. In the system 100B, the blood pressure device 110b can communicate wirelessly with the acoustic sensor 104a and with the optical sensor 102. For instance, wireless transceivers (not shown) can be provided in one or both of the sensors 102, 104a, using any of the wireless technologies described above. The wireless transceivers can transmit data using any of a variety of wireless technologies, such as Wi-Fi (802.11x), Bluetooth (802.15.2), Zigbee (802.15.4), cellular telephony, infrared, RFID, satellite transmission, proprietary protocols, combinations of the same, and the like. The wireless transceivers can transmit data, raw signals, processed signals, conditioned signals, or the like to the blood pressure device 110b. The blood pressure device 110b can transmit these signals on to the wireless transceiver 120. In addition, in some embodiments, the blood pressure device 110b can also process the signals received from the sensors 102, 104a prior to transmitting the signals to the wireless transceiver 120. The sensors 102, 104a can also transmit data, raw signals, processed signals, conditioned signals, or the like directly to the wireless transceiver 120 or patient monitor. In one embodiment, the system 100B shown can be considered to be a body LAN, piconet, or other individual network.

FIGS. 1C and 1D illustrate another embodiment in which a wireless monitor 150 is secured to the arm of the patient. The wireless monitor 150 is a fully functional stand-alone monitor capable of various physiological measurements. The wireless monitor is small and light enough to comfortably be secured to and carried around on the arm of a patient. In the embodiment shown in FIG. 1C, the wireless monitor 150 connects to an acoustic respiration sensor 104A on a first side of patient monitor 150 and an oximeter sensor 102 on a second side of patient monitor 150. This configuration of connected sensors to opposite sides of the monitor prevents cable clutter and entanglements. The wireless monitor 150 includes a screen 154. The wireless monitor 150 couples to and is held to the arm of the patient by arm band 152. In FIG. 1C, the arm band is not an inflatable blood pressure cuff, however, as described with respect to the other figures, the arm band 152 can incorporate a blood pressure cuff for blood pressure readings.

The wireless monitor 150 can transmit data to a bedside monitor using any of a variety of wireless technologies, such as Wi-Fi (802.11x), Bluetooth (802.15.2), Zigbee (802.15.4), cellular telephony, infrared, RFID, satellite transmission, proprietary protocols, combinations of the same, and the like.

In an embodiment shown in FIG. 1D, the monitor 150 can be docked to a docking station 163. The docking station 163 includes a bedside monitor 164 and docking station adapter 160. Docking station adapter 160 adapts an otherwise incompatible docking port of bedside monitor 164 so that patient monitor 150 can dock. The docking station adapter 162 includes a port 162 for docking with the patient monitor 150. When the patient monitor 150 is physically docked in the docking station adapter 160, the patient monitor 150 can communicate with the bedside monitor 164 over a wired connection.

Also shown in FIG. 1D is handheld patient monitor 166. Handheld monitor 166 is configured to dock directly to bedside monitor 164 without the need for a docking station adapter 162. When the handheld monitor 166 is physically docked in the bedside monitor 164, the handheld monitor 166 can communicate with the bedside monitor 164 over a wired connection.

Figure 1E:
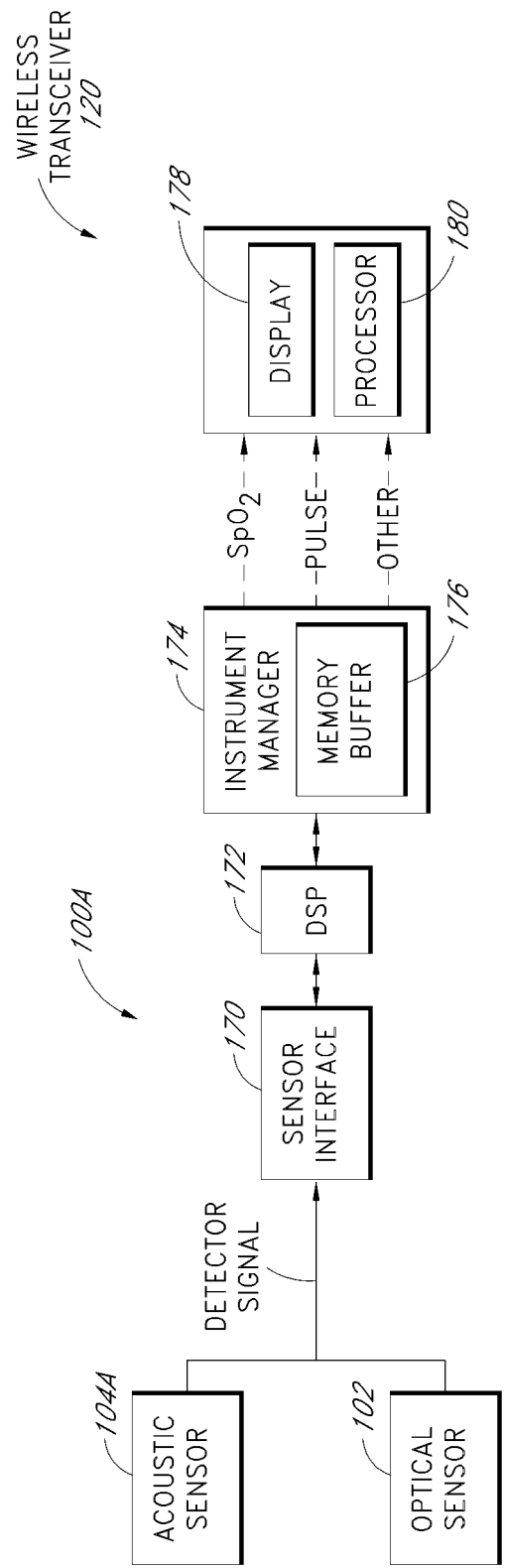
FIG. 1E illustrates the embodiment of the wireless patient monitoring system illustrated in FIGS. 1A-1B in schematic form.

FIG. 1E illustrates details of an embodiment of the wireless monitoring system 100A in a schematic form. Although other types of sensors can be used, the wireless monitoring system 100A is drawn in connection with the acoustic sensor 104a and the optical sensor 102. The system 100A sends signals from the acoustic sensor 104a and the optical sensor 102 to the sensor interface 170 and passes the signals to the DSP 172 for processing into representations of physiological parameters. In some embodiments, the DSP also communicates with a memory or information element, such as a resistor or capacitor, located on one of the sensors, such memory typically contains information related to the properties of the sensor that may be useful in processing the signals, such as, for example, emitter energy wavelengths.

In some embodiments, the physiological parameters are passed to an instrument manager 174, which may further process the parameters for display. The instrument manager 174 may include a memory buffer 176 to maintain this data for processing throughout a period of time. Memory buffer 176 may include RAM, Flash or other solid state memory, magnetic or optical disk-based memories, combinations of the same or the like.

The wireless transceiver 120 is capable of wirelessly receiving the physiological data and/or parameters from DSP 172 or instrument manager 174. The bedside monitor 916 can include one or more displays 178, control buttons, a speaker for audio messages, and/or a wireless signal broadcaster. The wireless transceiver 120 can also include a processor 180 to further process the data and/or parameters for display.

Figure 2B:
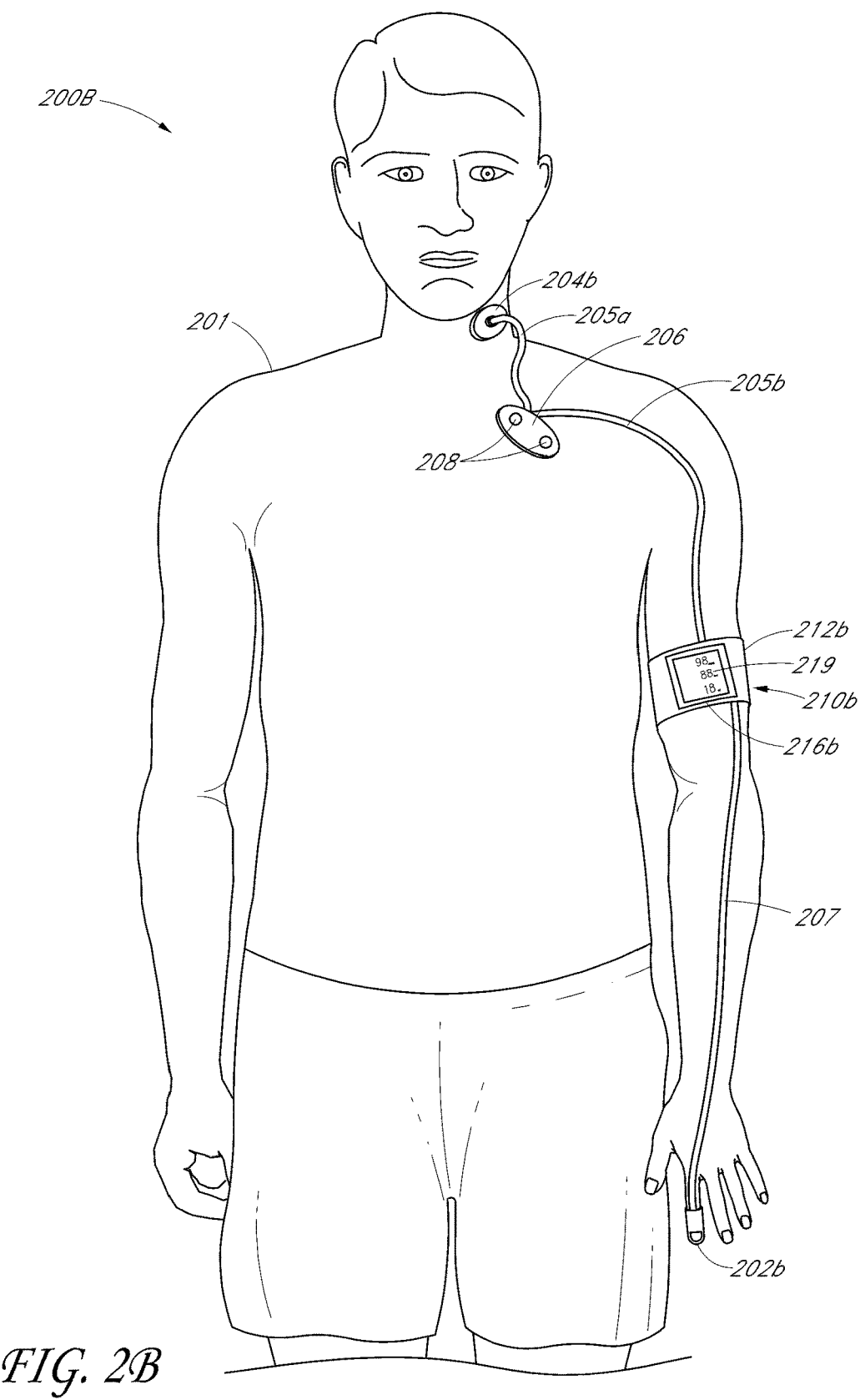

FIGS. 2A and 2B illustrate additional embodiments of patient monitoring systems 200A and 200B, respectively. In particular, FIG. 2A illustrates a wireless patient monitoring system 200A, while FIG. 2B illustrates a standalone patient monitoring system 200B.

Referring specifically to FIG. 2A, a blood pressure device 210a is connected to a patient 201. The blood pressure device 210a includes a wireless transceiver 216a, which can transmit sensor data obtained from the patient 201 to a wireless receiver at 220 via antenna 218. The wireless transceiver 216a can transmit data using any of a variety of wireless technologies, such as Wi-Fi (802.11x), Bluetooth (802.15.2), Zigbee (802.15.4), cellular telephony, infrared, RFID, satellite transmission, proprietary protocols, combinations of the same, and the like.

In the depicted embodiment, the blood pressure device 210a includes an inflatable cuff 212a, which can include any of the features of the cuff 112 described above. Additionally, the cuff 212a includes a pocket 214, which holds the wireless transceiver 216a (shown by dashed lines). The wireless transceiver 216a can be electrically connected to the cuff 212a via a connector (see, e.g., FIG. 5) in some embodiments. As will be described elsewhere herein, the form of attachment of the wireless transceiver 216a to the cuff 212a is not restricted to a pocket connection mechanism and can vary in other implementations.

The wireless transceiver 216a is also coupled to various sensors in FIG. 2A, including an acoustic sensor 204a and/or an optical ear sensor 202a. The acoustic sensor 204a can have any of the features of the acoustic sensor 104 described above. The ear clip sensor 202a can be an optical sensor that obtains physiological information regarding one or more blood parameters of the patient 201. These parameters can include any of the blood-related parameters described above with respect to the optical sensor 102. In one embodiment, the ear clip sensor 202a is an LNOP TC-I ear reusable sensor available from Masimo® Corporation of Irvine, Calif. In some embodiments, the ear clip sensor 202a is a concha ear sensor (see FIGS. 4A and 4B).

Advantageously, in the depicted embodiment, the sensors 202a, 204a are coupled to the wireless transceiver 216a via a single cable 205. The cable 205 is shown having two sections, a cable 205a and a cable 205b. For example, the wireless transceiver 216a is coupled to an acoustic sensor 204a via the cable 205b. In turn, the acoustic sensor 204a is coupled to the optical ear sensor 202a via the cable 205a. Advantageously, because the sensors 202a, 204 are attached to the wireless transceiver 216 in the cuff 212 in the depicted embodiment, the cable 205 is relatively short and can thereby increase the patient's 201 freedom of movement. Moreover, because a single cable 205 is used to connect two or more different types of sensors, such as sensors 202a, 204a, the patient's mobility and comfort can be further enhanced.

In some embodiments, the cable 205 is a shared cable 205 that is shared by the optical ear sensor 202a and the acoustic sensor 204a. The shared cable 205 can share power and ground lines for each of the sensors 202a, 204a. Signal lines in the cable 205 can convey signals from the sensors 202a, 204a to the wireless transceiver 216 and/or instructions from the wireless transceiver 216 to the sensors 202a, 204a. The signal lines can be separate within the cable 205 for the different sensors 202a, 204a. Alternatively, the signal lines can be shared as well, forming an electrical bus.

The two cables 205a, 205a can be part of a single cable or can be separate cables 205a, 205b. As a single cable 205, in one embodiment, the cable 205a, 205b can connect to the acoustic sensor 204a via a single connector. As separate cables, in one embodiment, the cable 205b can be connected to a first port on the acoustic sensor 204a and the cable 205a can be coupled to a second port on the acoustic sensor 204a.

FIG. 2B further illustrates an embodiment of the cable 205 in the context of a standalone patient monitoring system 200B. In the standalone patient monitoring system 200B, a blood pressure device 210b is provided that includes a patient monitor 216b disposed on a cuff 212b. The patient monitor 216b includes a display 219 for outputting physiological parameter measurements, trends, waveforms, patient data, and optionally other data for presentation to a clinician. The display 219 can be an LCD display, for example, with a touch screen or the like. The patient monitor 216b can act as a standalone device, not needing to communicate with other devices to process and measure physiological parameters. In some embodiments, the patient monitor 216b can also include any of the wireless functionality described above. For example, the patient monitor 216b can transmit data using any of a variety of wireless technologies, such as Wi-Fi (802.11x), Bluetooth (802.15.2), Zigbee (802.15.4), cellular telephony, infrared, RFID, satellite transmission, proprietary protocols, combinations of the same, and the like.

The patient monitor 216b can be integrated into the cuff 212b or can be detachable from the cuff 212b. In one embodiment, the patient monitor 216b can be a readily available mobile computing device with a patient monitoring software application. For example, the patient monitor 216b can be a smart phone, personal digital assistant (PDA), or other wireless device. The patient monitoring software application on the device can perform any of a variety of functions, such as calculating physiological parameters, displaying physiological data, documenting physiological data, and/or wirelessly transmitting physiological data (including measurements or uncalculated raw sensor data) via email, text message (e.g., SMS or MMS), or some other communication medium. Moreover, any of the wireless transceivers or patient monitors described herein can be substituted with such a mobile computing device.

In the depicted embodiment, the patient monitor 216b is connected to three different types of sensors. An optical sensor 202b, coupled to a patient's 201 finger, is connected to the patient monitor 216b via a cable 207. In addition, an acoustic sensor 204b and an electrocardiograph (ECG) sensor 206 are attached to the patient monitor 206b via the cable 205. The optical sensor 202b can perform any of the optical sensor functions described above. Likewise, the acoustic sensor 204b can perform any of the acoustic sensor functions described above. The ECG sensor 206 can be used to monitor electrical activity of the patient's 201 heart.

Advantageously, in the depicted embodiment, the ECG sensor 206 is a bundle sensor that includes one or more ECG leads 208 in a single package. For example, the ECG sensor 206 can include one, two, or three or more leads. One or more of the leads 208 can be an active lead or leads, while another lead 208 can be a reference lead. Other configurations are possible with additional leads within the same package or at different points on the patient's body. Using a bundle ECG sensor 206 can advantageously enable a single cable connection via the cable 205 to the cuff 212b. Similarly, an acoustical sensor can be included in the ECG sensor 206 to advantageously reduce the overall complexity of the on-body assembly.

The cable 205a in FIG. 2B can connect two sensors to the cuff 212b, namely the ECG sensor 206 and the acoustic sensor 204b. Although not shown, the cable 205a can further connect an optical ear sensor to the acoustic sensor 204b in some embodiments, optionally replacing the finger optical sensor 202b. The cable 205a shown in FIG. 2B can have all the features described above with respect to cable 205a of FIG. 2A.

Although not shown, in some embodiments, any of the sensors, cuffs, wireless sensors, or patient monitors described herein can include one or more accelerometers or other motion measurement devices (such as gyroscopes). For example, in FIG. 2B, one or more of the acoustic sensor 204b, the ECG sensor 206, the cuff 212b, the patient monitor 216b, and/or the optical sensor 202b can include one or more motion measurement devices. A motion measurement device can be used by a processor (such as in the patient monitor 216b or other device) to determine motion and/or position of a patient. For example, a motion measurement device can be used to determine whether a patient is sitting up, lying down, walking, or the like.

Movement and/or position data obtained from a motion measurement device can be used to adjust a parameter calculation algorithm to compensate for the patient's motion. For example, a parameter measurement algorithm that compensates for motion can more aggressively compensate for motion in response to high degree of measured movement. When less motion is detected, the algorithm can compensate less aggressively. Movement and/or position data can also be used as a contributing factor to adjusting parameter measurements. Blood pressure, for instance, can change during patient motion due to changes in blood flow. If the patient is detected to be moving, the patient's calculated blood pressure (or other parameter) can therefore be adjusted differently than when the patient is detected to be sitting.

A database can be assembled that includes movement and parameter data (raw or measured parameters) for one or more patients over time. The database can be analyzed by a processor to detect trends that can be used to perform parameter calculation adjustments based on motion or position. Many other variations and uses of the motion and/or position data are possible.

Although the patient monitoring systems described herein, including the systems 100A, 100B, 200A, and 200B have been described in the context of blood pressure cuffs, blood pressure need not be measured in some embodiments. For example, the cuff can be a holder for the patient monitoring devices and/or wireless transceivers and not include any blood pressure measuring functionality. Further, the patient monitoring devices and/or wireless transceivers shown need not be coupled to the patient via a cuff, but can be coupled to the patient at any other location, including not at all. For example, the devices can be coupled to the patient's belt (see FIGS. 3A and 3B), can be carried by the patient (e.g., via a shoulder strap or handle), or can be placed on the patient's bed next to the patient, among other possible locations.

Additionally, various features shown in FIGS. 2A and 2B can be changed or omitted. For instance, the wireless transceiver 216 can be attached to the cuff 212 without the use of the pocket 214. For example, the wireless transceiver can be sewn, glued, buttoned or otherwise attached to the cuff using any various known attachment mechanisms. Or, the wireless transceiver 216 can be directly coupled to the patient (e.g., via an armband) and the cuff 212 can be omitted entirely. Instead of a cuff, the wireless transceiver 216 can be coupled to a non-occlusive blood pressure device. Many other configurations are possible.

Figure 3A:
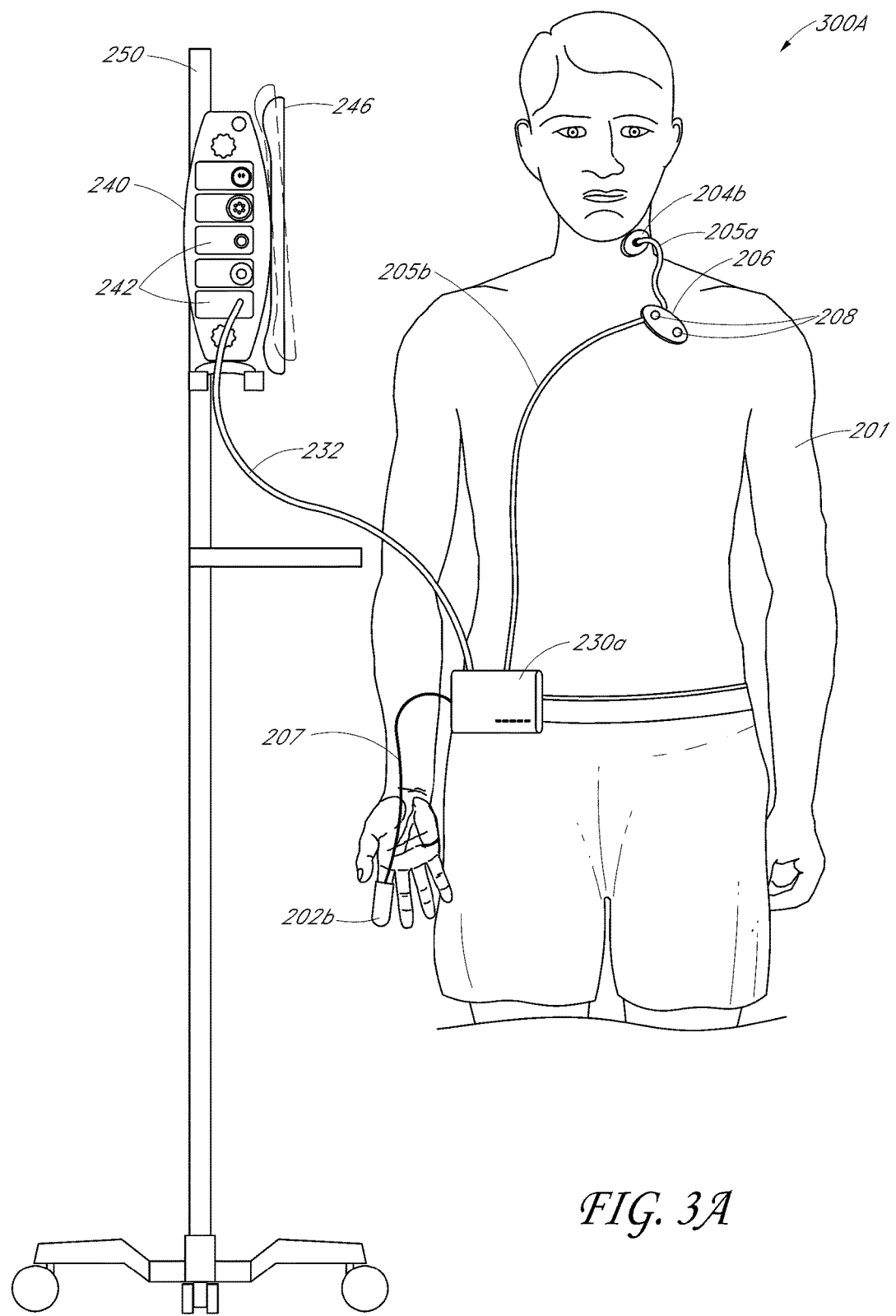
FIGS. 3A and 3B illustrates additional embodiment of patient monitoring systems.
Figure 3B:
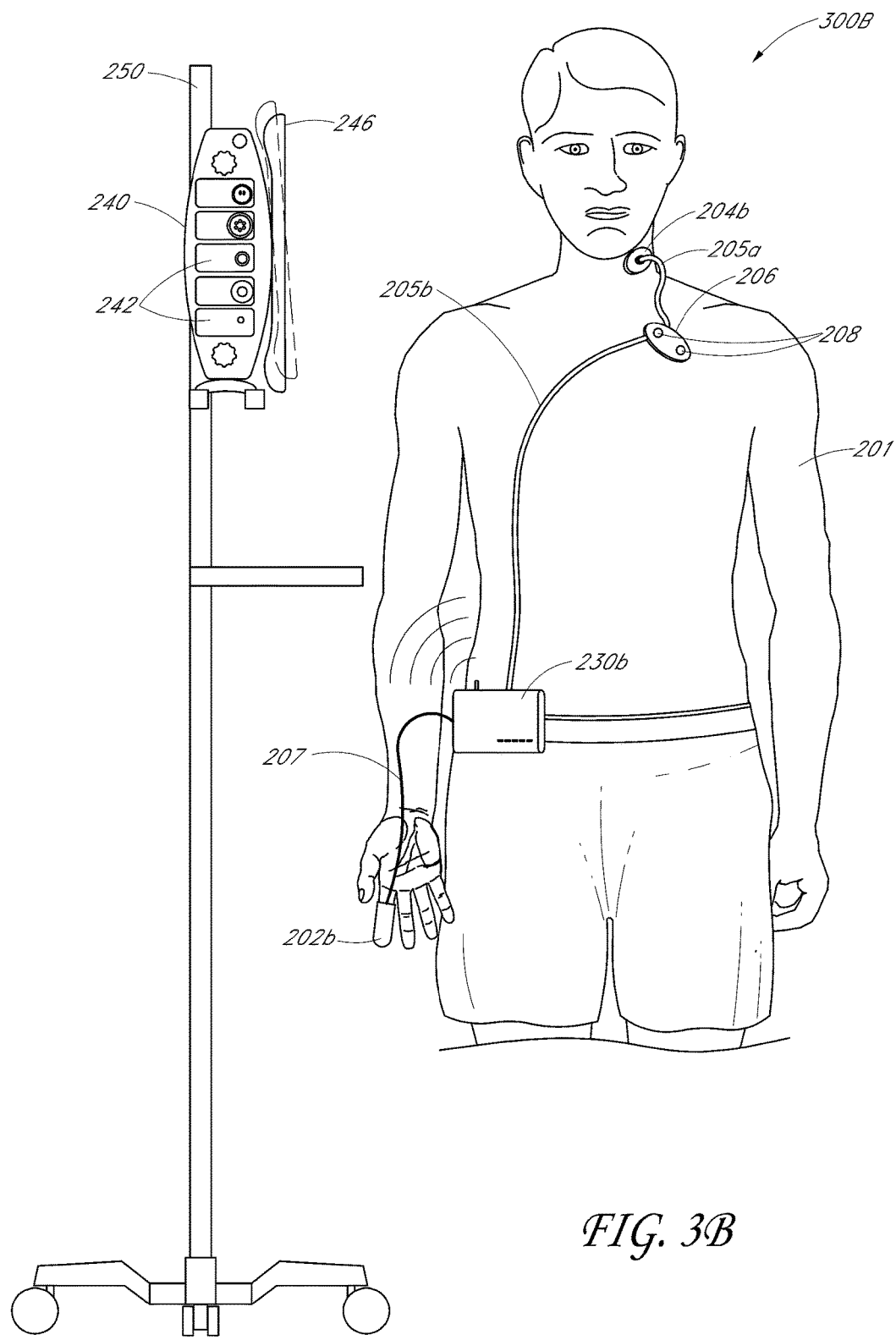

FIGS. 3A and 3B illustrate further embodiments of a patient monitoring system 300A, 300B having a single cable connecting multiple sensors. FIG. 3A depicts a tethered patient monitoring system 300A, while FIG. 3B depicts a wireless patient monitoring system 300B. The patient monitoring systems 300A, 300B illustrate example embodiments where a single cable 305 can be used to connect multiple sensors, without using a blood pressure cuff.

Referring to FIG. 3A, the acoustic and ECG sensors 204b, 206 of FIG. 2 are again shown coupled to the patient 201. As above, these sensors 204b, 206 are coupled together via a cable 205. However, the cable 250 is coupled to a junction device 230a instead of to a blood pressure cuff. In addition, the optical sensor 202b is coupled to the patient 201 and to the junction device 230a via a cable 207. The junction device 230a can anchor the cable 205b to the patient 201 (such as via the patient's belt) and pass through any signals received from the sensors 202b, 204b, 206 to a patient monitor 240 via a single cable 232.

In some embodiments, however, the junction device 230a can include at least some front-end signal processing circuitry. In some embodiments, the junction device 230a also includes a processor for processing physiological parameter measurements. Further, the junction device 230a can include all the features of the patient monitor 216b in some embodiments, such as providing a display that outputs parameters measured from data obtained by the sensors 202b, 204b, 206.

In the depicted embodiment, the patient monitor 240 is connected to a medical stand 250. The patient monitor 240 includes parameter measuring modules 242, one of which is connected to the junction device 230a via the cable 232. The patient monitor 240 further includes a display 246. The display 246 is a user-rotatable display in the depicted embodiment.

Referring to FIG. 3B, the patient monitoring system 300B includes nearly identical features to the patient monitoring system 300A. However, the junction device 230b includes wireless capability, enabling the junction device 230b to wirelessly communicate with the patient monitor 240 and/or other devices. The wireless patient monitoring system 300B can transmit data using any of a variety of wireless technologies, such as Wi-Fi (802.11x), Bluetooth (802.15.2), Zigbee (802.15.4), cellular telephony, infrared, RFID, satellite transmission, proprietary protocols, combinations of the same, and the like.

Figure 4A:
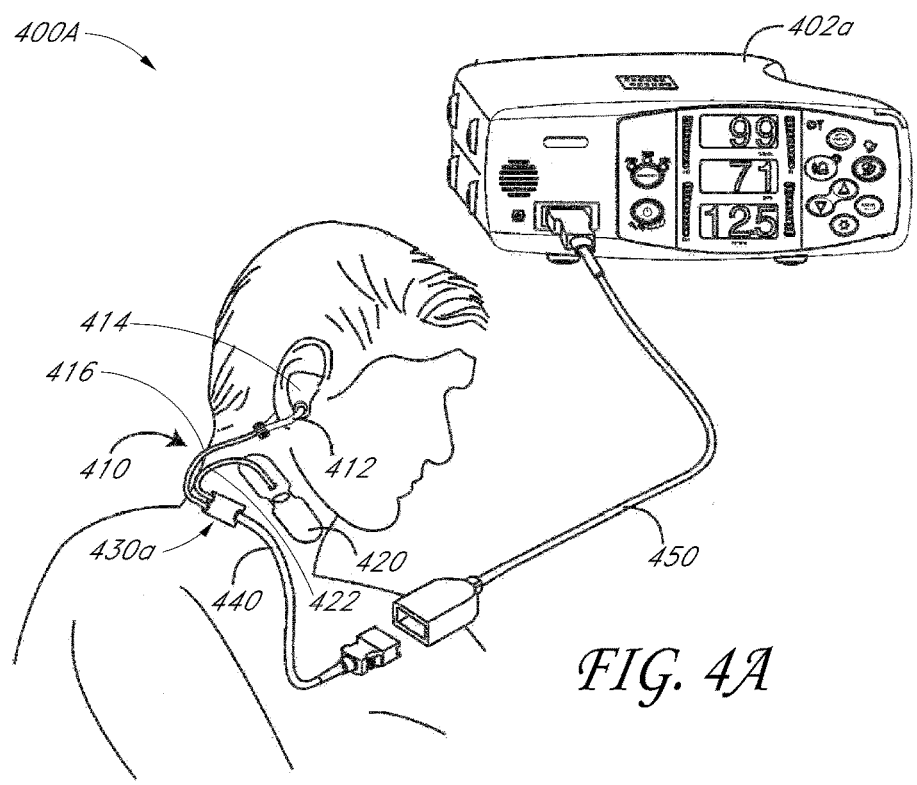
FIGS. 4A and 4B illustrate embodiments of an optical ear sensor and an acoustic sensor connected via a single cable connection system.
Figure 4B:
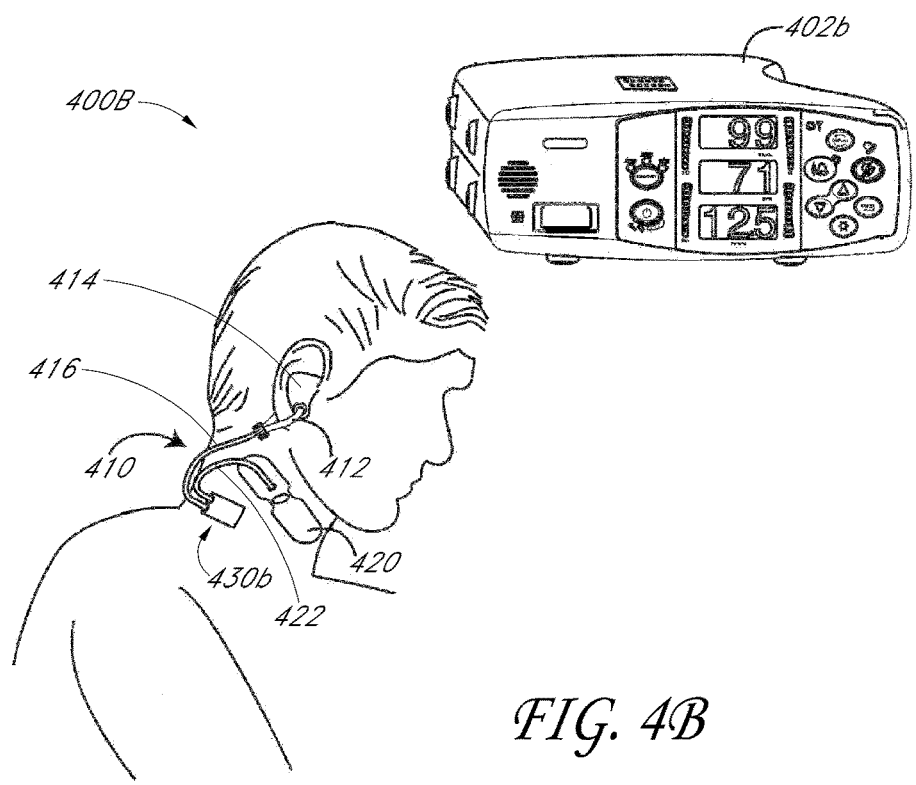

FIGS. 4A and 4B illustrate embodiments of patient monitoring systems 400A, 400B that depict alternative cable connection systems 410 for connecting sensors to a patient monitor 402. Like the cable 205 described above, these cable connection systems 410 can advantageously enhance patient mobility and comfort.

Referring to FIG. 4A, the patient monitoring system 400A includes a patient monitor 402a that measures physiological parameters based on signals obtained from sensors 412, 420 coupled to a patient. These sensors include an optical ear sensor 412 and an acoustic sensor 420 in the embodiment shown. The optical ear sensor 412 can include any of the features of the optical sensors described above. Likewise, the acoustic sensor 420 can include any of the features of the acoustic sensors described above.

The optical ear sensor 412 can be shaped to conform to the cartilaginous structures of the ear, such that the cartilaginous structures can provide additional support to the sensor 412, providing a more secure connection. This connection can be particularly beneficial for monitoring during pre-hospital and emergency use where the patient can move or be moved. In some embodiments, the optical ear sensor 412 can have any of the features described in U.S. application Ser. No. 12/658,872, filed Feb. 16, 2010, entitled "Ear Sensor," the disclosure of which is hereby incorporated by reference in its entirety.

An instrument cable 450 connects the patient monitor 402a to the cable connection system 410. The cable connection system 410 includes a sensor cable 440 connected to the instrument cable 250. The sensor cable 440 is bifurcated into two cable sections 416, 422, which connect to the individual sensors 412, 420 respectively. An anchor 430a connects the sensor cable 440 and cable sections 416, 422. The anchor 430a can include an adhesive for anchoring the cable connection system 410 to the patient, so as to reduce noise from cable movement or the like. Advantageously, the cable connection system 410 can reduce the number and size of cables connecting the patient to a patient monitor 402a. The cable connection system 410 can also be used to connect with any of the other sensors, patient-worn monitors, or wireless devices described above.

FIG. 4B illustrates the patient monitoring system 400B, which includes many of the features of the monitoring system 400A. For example, an optical ear sensor 412 and an acoustic sensor 420 are coupled to the patient. Likewise, the cable connection system 410 is shown, including the cable sections 416, 422 coupled to an anchor 430b. In the depicted embodiment, the cable connection system 410 communicates wirelessly with a patient monitor 402b. For example, the anchor 430b can include a wireless transceiver, or a separate wireless dongle or other device (not shown) can couple to the anchor 430b. The anchor 430b can be connected to a blood pressure cuff, wireless transceiver, junction device, or other device in some embodiments. The wireless transceiver, wireless dongle, or other device can transmit data using any of a variety of wireless technologies, such as Wi-Fi (802.11x), Bluetooth (802.15.2), Zigbee (802.15.4), cellular telephony, infrared, RFID, satellite transmission, proprietary protocols, combinations of the same, and the like.

Figure 5:
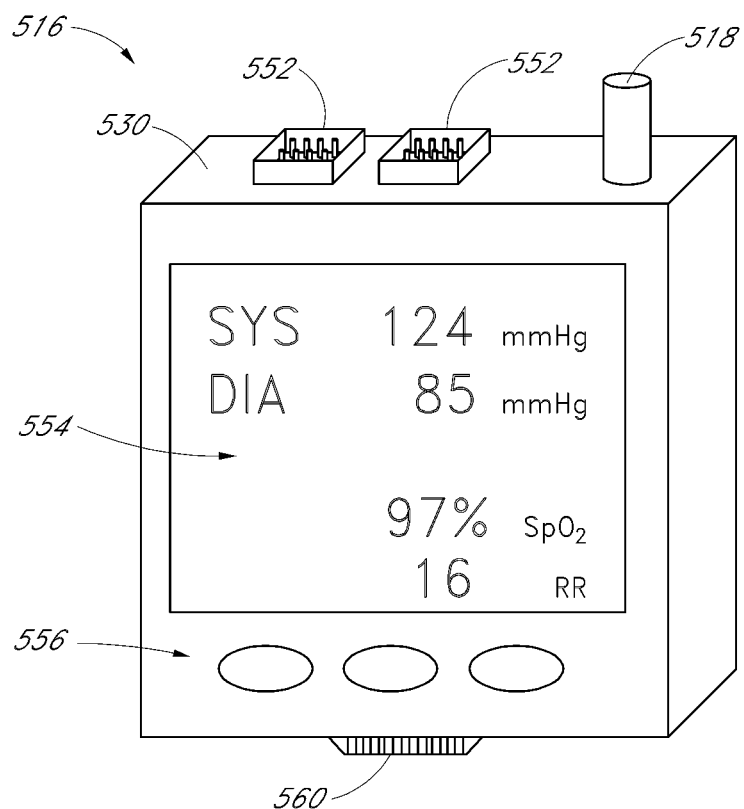
FIG. 5 illustrates an embodiment of a wireless transceiver that can be used with any of the patient monitoring systems described above.

FIG. 5 illustrates a more detailed embodiment of a wireless transceiver 516. The wireless transceiver 516 can have all of the features of the wireless transceiver 516 described above. For example, the wireless transceiver 516 can connect to a blood pressure cuff and to one or more physiological sensors, and the transceiver 516 can transmit sensor data to a wireless receiver. The wireless transceiver 516 can transmit data using any of a variety of wireless technologies, such as Wi-Fi (802.11x), Bluetooth (802.15.2), Zigbee (802.15.4), cellular telephony, infrared, RFID, satellite transmission, proprietary protocols, combinations of the same, and the like.

The depicted embodiment of the transceiver 516 includes a housing 530, which includes connectors 552 for sensor cables (e.g., for optical, acoustic, ECG, and/or other sensors) and a connector 560 for attachment to a blood pressure cuff or other patient-wearable device. The transceiver 516 further includes an antenna 518, which although shown as an external antenna, can be internal in some implementations.

The transceiver 516 can include one or more connectors on one or more sides of the housing 530. Providing connectors on different sides of the housing 530 allows for convenient sensor connection and prevents the sensor cables from tangling. For example, as shown in FIG. 5, the housing can include two connectors 552 on a first side of the housing 530 and an additional connector 560 on a second side of the housing 530.

In addition, the transceiver 516 includes a display 554 that depicts values of various parameters, such as systolic and diastolic blood pressure, SpO2, and respiratory rate (RR).

The display 554 can also display trends, alarms, and the like. The transceiver 516 can be implemented with the display 554 in embodiments where the transceiver 516 also acts as a patient monitor. The transceiver 516 further includes controls 556, which can be used to manipulate settings and functions of the transceiver 516.

FIGS. 6A through 6C illustrate embodiments of wireless patient monitoring systems 600. These wireless patient monitoring systems can transmit data using any of a variety of wireless technologies, such as Wi-Fi (802.11x), Bluetooth (802.15.2), Zigbee (802.15.4), cellular telephony, infrared, RFID, satellite transmission, proprietary protocols, combinations of the same, and the like.

FIG. 6A illustrates a patient monitoring system 600A that includes a wireless transceiver 616, which can include the features of any of the transceivers 216, 216 described above. The transceiver 616 provides a wireless signal over a wireless link 612 to a patient monitor 620. The wireless signal can include physiological information obtained from one or more sensors, physiological information that has been front-end processed by the transceiver 616, or the like.

The patient monitor 620 can act as the wireless receiver 220 of FIG. 2. The patient monitor 620 can process the wireless signal received from the transceiver 616 to obtain values, waveforms, and the like for one or more physiological parameters. The patient monitor 620 can perform any of the patient monitoring functions described above with respect to FIGS. 2 through 5.

In addition, the patient monitor 620 can provide at least some of the physiological information received from the transceiver 616 to a multi-patient monitoring system (MMS) 640 over a network 630. The MMS 640 can include one or more physical computing devices, such as servers, having hardware and/or software for providing the physiological information to other devices in the network 630. For example, the MMS 640 can use standardized protocols (such as TCP/IP) or proprietary protocols to communicate the physiological information to one or more nurses' station computers (not shown) and/or clinician devices (not shown) via the network 630. In one embodiment, the MMS 640 can include some or all of the features of the MMS described in U.S. Publication No. 2008/0188760, referred to above.

The network 630 can be a LAN or WAN, wireless LAN ("WLAN"), or other type of network used in any hospital, nursing home, patient care center, or other clinical location. In some implementations, the network 210 can interconnect devices from multiple hospitals or clinical locations, which can be remote from one another, through the Internet, one or more Intranets, a leased line, or the like. Thus, the MMS 640 can advantageously distribute the physiological information to a variety of devices that are geographically co-located or geographically separated.

FIG. 6B illustrates another embodiment of a patient monitoring system 600B, where the transceiver 616 transmits physiological information to a base station 624 via the wireless link 612. In this embodiment, the transceiver 616 can perform the functions of a patient monitor, such as any of the patient monitor functions described above. The transceiver 616 can provide processed sensor signals to the base station 624, which forwards the information on to the MMS 640 over the network 630.

FIG. 6C illustrates yet another embodiment of a patient monitoring system 600B, where the transceiver 616 transmits physiological information directly to the MMS 640. The MMS 640 can include wireless receiver functionality, for example. Thus, the embodiments shown in FIGS. 6A through 6C illustrate that the transceiver 616 can communicate with a variety of different types of devices.

Figure 7:
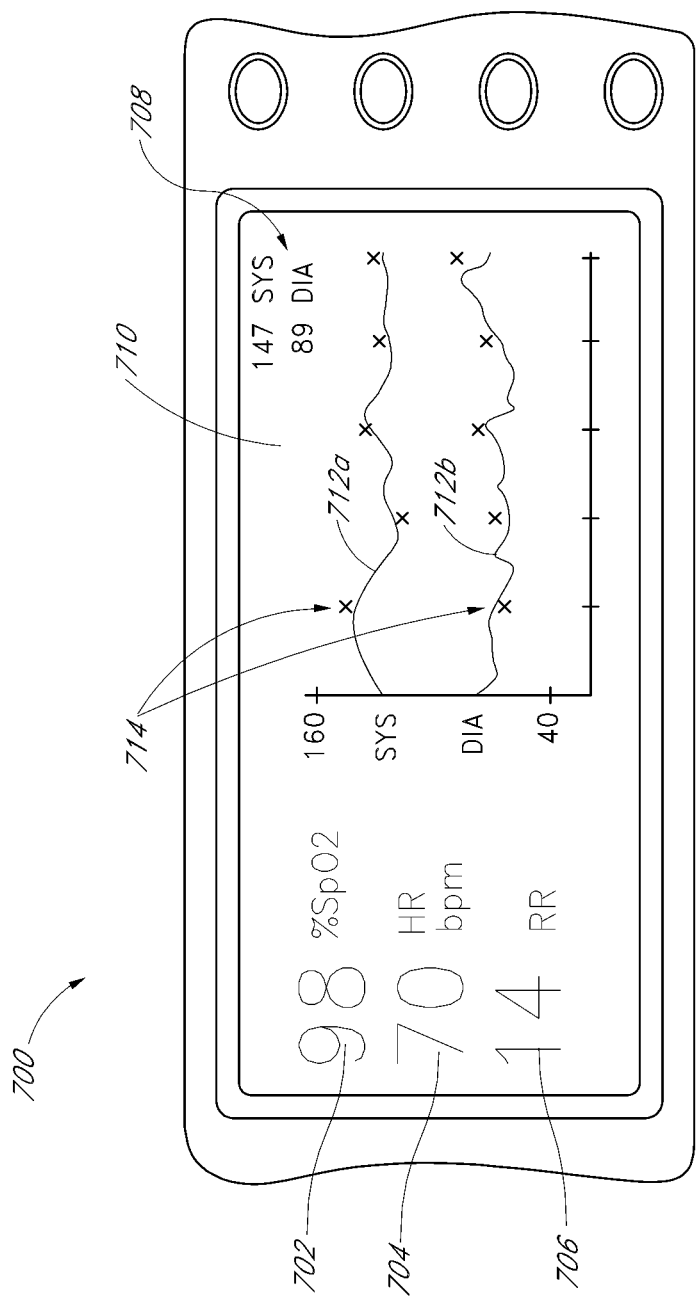
FIG. 7 illustrates an embodiment of a physiological parameter display that can be used with any of the patient monitoring systems described above.

FIG. 7 illustrates an embodiment of a physiological parameter display 700. The physiological parameter display 700 can be output by any of the systems described above. For instance, the physiological parameter display 700 can be output by any of the wireless receivers, transceivers, or patient monitors described above. The parameter display 700 can be output over a variety of wireless technologies, such as Wi-Fi (802.11x), Bluetooth (802.15.2), Zigbee (802.15.4), cellular telephony, infrared, RFID, satellite transmission, proprietary protocols, combinations of the same, and the like. Advantageously, in certain embodiments, the physiological parameter display 700 can display multiple parameters, including noninvasive blood pressure (NIBP) obtained using both oscillometric and non-oscillometric techniques.

The physiological parameter display 700 can display any of the physiological parameters described above, to name a few. In the depicted embodiment, the physiological parameter display 700 is shown displaying oxygen saturation 702, heart rate 704, and respiratory rate 706. In addition, the physiological parameter display 700 displays blood pressure 708, including systolic and diastolic blood pressure.

The display 700 further shows a plot 710 of continuous or substantially continuous blood pressure values measured over time. The plot 710 includes a trace 712a for systolic pressure and a trace 712b for diastolic pressure. The traces 712a, 712b can be generated using a variety of devices and techniques. For instance, the traces 712a, 712b can be generated using any of the velocity-based continuous blood pressure measurement techniques described above and described in further detail in U.S. Pat. Nos. 5,590,649 and 5,785,659, referred to above.

Periodically, oscillometric blood pressure measurements (sometimes referred to as Gold Standard NIBP) can be taken, using any of the cuffs described above. These measurements are shown by markers 714 on the plot 710. By way of illustration, the markers 714 are "X's" in the depicted embodiment, but the type of marker 714 used can be different in other implementations. In certain embodiments, oscillometric blood pressure measurements are taken at predefined intervals, resulting in the measurements shown by the markers 714.

In addition to or instead of taking these measurements at intervals, oscillometric blood pressure measurements can be triggered using ICI techniques, e.g., based at least partly on an analysis of the noninvasive blood pressure measurements indicated by the traces 712a, 712b. Advantageously, by showing both types of noninvasive blood pressure measurements in the plot 710, the display 700 can provide a clinician with continuous and oscillometric blood pressure information.

FIG. 8 illustrates another embodiment of a patient monitoring system 800. The features of the patient monitoring system 800 can be combined with any of the features of the systems described above. Likewise, any of the features described above can be incorporated into the patient monitoring system 800. Advantageously, in the depicted embodiment, the patient monitoring system 800 includes a cable hub 806 that enables one or many sensors to be selectively connected and disconnected to the cable hub 806.

Like the patient monitoring systems described above, the monitoring system 800 includes a cuff 810 with a patient device 816 for providing physiological information to a monitor 820 or which can receive power from a power supply (820). The cuff 810 can be a blood pressure cuff or merely a holder for the patient device 816. The patient device 816 can instead be a wireless transceiver having all the features of the wireless devices described above. The wireless transceiver can transmit data using any of a variety of wireless technologies, such as Wi-Fi (802.11x), Bluetooth (802.15.2), Zigbee (802.15.4), cellular telephony, infrared, RFID, satellite transmission, proprietary protocols, combinations of the same, and the like.

The patient device 816 is in coupled with an optical finger sensor 802 via cable 807. Further, the patient device 816 is coupled with the cable hub 806 via a cable 805a. The cable hub 806 can be selectively connected to one or more sensors. In the depicted embodiment, example sensors shown coupled to the cable hub 806 include an ECG sensor 808a and a brain sensor 840. The ECG sensor 808a can be single-lead or multi-lead sensor. The brain sensor 840 can be an electroencephalography (EEG) sensor and/or an optical sensor. An example of EEG sensor that can be used as the brain sensor 840 is the SEDLine™ sensor available from Masimo® Corporation of Irvine, Calif., which can be used for depth-of-anesthesia monitoring among other uses. Optical brain sensors can perform spectrophotometric measurements using, for example, reflectance pulse oximetry. The brain sensor 840 can incorporate both an EEG/depth-of-anesthesia sensor and an optical sensor for cerebral oximetry.

The ECG sensor 808a is coupled to an acoustic sensor 804 and one or more additional ECG leads 808b. For illustrative purposes, four additional leads 808b are shown, for a 5-lead ECG configuration. In some embodiments, one or two additional leads 808b are used instead of four additional leads. In some embodiments, up to at least 12 leads 808b can be included. Acoustic sensors can also be disposed in the ECG sensor 808a and/or lead(s) 808b or on other locations of the body, such as over a patient's stomach (e.g., to detect bowel sounds, thereby verifying patient's digestive health, for example, in preparation for discharge from a hospital). Further, in some embodiments, the acoustic sensor 804 can connect directly to the cable hub 806 instead of to the ECG sensor 808a.

As mentioned above, the cable hub 806 can enable one or many sensors to be selectively connected and disconnected to the cable hub 806. This configurability aspect of the cable hub 806 can allow different sensors to be attached or removed from a patient based on the patient's monitoring needs, without coupling new cables to the monitor 820. Instead, a single, light-weight cable 832 couples to the monitor 820 in certain embodiments, or wireless technology can be used to communicate with the monitor 820 (see, e.g., FIG. 1). A patient's monitoring needs can change as the patient is moved from one area of a care facility to another, such as from an operating room or intensive care unit to a general floor. The cable configuration shown, including the cable hub 806, can allow the patient to be disconnected from a single cable to the monitor 820 and easily moved to another room, where a new monitor can be coupled to the patient. Of course, the monitor 820 may move with the patient from room to room, but the single cable connection 832 rather than several can facilitate easier patient transport.

Further, in some embodiments, the cuff 810 and/or patient device 816 need not be included, but the cable hub 806 can instead connect directly to the monitor wirelessly or via a cable. Additionally, the cable hub 806 or the patient device 816 may include electronics for front-end processing, digitizing, or signal processing for one or more sensors. Placing front-end signal conditioning and/or analog-to-digital conversion circuitry in one or more of these devices can make it possible to send continuous waveforms wirelessly and/or allow for a small, more user-friendly wire (and hence cable 832) routing to the monitor 820.

The cable hub 806 can also be attached to the patient via an adhesive, allowing the cable hub 806 to become a wearable component. Together, the various sensors, cables, and cable hub 806 shown can be a complete body-worn patient monitoring system. The body-worn patient monitoring system can communicate with a patient monitor 820 as shown, which can be a tablet, handheld device, a hardware module, or a traditional monitor with a large display, to name a few possible devices.

FIGS. 9A-9D illustrate another embodiment of a wireless monitoring system 900 including a wireless monitor 902 coupled to a sensor 930. The wireless monitoring system 900 is configured to connect to one or more sensors and/or a bedside monitor. The features of the wireless monitoring system 900 can be combined with any of the features of the systems described above. Likewise, any of the features described above can be incorporated into the patient monitoring system 900. The wireless monitor 902 includes a removable battery 904 having a data storage component. The removable battery 904 can be used to pair the wireless monitor 902 with the correct bedside monitor as described below. The battery 904 is positioned on the front side of the wireless monitor 902, so the battery 904 can be replaced without disconnecting a wireless monitor housing from the patient. Further details of these drawings are described below.

Figure 10:
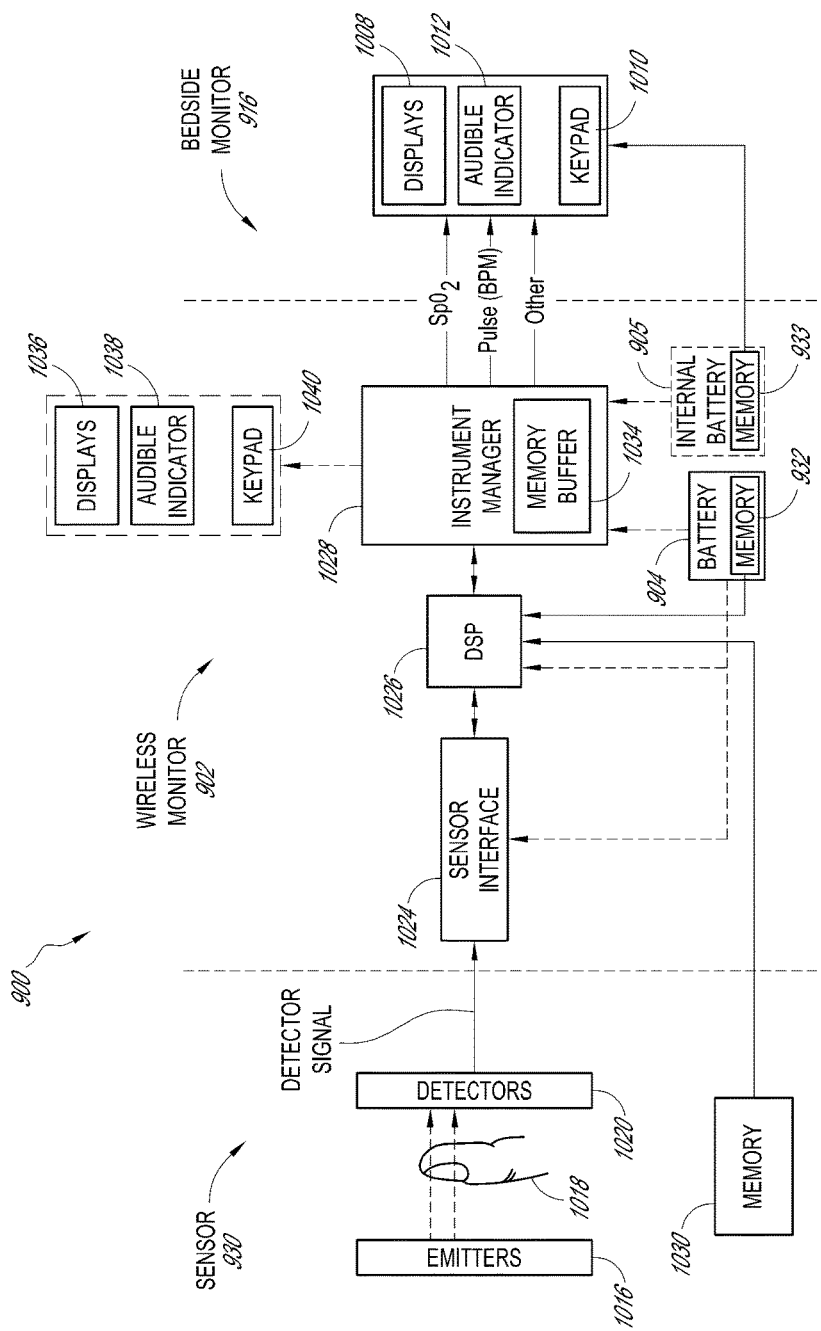
FIG. 10 illustrates the embodiment of the wireless patient monitoring system illustrated in FIGS. 9A-9D in schematic form.

FIG. 10 illustrates details of an embodiment of the wireless monitoring system 900 in a schematic form. Typically, the sensor 930 includes energy emitters 1016 located on one side of a patient monitoring site 1018 and one or more detectors 1020 located generally opposite. The patient monitoring site 1018 is usually a patient's finger (as pictured), toe, ear lobe, or the like. Energy emitters 1016, such as LEDs, emit particular wavelengths of energy through the flesh of a patient at the monitoring site 1018, which attenuates the energy. The detector(s) 1020 then detect the attenuated energy and send representative signals to the wireless monitor 902.

The wireless monitor 902 can include a sensor interface 1024 and a digital signal processor (DSP) 1026. The sensor interface 1024 receives the signals from the sensor 930 detector(s) 1020 and passes the signals to the DSP 1026 for processing into representations of physiological parameters. In some embodiments, the DSP 1026 also communicates with a memory or information element, such as a resistor or capacitor, 1030 located on the sensor 930, such memory typically contains information related to the properties of the sensor that may be useful in processing the signals, such as, for example, emitter 1016 energy wavelengths.

In some embodiments, the physiological parameters are passed to an instrument manager 1028, which may further process the parameters for display by a bedside monitor 916. The instrument manager 1028 may include a memory buffer 1034 to maintain this data for processing throughout a period of time. Memory buffer 1034 may include RAM, Flash or other solid state memory, magnetic or optical disk-based memories, combinations of the same or the like.

In some embodiments, the wireless monitor is able to display one or more physiological parameters. The wireless monitor 902 can include one or more displays 1036, control buttons 1040, one or more speakers 1038 for audio messages. Control buttons 1040 may comprise a keypad, a full keyboard, a touch screen, a track wheel, and the like.

The wireless monitor 902 is powered by a battery 904. In some embodiments, the battery 904 directly or indirectly powers the sensor interface 1024, DSP 1026, and the instrument manager 1028.

The battery 904 includes memory 932, such memory stores wireless communication information needed for the wireless monitor 902 to wirelessly communicate with bedside monitor 916. The battery 904 can communicate the information stored on the memory 932 to the wireless monitor 902 or bedside monitor 916, and the memory 932 can store information received from the wireless monitor 902 or bedside monitor 916.

The bedside monitor 916 wirelessly receives the physiological data and/or parameters from the wireless monitor 902 and is able to display one or more physiological parameters. The bedside monitor 916 can include one or more displays 1008, control buttons 1010, a speaker 1012 for audio messages, and/or a wireless signal broadcaster. Control buttons 1010 may comprise a keypad, a full keyboard, a track wheel, and the like.

As shown in FIG. 10, the wireless monitor 902 can include an optional internal battery 905 capable of powering the wireless monitor 902 when the battery 904 is disconnected from the wireless monitor 902. The internal battery 905 can include additional backup memory 933 to store information when the battery 904 is disconnected from the wireless monitor 902. The internal battery 905 can be useful when a caregiver replaces the battery 904 with a different, fully-charged battery. While the battery 904 is disconnected from the wireless monitor 902, the wireless monitor 902 can continue to display and communicate information.

In several embodiments, the wireless patient monitoring system includes one or more sensors, including, but not limited to, a sensor 930 to monitor oxygen saturation and pulse rate. These physiological parameters can be measured using a pulse oximeter. In general, the sensor 930 has light emitting diodes that transmit optical radiation of red and infrared wavelengths into a tissue site and a detector that responds to the intensity of the optical radiation after absorption (e.g. by transmission or transreflectance) by pulsatile arterial blood flowing within the tissue site. Based on this response, a processor determines measurements for $SpO_2$, pulse rate, and can output representative plethsmorgraphic waveforms. Thus, "pulse oximetry" as used herein encompasses its broad ordinary meaning known to one of skill in the art, which includes at least those noninvasive procedures for measuring parameters of circulating blood through spectroscopy.

The wireless monitoring system 900 can include any of the sensors described herein in addition to or in alternative to the pulse oximeter. For example, the wireless monitoring system 900 can also include sensors for monitoring acoustics, sedation state, blood pressure, ECG, body temperature, and/or cardiac output. The wireless monitor may also include an accelerometer or gyroscope. The wireless patient monitoring system may include any of the above-mentioned sensors alone or in combination with each other.

In several embodiments, the wireless monitor 902 includes a wireless transmitter to transmit sensor data and/or a wireless receiver to receive data from another wireless transmitter or transceiver. By transmitting the sensor data wirelessly, the wireless monitor 902 can advantageously replace some or all cables that connect patients to bedside monitoring devices. Alternatively, the wireless monitor 902 calculates physiological parameters based on the sensor data and wirelessly transmits the physiological parameters and/or the sensor data itself to the bedside monitor. The physiological parameter can be numerical information, such as oxygen saturation ($SpO_2$) or pulse rate, or a graphical depiction of the sensor data. The data processors can be positioned in the wireless monitor housing or the battery. By configuring the wireless monitor 902 to calculate the physiological parameter, less data transfer is required to transmit information from the wireless monitor to the bedside monitor. Processing the sensor data in the wireless monitor 902 also improves the quality of the signal transferred to the bedside monitor.

Figure 9A:
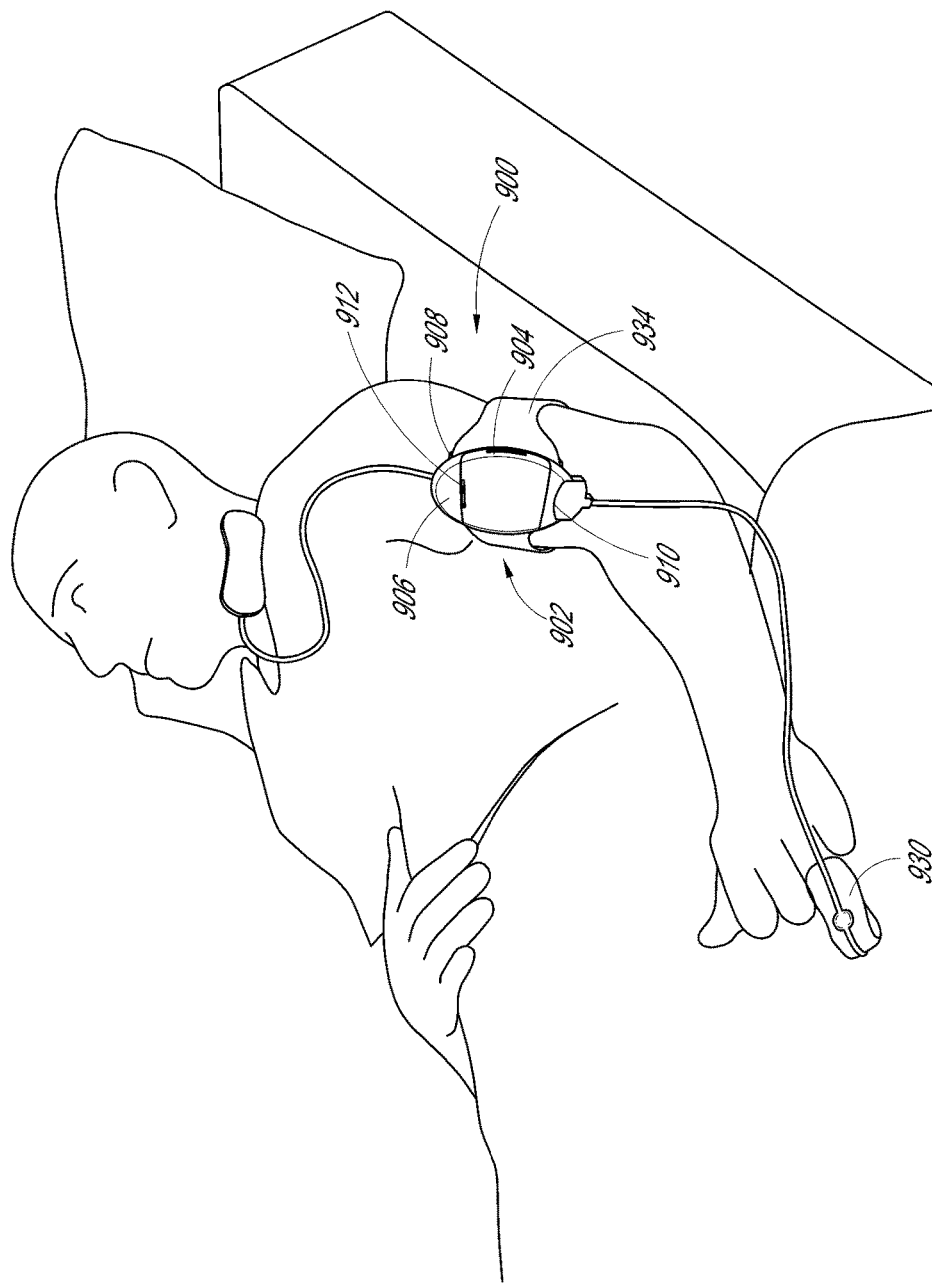
FIGS. 9A-9D illustrate an embodiment of a wireless patient monitoring system.
Figure 9B:
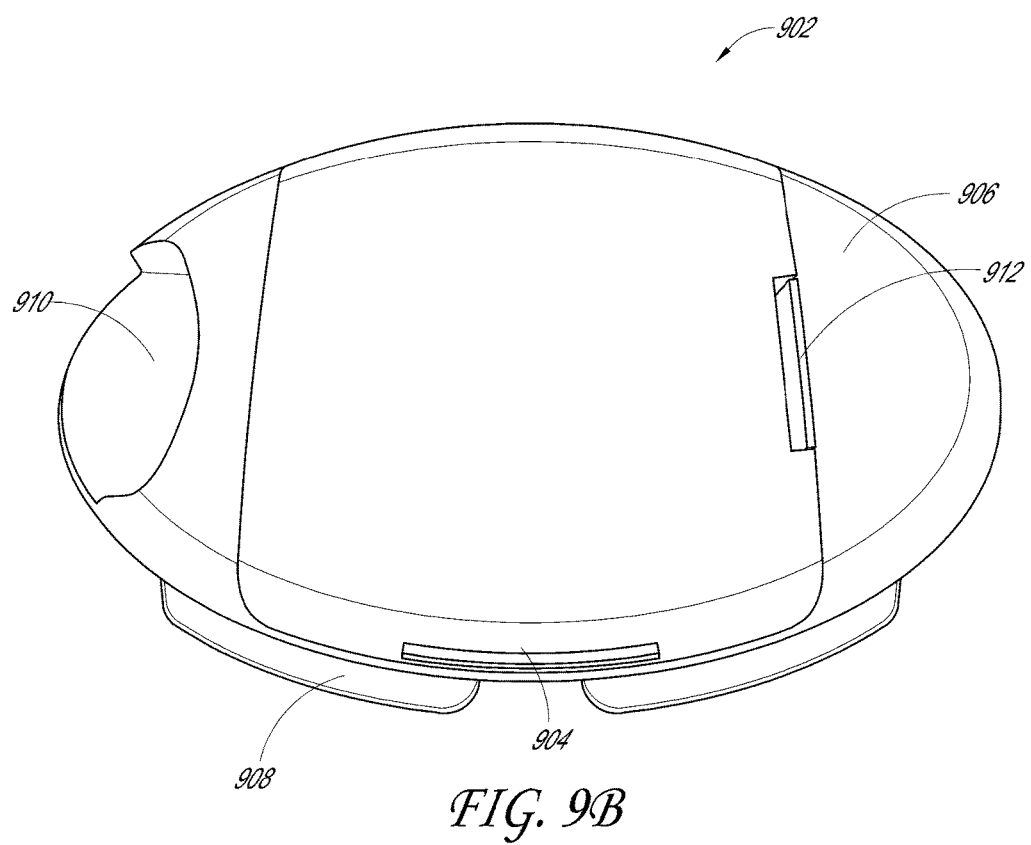
Figure 9C:
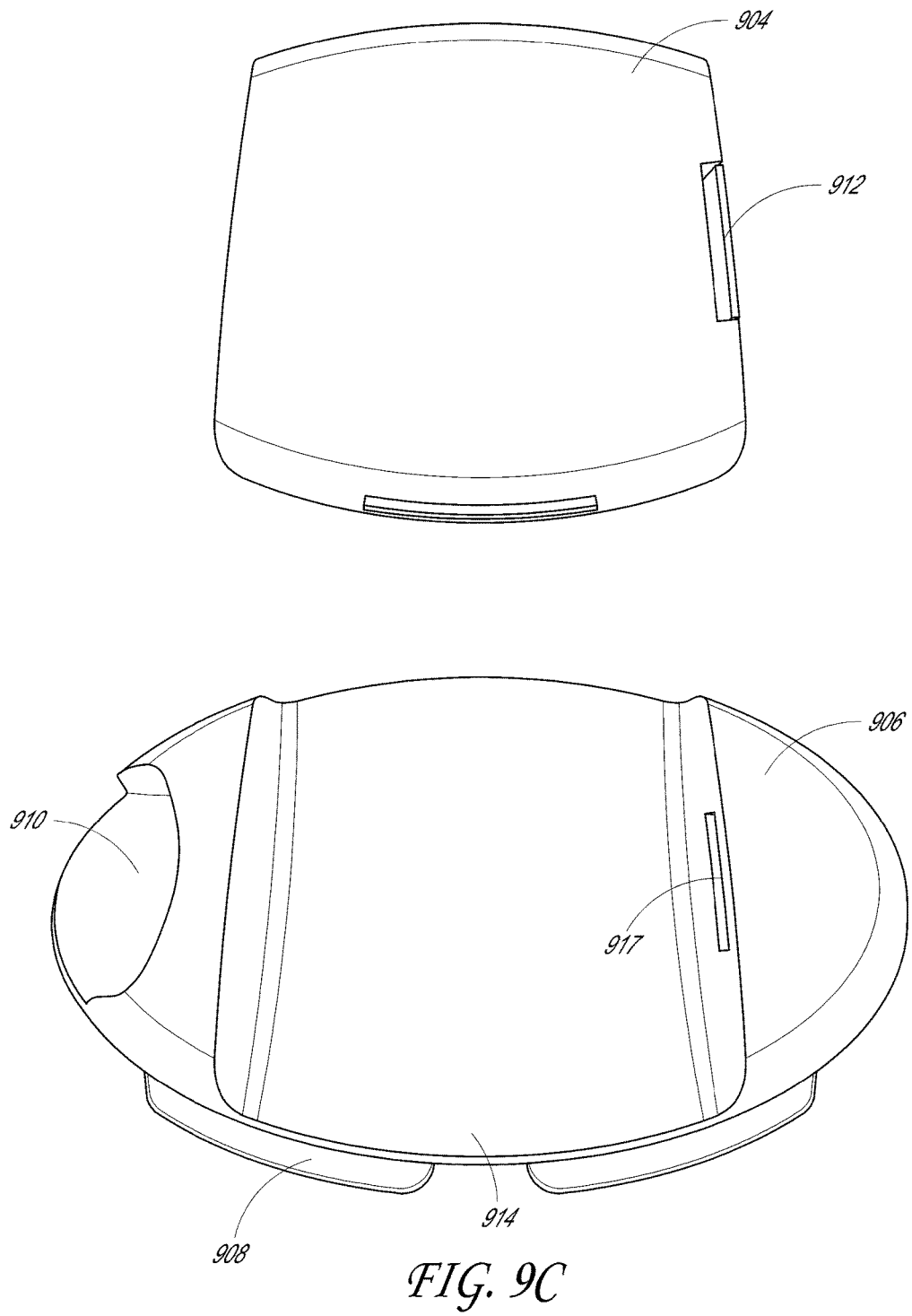

As shown in FIGS. 9B-9C, the wireless monitor 902 includes a removable battery 904 and a base 906. The base 906 can include processing and wireless transmission capabilities and/or share processing function with the battery 904. Removable battery 904 includes a release mechanism 912 to release the battery 904 from the base 906. As depicted in FIG. 9B, the base 906 can include a battery receiving portion 914 and a notch 917 to lock the removable battery 904 in place. Wireless monitor 902 can have one or more outlets 910 to plug in the sensor 930, such as the pulse oximeter, acoustic respiratory sensor, ECG, sedation sensor, blood pressure cuff, or any other sensor. In some embodiments, one or more outlets 910 can be positioned on one or more sides of the wireless monitor 902. For example, the wireless monitor can include an outlet on one side for an acoustic respiratory sensor and an outlet on an opposite side for a pulse oximeter.

Wireless monitor 902 can include an opening 908 through which an arm band 934 can be passed to secure the wireless monitor 902 to the arm of the patient, as shown in FIG. 9A. The arm band 934 can be reusable, disposable or resposable. Similarly, any of the sensors 930 can be disposable or resposable. Resposable devices can include devices that are partially disposable and partially reusable. Thus, for example, the acoustic sensor can include reusable electronics, but a disposable contact surface (such as an adhesive) where the sensor comes into contact with the patient's skin.

The sensors 930 and/or wireless monitor 902 need not be worn around the patient's arm, but can be worn at any other location, including not at all. The sensors 930 and/or wireless monitor 902 need not be coupled to an arm band, but can be coupled to a patient's belt or a chest strap, can be carried by the patient (e.g., via a shoulder strap or handle), or can be placed on the patient's bed next to the patient, among other locations.

Figure 9D:
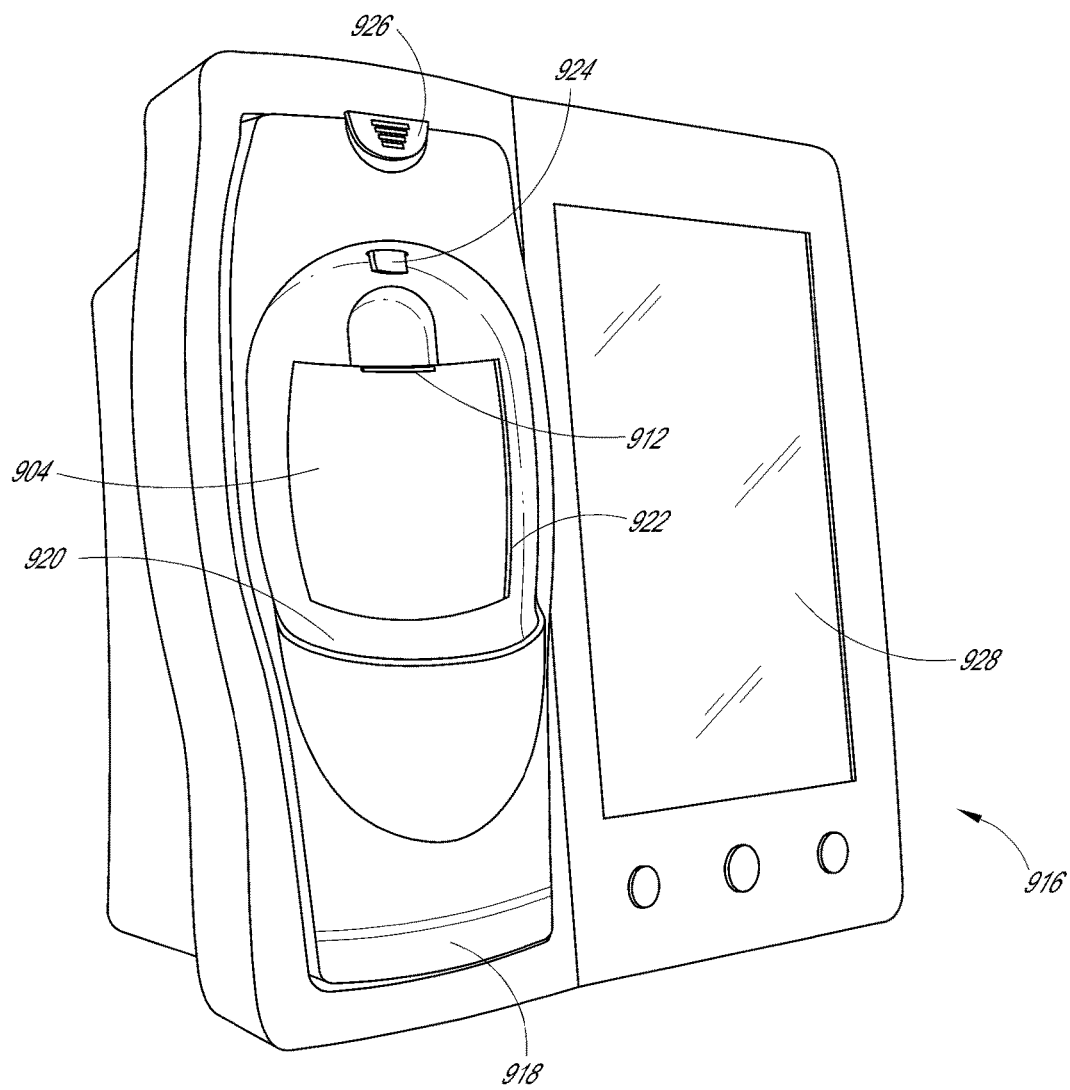

FIG. 9D illustrates the battery 904 docked with a bedside monitor 916. Bedside monitor 916 has a battery charging station 922 for receiving and charging removable battery 904. When the wireless monitor 902 is using a first battery, the battery charging station 922 can charge a second battery, so when the battery levels of the first battery are low, a second battery is readily available. Each battery is capable of powering the wireless monitor 902 for at least one nursing shift, so each nurse only has to replace the battery once either at the beginning or end of each shift.

An adapter 918 can be integrated with the bedside monitor or separately connected to bedside monitor 916. The bedside monitor 916 includes a release mechanism 926 to release the adaptor 918 from the bedside monitor 916. Adaptor 918 includes docking station 920 to receive the entire wireless monitor (not shown). Locking mechanism 924 holds the wireless monitor 902 in place. Other components may be connected to the bedside monitor 916 instead of the adaptor 918, such as a handheld patient monitor device.

In some embodiments, the adaptor 918 includes a docking station 920 to receive the entire wireless monitor 902. The wireless monitor 902 can be placed in the docking station 920 when it is not in use to prevent the wireless monitor 902 from being lost. The bedside monitor 916 can charge the battery 904 when the wireless monitor 902 is connected to the bedside monitor 916. In certain aspects, the bedside monitor 916 can communicate a password, unique identifier, appropriate channel information, or other wireless communication information to the wireless monitor 902, and vice versa, when the wireless monitor 902 is connected to the bedside monitor 916.

As shown in FIG. 9D, the bedside monitor 916 is capable of simultaneously receiving a first battery and a wireless monitor 902 having a second battery. The bedside monitor 916 is configured to charge and sync both the first and second batteries. When the first battery and/or the wireless monitor 902 and second battery are physically docked in the bedside monitor 916, the first and/or second battery can communication with the bedside monitor 916 over a wired connection.

The bedside monitor 916 can include a display screen 928 for displaying the physiological parameters, including trends, waveforms, related alarms, and the like. In certain aspects, the bedside monitor 916 can display the appropriate channel for communication and/or whether the wireless monitor 902 is properly communicating with the bedside monitor 916.

The bedside monitor 916 can include a computer-readable storage medium, such as a physical storage device, for storing the physiological data. In certain aspects, the bedside monitor can include a network interface for communicating the physiological data to one or more hosts over a network, such as to a nurse's station computer in a hospital network.

The wireless monitor 902 can transmit data to the bedside monitor 916 using any of a variety of wireless technologies, such as Wi-Fi (802.11x), Bluetooth, ZigBee, cellular telephony, infrared, RFID, satellite transmission, proprietary protocols, combinations of the same, and the like. The wireless monitor 902 can perform solely telemetry functions, such as measuring and reporting information about the patient.

The wireless monitor 902, or any of the wireless monitor embodiments discussed herein, can be configured to utilize different wireless technologies. In certain scenarios, it may be desirable to transmit data over Bluetooth or ZigBee, for example, when the distance between the wireless monitor 902 and the bedside monitor 916 is within range of Bluetooth or ZigBee communication. Transmitting data using Bluetooth or ZigBee is advantageous because these technologies require less power than other wireless technologies. In other scenarios, it may be desirable to transmit data using Wi-Fi or cellular telephony, for example, when the wireless monitor is out of range of communication for Bluetooth or ZigBee. A wireless monitor 902 may be able to transmit data over a greater distance using Wi-Fi or cellular telephony than other wireless technologies. In still other scenarios, it may be desirable to transmit data using a first wireless technology and automatically switch to a second wireless technology in order to maximize data transfer and energy efficiency.

In some embodiments, the wireless monitor 902 automatically transmits data over Bluetooth or ZigBee when the wireless monitor 902 is within a pre-determined distance from bedside monitor 916. The wireless transmitter 902 automatically transmits data over Wi-Fi or cellular telephony when the wireless monitor 902 is beyond a pre-determined distance away from the bedside monitor 916. In certain embodiments, the wireless monitor 902 can automatically convert from Bluetooth or ZigBee to Wi-Fi or cellular telephony, and vice versa, depending on the distance between the wireless monitor 902 and bedside monitor 916.

In some embodiments, the wireless monitor 902 automatically transmits data over Bluetooth or ZigBee when the Bluetooth or ZigBee signal strength is sufficiently strong or when there is interference with Wi-Fi or cellular telephony. The wireless monitor 902 automatically transmits data over Wi-Fi or cellular telephony when the Bluetooth or ZigBee signal strength is not sufficiently strong. In certain embodiments, the wireless monitor 902 can automatically convert from Bluetooth or ZigBee to Wi-Fi or cellular telephony, and vice versa, depending on signal strength.

Existing wireless bedside monitoring devices can be difficult to use because it can be difficult to pair the wireless device with the correct bedside monitor, making it difficult to switch wireless devices or switch bedside monitors. Some wireless systems require the care provider to program the wireless device to communicate with the correct patient monitor. Other wireless systems require a separate token or encryption key and several steps to pair the wireless device with the correct bedside monitors. Some systems require the token to be connected to the bedside monitor, then connected to the wireless device, and then reconnected to the bedside monitor.

In certain scenarios, it may be desirable to share wireless communication information between a wireless monitor 902 and a bedside monitor 916 without a separate token or encryption key. In some embodiments, the removable battery 904 includes a data storage component, such as memory 932, capable of storing wireless communication information. The battery 904 is configured to connect to both the wireless monitor 902 and the bedside monitor 916. Combining the battery 904 with a data storage component can decrease the total number of components and decrease the number of steps it takes to transfer wireless communication information between the wireless monitor 902 and bedside monitor 916 because a separate token or encryption key is not needed. This method of data transfer also eliminates user input errors arising from users having to program the wireless monitor 902 and/or bedside monitor 916 and allows for easy transfer of wireless communication information between the wireless monitor 902 and bedside monitor 916.

For security purposes, it may be desirable to use security tokens to ensure that the correct bedside monitor 916 receives the correct wirelessly transmitted data. Security tokens prevent the bedside monitor 916 from accessing the transmitted data unless wireless monitor 902 and bedside monitor 916 share the same password. The password may be a word, passphrase, or an array of randomly chosen bytes.

When the battery 904 is connected to the bedside monitor 916, the bedside monitor 916 can communicate a password to the battery 904, and the battery 904 stores the password on its data storage component. The battery 904 can communicate a password for the wireless monitor 902 to the bedside monitor 916. The battery 904 can then be disconnected from the bedside monitor 916 and connected to the wireless monitor 902. When the battery 904 is connected to the wireless monitor 902, the battery 904 can communicate the password to the wireless monitor 902. The wireless monitor 902 can then communicate wirelessly with the correct bedside monitor 916.

In some scenarios, it may be desirable to pair the wireless monitor 902 with the bedside monitor 916 to avoid interference from other wireless devices. When the removable battery 904 is connected to the bedside monitor 916, the bedside monitor 916 communicates a unique identifier to the battery 904, and the battery 904 stores the unique identifier on its data storage component. The battery 904 can communicate a unique identifier for the wireless monitor 902 to the bedside monitor 916. The battery 904 can then be disconnected from the bedside monitor 916 and connected to the wireless monitor 902. When the battery 904 is connected to the wireless monitor 902, the battery 904 can communicate the unique identifier to the wireless monitor 902, so that the wireless monitor 902 can transmit data to the correct bedside monitor 916.

In some scenarios, it is desirable for the wireless monitor 902 to be configured to transmit data over the correct channel. Channels provide a mechanism to avoid sources of wireless interference. When the removable battery 904 is connected to the bedside monitor 916, the bedside monitor 916 communicates the appropriate channel to the battery 904, and the battery 904 stores the channel information on its data storage component. If necessary, the battery 904 can communicate a wireless monitor channel the bedside monitor 916. The battery 904 is then disconnected from the bedside monitor 916 and connected to the wireless monitor 902. When the battery 904 is connected to the wireless monitor 902, the battery 904 can communicate the appropriate channel information to the wireless monitor 902, thereby ensuring the wireless monitor 902 transmits data over the correct channel.

The battery 904, or any battery embodiment described herein, can receive or communicate any one or combination of passwords, tokens, or channels as described above. The wireless communication information can include information to communicate over each protocol the wireless monitor 902 is configured to communicate over. For example, if the wireless monitor 902 is capable of communicating over Wi-Fi and Bluetooth, then the battery 904 is capable of receiving wireless communication information to communicate over both Wi-Fi and Bluetooth.

In some scenarios, the method in any of the above mentioned methodologies may be reversed. For example, in some embodiments, the battery 904 is initially connected to the wireless monitor 902. When the battery 904 is connected to the wireless monitor 902, the wireless monitor 902 can communicate wireless communication information identifying the wireless monitor 902 to the battery 904, and the battery 904 can store the information on its data storage component. The battery can communicate wireless communication information identifying the bedside monitor 916 to the wireless monitor 902. After the battery 904 is disconnected from the wireless monitor 902, the battery 904 is connected to the bedside monitor 916. The battery 904 can then communicate wireless communication information stored on the data storage component to the bedside monitor 916, such as a password, unique identifier, channel, or other data information.

Figure 11:
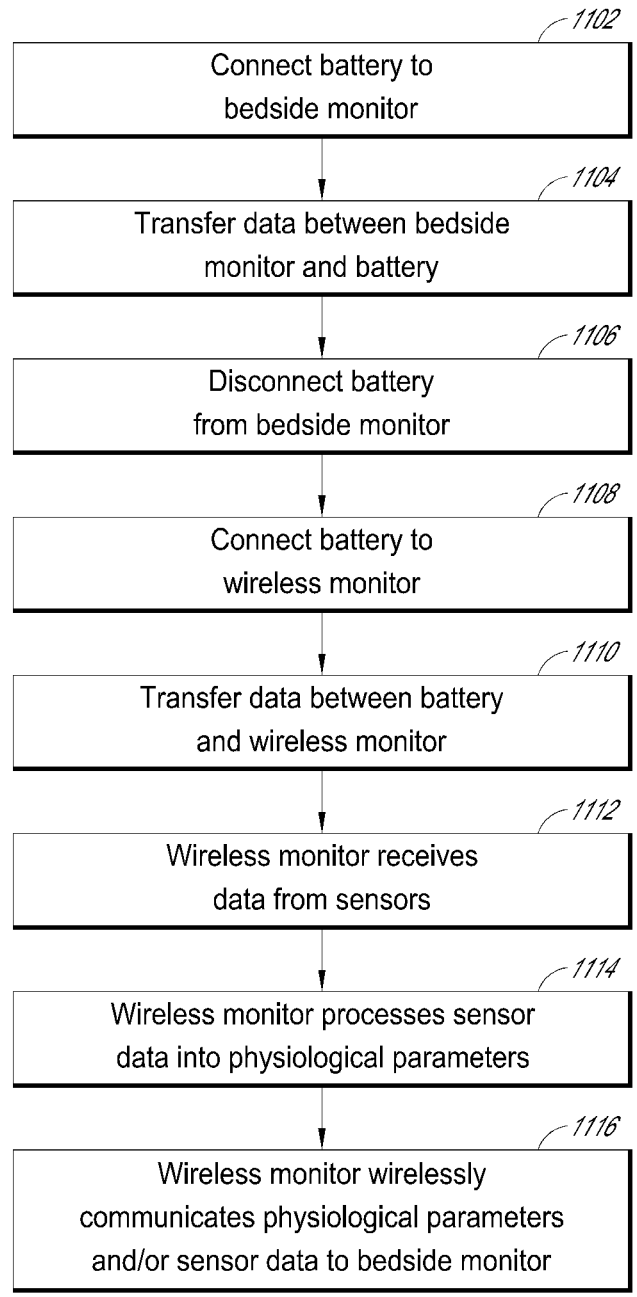
FIG. 11 illustrates one embodiment of a method of using a wireless patient monitoring system.

FIG. 11 illustrates an embodiment for using the wireless patient monitoring system that can be used in connection with any wireless patient monitoring system described herein. The operator connects the removable battery to the bedside monitor (block 1102) and the bedside monitor and the battery communicate wireless communication information with each other (block 1104). The operator then disconnects the battery from the bedside monitor (block 1106) and connects the battery to the wireless monitor (block 1108). The battery and the wireless monitor communicate wireless communication information with each other (block 1110). After the wireless monitor receives data from the one or more sensors (block 1112), the wireless monitor processes the sensor data into representations of physiological parameters (block 1114). The wireless monitor then wirelessly communicates the physiological parameters and/or the sensor data to the bedside monitor (block 1116).

In some embodiments, the data storage component of the battery 904 stores wireless communication information related to the wireless monitor 902. The wireless communication information can be a password, unique identifier, channel, etc. When the battery 904 is engaged with the bedside monitor 916, the bedside monitor 916 can communicate wireless communication information to the battery 904, and the battery 904 can communicate wireless communication information to the bedside monitor 916. The battery 904 is then disconnected from the bedside monitor 16 and connected to the wireless monitor 902. Since the battery 904 already communicated the wireless communication information to the bedside monitor 916, the battery 904 provides all remaining wireless communication information to the wireless monitor. The wireless monitor reconfigures itself according to the information on the battery and no further information is required to be communicated with the bedside monitor 916. This reduces the total number of steps necessary to pair the wireless monitor 902 with the correct bedside monitor 916.

Figure 12:
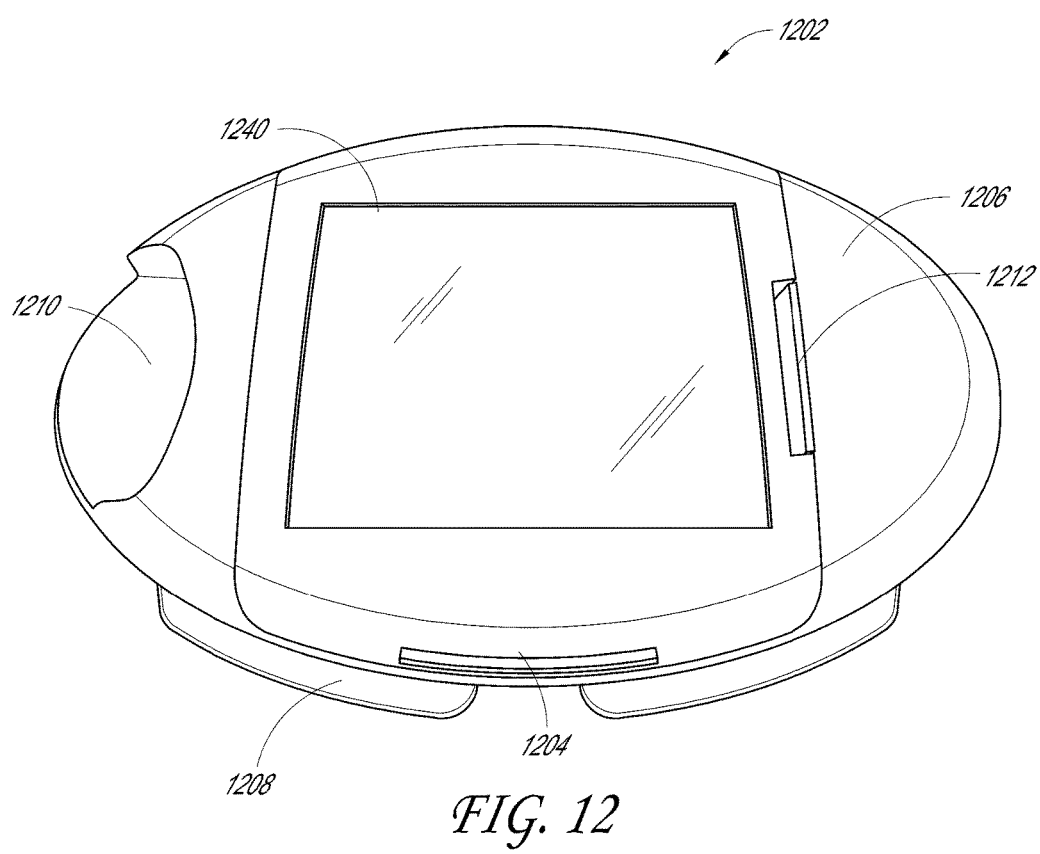
FIG. 12 illustrates a wireless monitor having a display screen.

FIG. 12 illustrates another embodiment of the wireless patient monitor 1202. The features of the wireless patient monitor 1202 can be combined with any of the features of the systems described above. Likewise, any of the features described above can be incorporated into the patient monitor 1202.

As shown in FIG. 12, the wireless patient monitor 1202 can include a housing 1205 that removably engages a battery 1204. The monitor 1202 can include a release mechanism 1212 for releasing the battery 1204 from the housing 1206 and/or one or more outlets 1210 for engaging one or more sensors.

The wireless patient monitor 1202 can include a wireless transceiver capable of transmitting data using any of a variety of wireless technologies, such as Wi-Fi (802.11x), Bluetooth (802.15.2), Zigbee (802.15.4), cellular telephony, infrared, RFID, satellite transmission, proprietary protocols, combinations of the same, and the like.

As shown in FIG. 12, the battery 1204 can include a display screen 1240. The display screen 1240 can indicate any number of parameters, including, but not limited to, physiological parameters, battery levels, and wireless signal strength. Positioning the display screen 1240 on the battery 1204 helps reduce the size of the housing.

The display screen 1240 can include a touch interface to permit a user to access different parameters or settings (e.g., display settings, connectivity settings, etc.). In certain aspects, the display screen 1240 can rotate depending on the orientation of the battery 1204.

To save energy, the display screen 1240 can selectively display certain parameters depending on the location of the battery 1204. For example, if the battery is connected to the bedside monitor or disconnected from the wireless monitor, the battery may only display battery levels. If the battery is connected to the wireless monitor, then the battery may display additional parameters other than battery levels.

Figure 13:
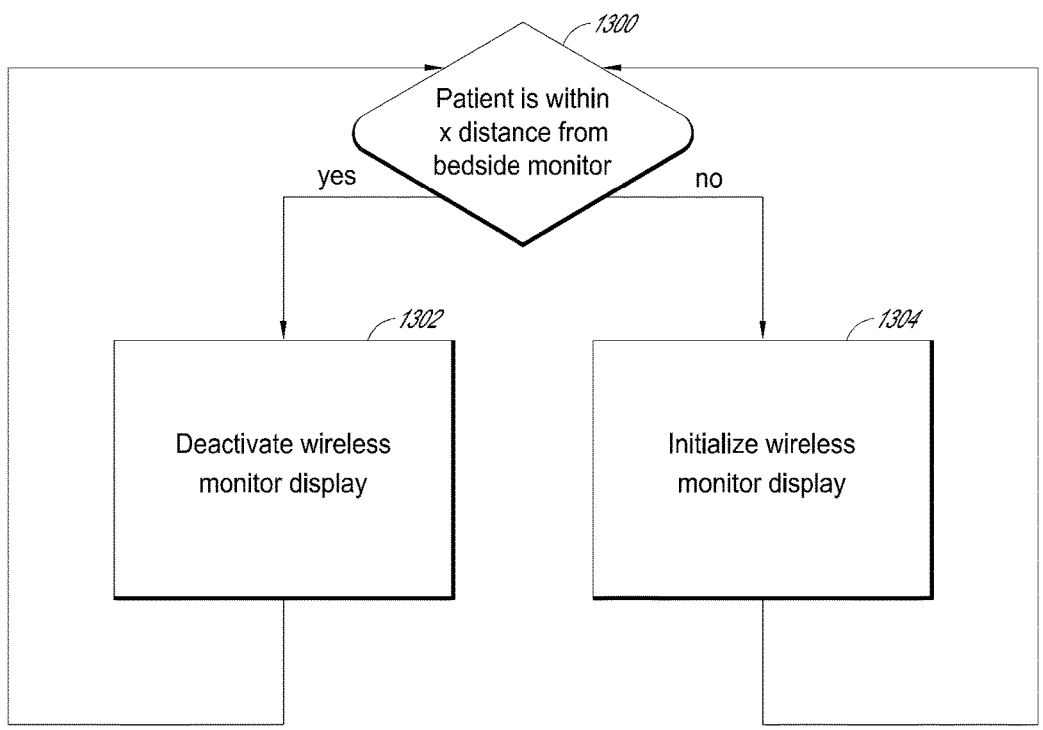
FIGS. 13-15 illustrate methods of using a wireless monitor having a display screen.

The display screen 1240 can selectively display certain parameters depending on the distance between the wireless monitor 1202 and the bedside monitor 1216. Referring to FIG. 13, if the wireless monitor 1202 is within a predetermined distance from the bedside monitor—(block 1300), then the display screen 1240 deactivates (block 1302). If the wireless monitor 1202 is not within a predetermined distance from the bedside monitor (block 1300), then the display screen 1240 initializes (block 1304). The display screen 1240 only needs to be active when the patient is not close to the bedside monitor.

Figure 14:
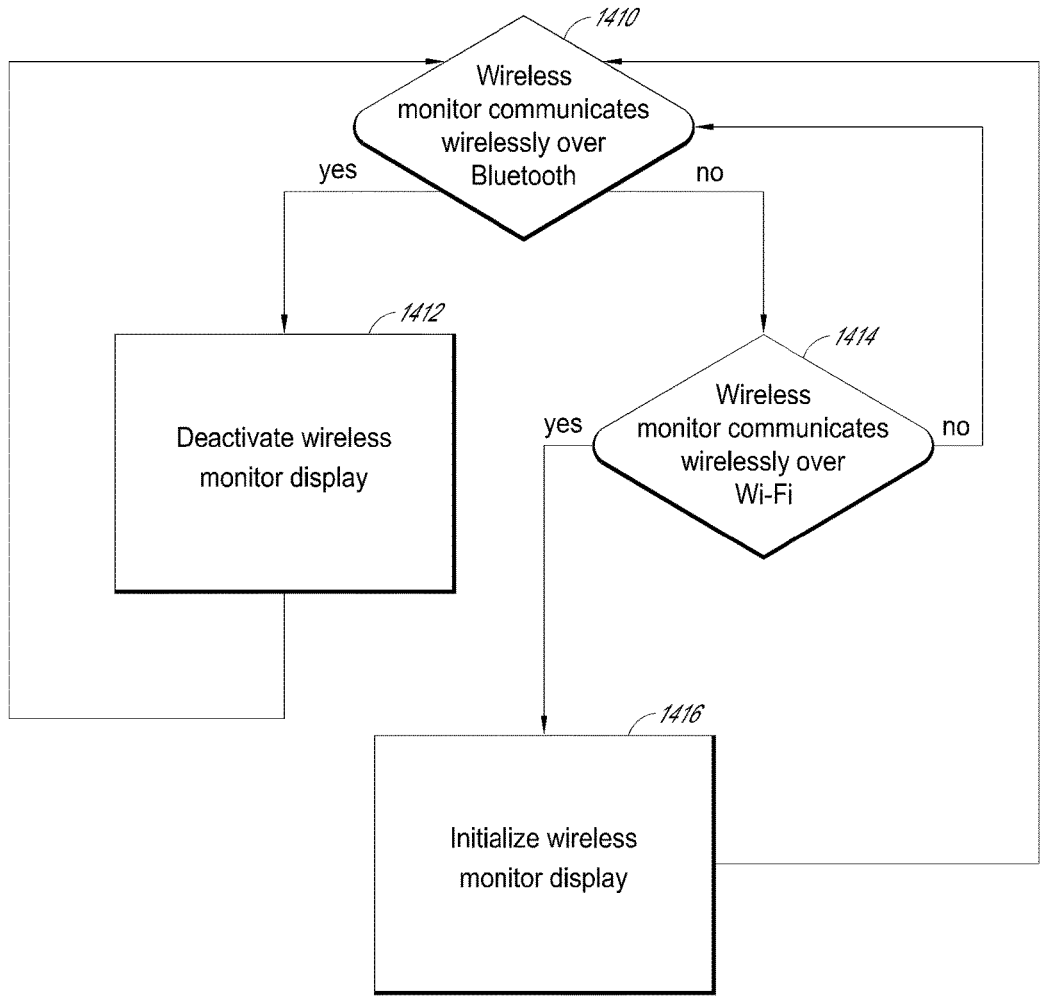

The display screen 1240 can selectively display certain parameters depending on the type of wireless connection between the wireless monitor 1202 and the bedside monitor and/or hospital IT infrastructure. Referring to FIG. 14, if the wireless monitor 1202 wirelessly communicates physiological parameters and/or sensor data over Bluetooth (block 1410), then the display screen deactivates (block 1412). If the wireless monitor 1202 wirelessly communicates physiological parameters and/or sensor data over Wi-Fi (block 1414), then the display screen 1240 initializes (block 1416).

Figure 15:
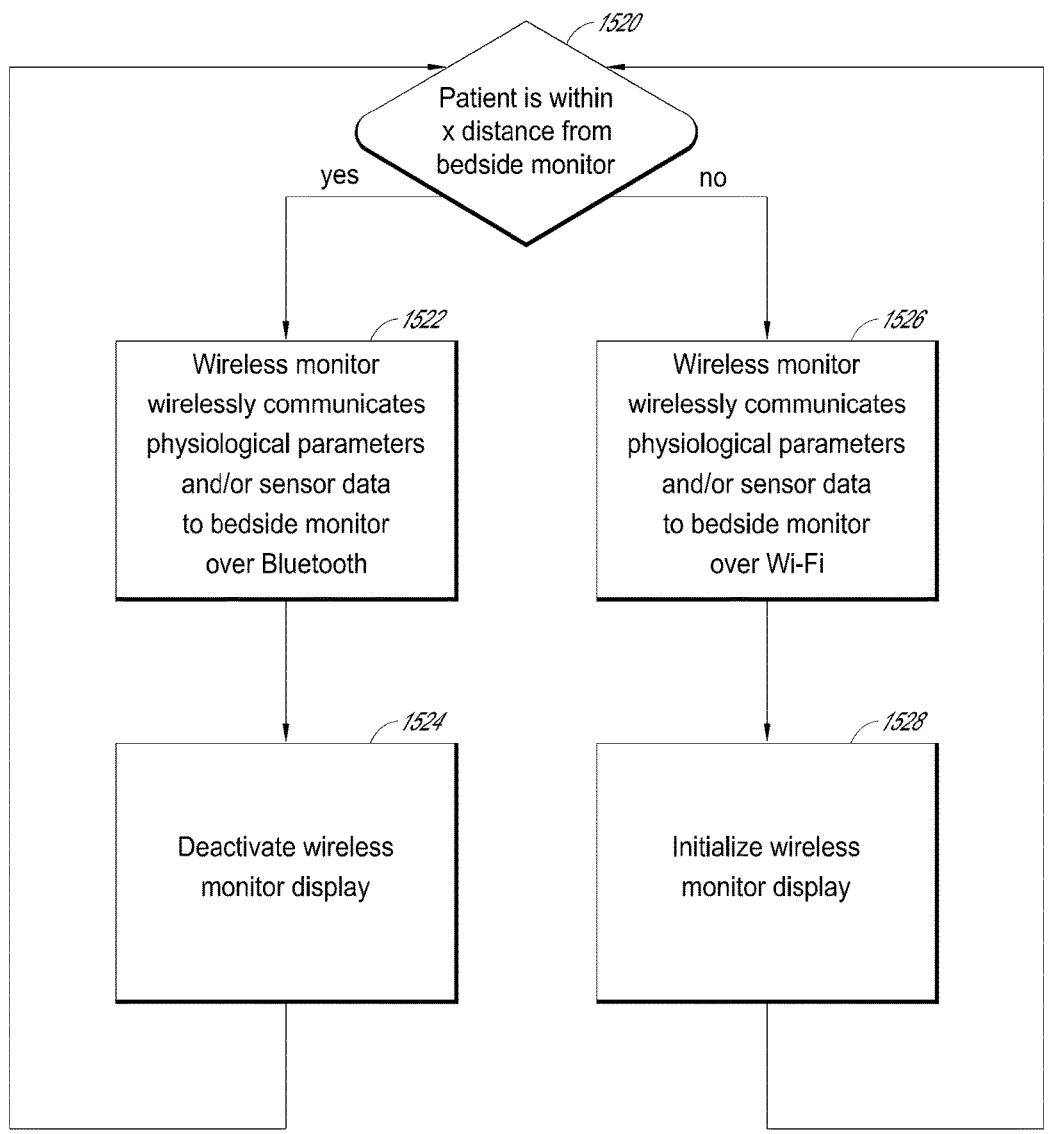

The wireless monitor 1202 can selectively transmit information over different wireless connections and display certain parameters depending on the distance between the wireless monitor 1202 and the bedside monitor. Referring to FIG. 15, if the wireless monitor 1202 is within a predetermined distance from the bedside monitor (block 1520), then the wireless monitor 1202 wirelessly communicates physiological parameters and/or sensor data to the bedside monitor over Bluetooth (block 1522). If the wireless monitor 1202 wirelessly communicates to the bedside monitor over Bluetooth (block 1522), then the display screen 1240 deactivates (block 1524). The display screen 1240 does not need to be active since the bedside monitor is nearby.

If the wireless monitor 1202 is not within a predetermined distance from the bedside monitor (block 1520), then the wireless monitor 1202 wirelessly communicates physiological parameters and/or sensor data to the bedside monitor over Wi-Fi (block 1526). If the wireless monitor 1202 wireless communicates to the bedside monitor over Wi-Fi (block 1526), then the display screen 1240 initializes (block 1528). If the wireless monitor 1202 is communicating over Wi-Fi, then it is more likely that the patient is not in the patient room. In that case, it is necessary to have a secondary display screen available to monitor the patient's physiological parameters.

Although FIGS. 14 and 15 were discussed in reference to Bluetooth and Wi-Fi, the system can wirelessly communication information over ZigBee or cellular telephony. Also, the system may convert from a first wireless technology (e.g., Bluetooth) to a second wireless technology (Wi-Fi) based on signal strength rather than distance.

The wireless monitor 1202 can help the hospital staff monitor the patient when the patient is not close to the bedside monitor. When the patient is close to the bedside monitor, the bedside monitor will notify the staff if any of the patient's physiological parameters are irregular by activating an audible alarm and/or by alerting a staff member using the hospital IT infrastructure. When the patient is more than a pre-determined distance from the bedside monitor, the wireless monitor 1202 can send the physiological parameters and/or sensor data directly over the hospital IT infrastructure, so the hospital staff can continuously monitor the patient at the nurse's station or any other location. If the patient exhibits any irregular physiological parameters, the wireless monitor 1202 can activate an audible alarm and/or alert a staff member using the hospital IT infrastructure. The wireless monitor 1202 can use triangulation to provide the location of the patient, so the staff member can quickly find the patient. By configuring the wireless monitor 1202 to process the sensor data, the wireless monitor 1202 is capable of communicating physiological parameters over the hospital IT infrastructure without the bedside monitor.

Any of the systems described herein can include a display screen and can be configured to carry out any of the methods described in FIGS. 13-15.

FIGS. 16A-F illustrate another embodiment of a wireless patient monitoring system. The features of the wireless patient monitoring system can be combined with any of the features of the systems described above. Likewise, any of the features described above can be incorporated into the wireless patient monitoring system.

Figure 16A:
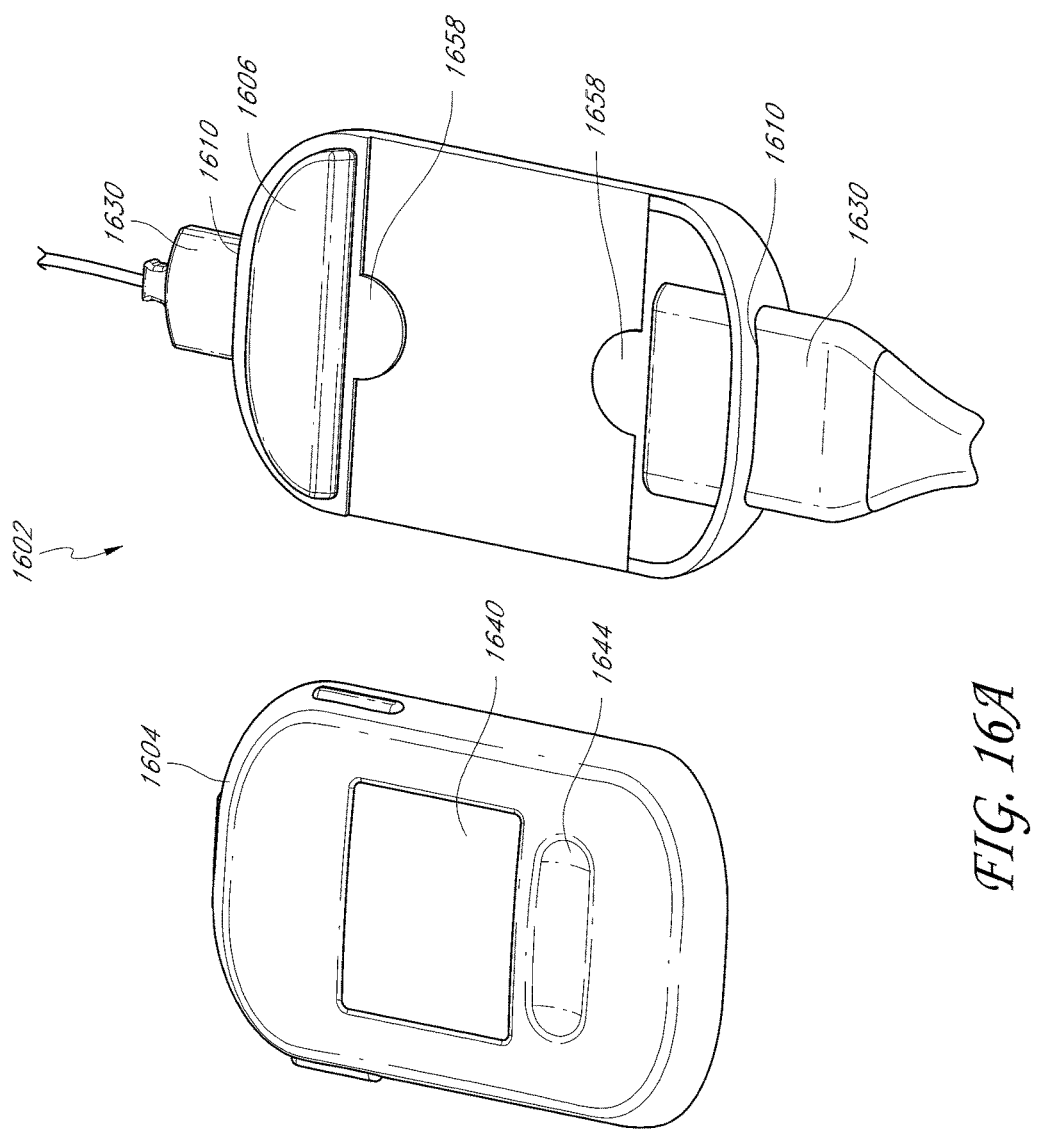

FIG. 16A illustrates the wireless monitor 1602 with the battery 1604 detached from the base 1606. The base 1606 can include processing and wireless transmission capabilities and/or share processing function with the battery 1604. The battery 1602 removably engages an anterior surface of the base 1606. The battery 1602 can engage the housing 1602 via a magnet, a clip, a band, a snap fit, a friction fit, or otherwise. The housing 1602 can include one or more outlets 1610 for engaging one or more sensors 1630. As shown in FIG. 16A, the housing 1206 can include an outlet on one end of the housing and another outlet on the opposite end of the housing. Disposing outlets on opposite ends of the housing can be useful to prevent sensor cables from tangling.

The battery 1604 can include a display screen 1640 and a user input device 1644. The user input device can activate the screen, adjust display settings, select physiological parameters to display, and/or otherwise control the display screen 1640. As shown in FIG. 16A, the user input device 1644 can be a touch pad. A user can tap the touch pad to select a feature and/or swipe in different directions to change selections. For example, the user can swipe right or left to change the parameters displayed on the display screen. Other functions can also be performed using the three inputs of the touch pad—left swipe, right swipe, and tap. Other user input devices 1644 can include one or more buttons, switches, or other control. In certain aspects, the display screen can be the user input device.

Figure 16B:
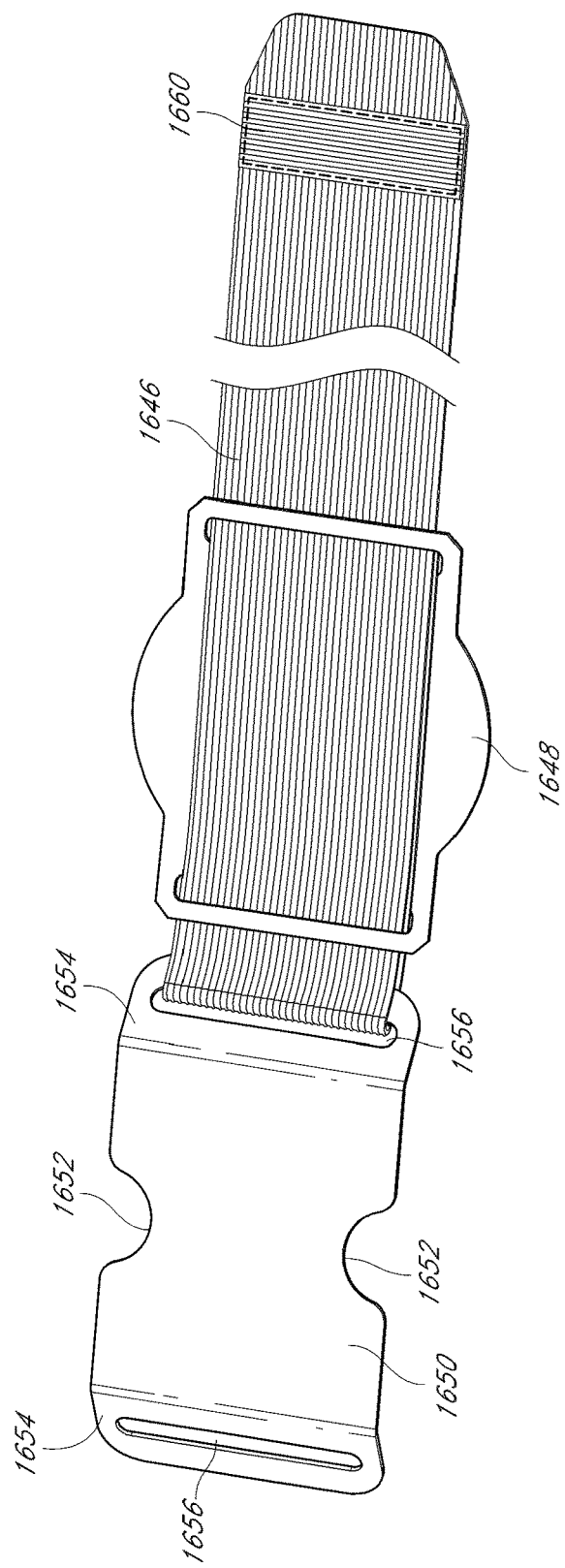

FIG. 16B illustrates a strap 1646 for securing the wireless monitor 1602 to the patient. The strap 1646 can include any fabric, elastic, or otherwise flexible material. In certain aspects, the strap 1646 can be waterproof. One or both ends of the strap 1646 can be tapered. One or both ends of the strap 1646 can include a covering to protect the strap ends.

The strap 1646 can be secured to the patient as an arm band, a shoulder strap, a belt, or in any other configuration. A portion of the strap 1646 can be secured to another portion of the strap 1646 using Velcro 1660, clasps, adhesive, snap-fits, or any other connector. The strap 1646 can include a band (not shown) for securing an excess portion of the strap 1646.

As shown in FIG. 16B, the strap 1646 can include a connector 1650 for engaging the wireless monitor 1602 and an adjustment mechanism 1648 to adjust the length of the strap 1646 and/or secure any excess strap 1646. The connector 1650 can be an integral portion of the strap 1646 or a separately formed component secured to the strap 1646. As shown in FIG. 16B, the connector 1650 can include an opening 1656 on opposite sides of the connector 1650 for securing either end of the strap 1646. One or both ends of the strap 1646 can be removably secured to the connector 1650.

In certain aspects, the connector 1650 engages the housing by being disposed between the base 1606 and the battery 1604. At least a portion of the connector 1650 can overlay a portion of the housing. The connector 1650 can include certain features to mate with a corresponding feature of the base 1606 and/or battery 1604. For example, the connector 1650 can include one or more recesses 1652 configured to mate with one or more protrusions 1658 on the base 1606.

Figure 16C:
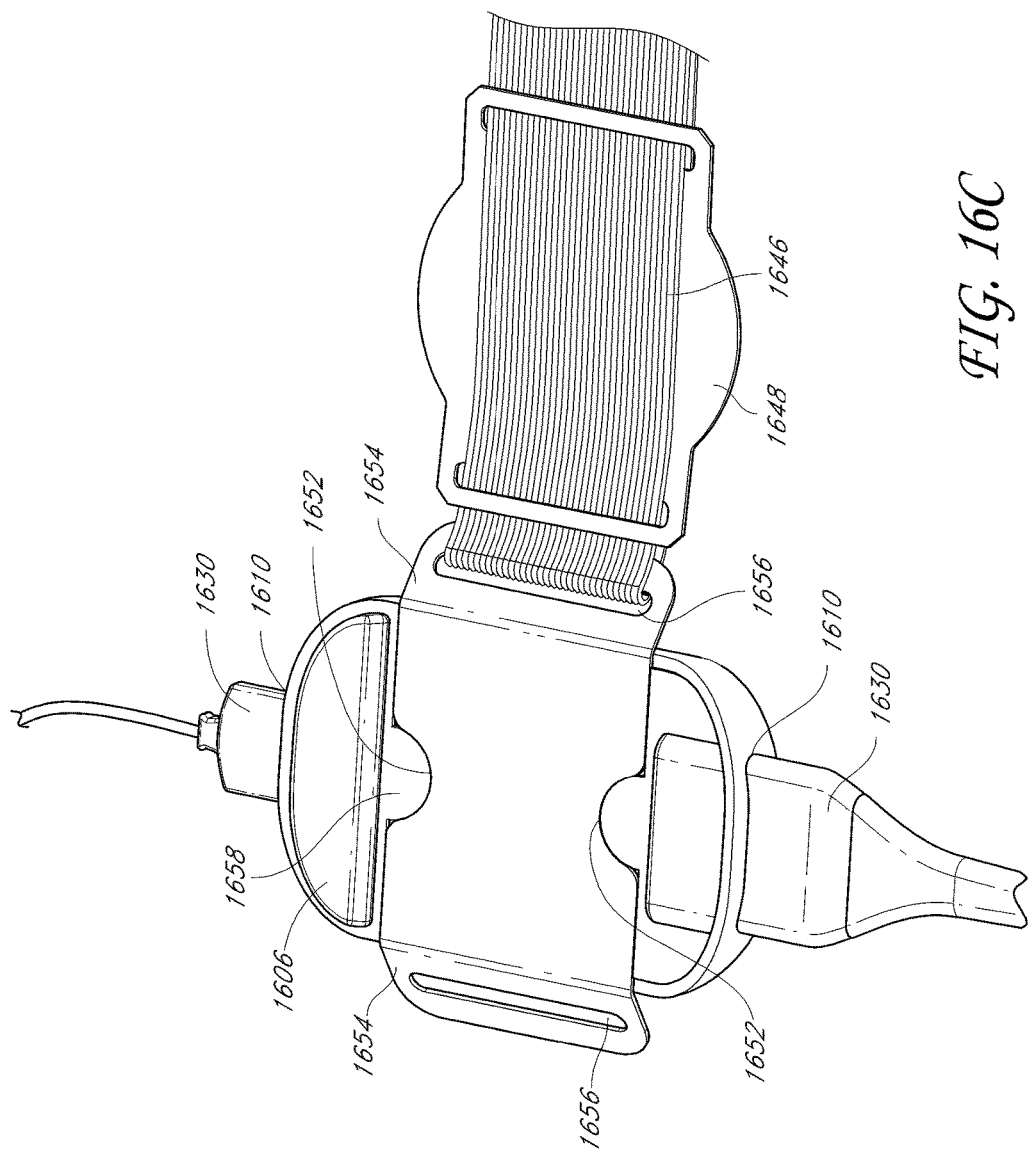

As shown in FIG. 16C, the connector 1650 can include a recess 1652 on opposite ends of the connector 1650 that mate with protrusions 1658 on opposite ends of the base 1606. The connector 1650 can be flush with the protrusions 1658 to provide a flat surface for the battery 1604.

In other aspects, the connector 1650 can pass through an opening of the wireless monitor. For example, as shown in FIG. 12, the wireless monitor can include an opening 1208 for engaging the strap 1646. In still other aspects, the connector 1650 can engage the wireless monitor 1602 using clips, ties, buckles, buttons, or any other connector.

The wireless monitor 1602 can include a wireless transceiver capable of transmitting data using any of a variety of wireless technologies, such as Wi-Fi (802.11x), Bluetooth (802.15.2), Zigbee (802.15.4), cellular telephony, infrared, RFID, satellite transmission, proprietary protocols, combinations of the same, and the like.

Figure 16E:
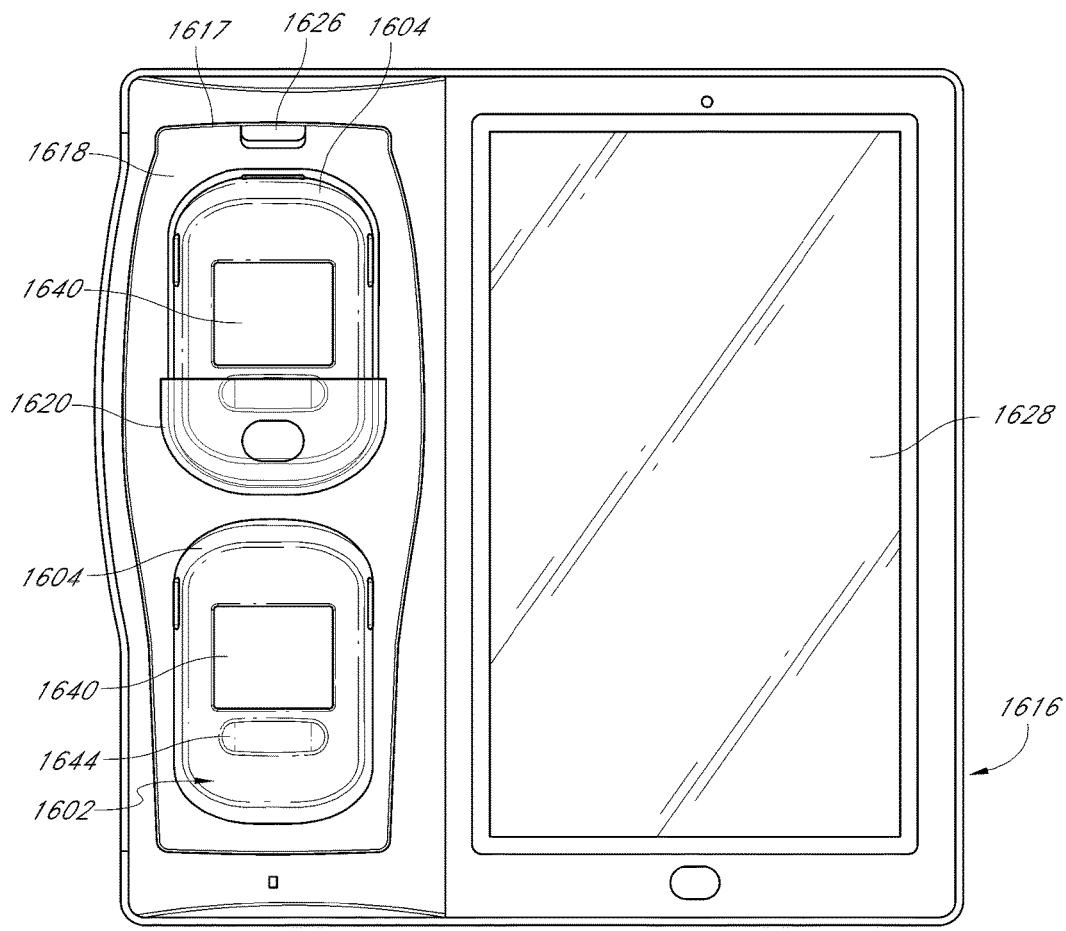
Figure 16F:
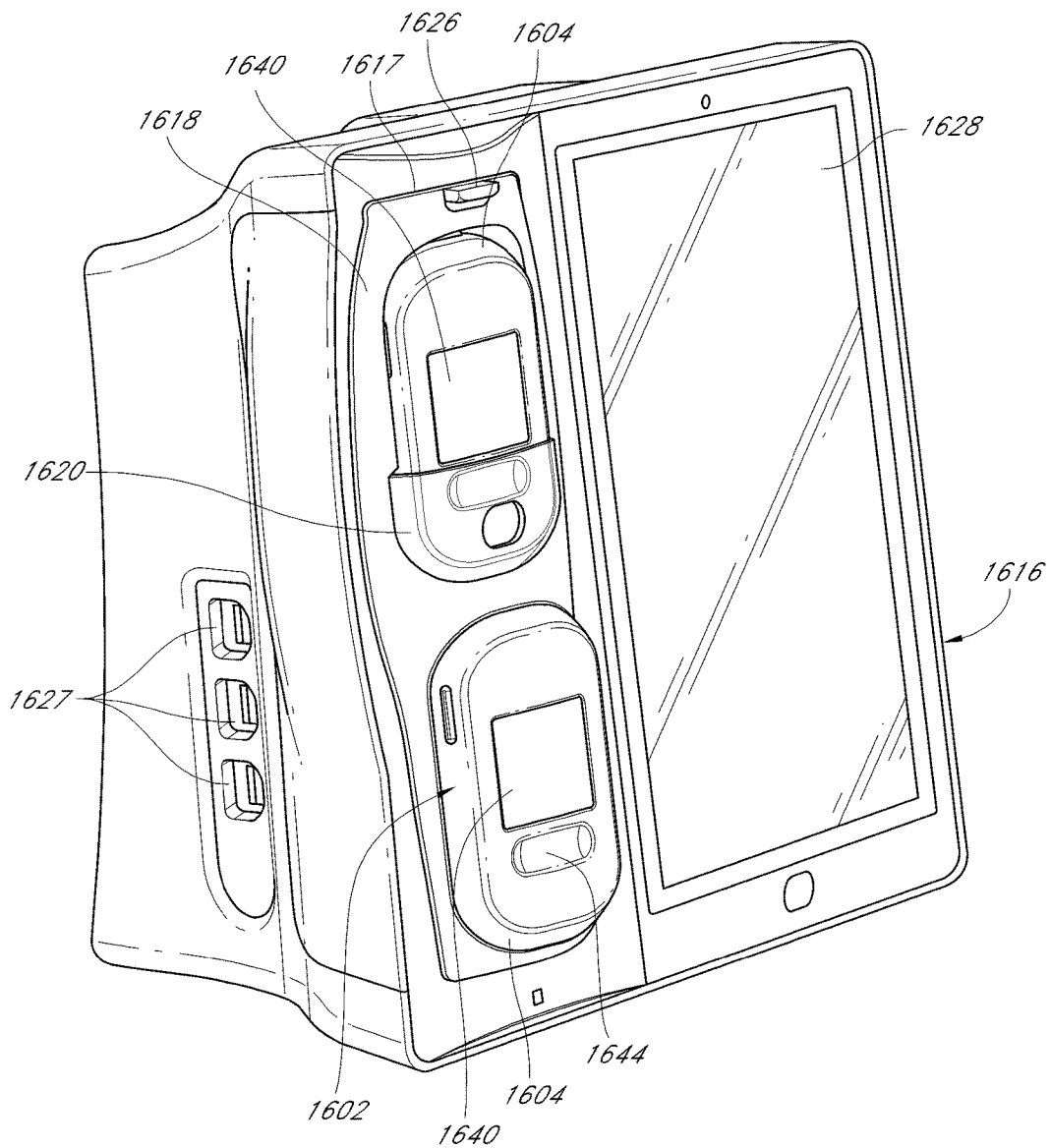
Figure 16G:
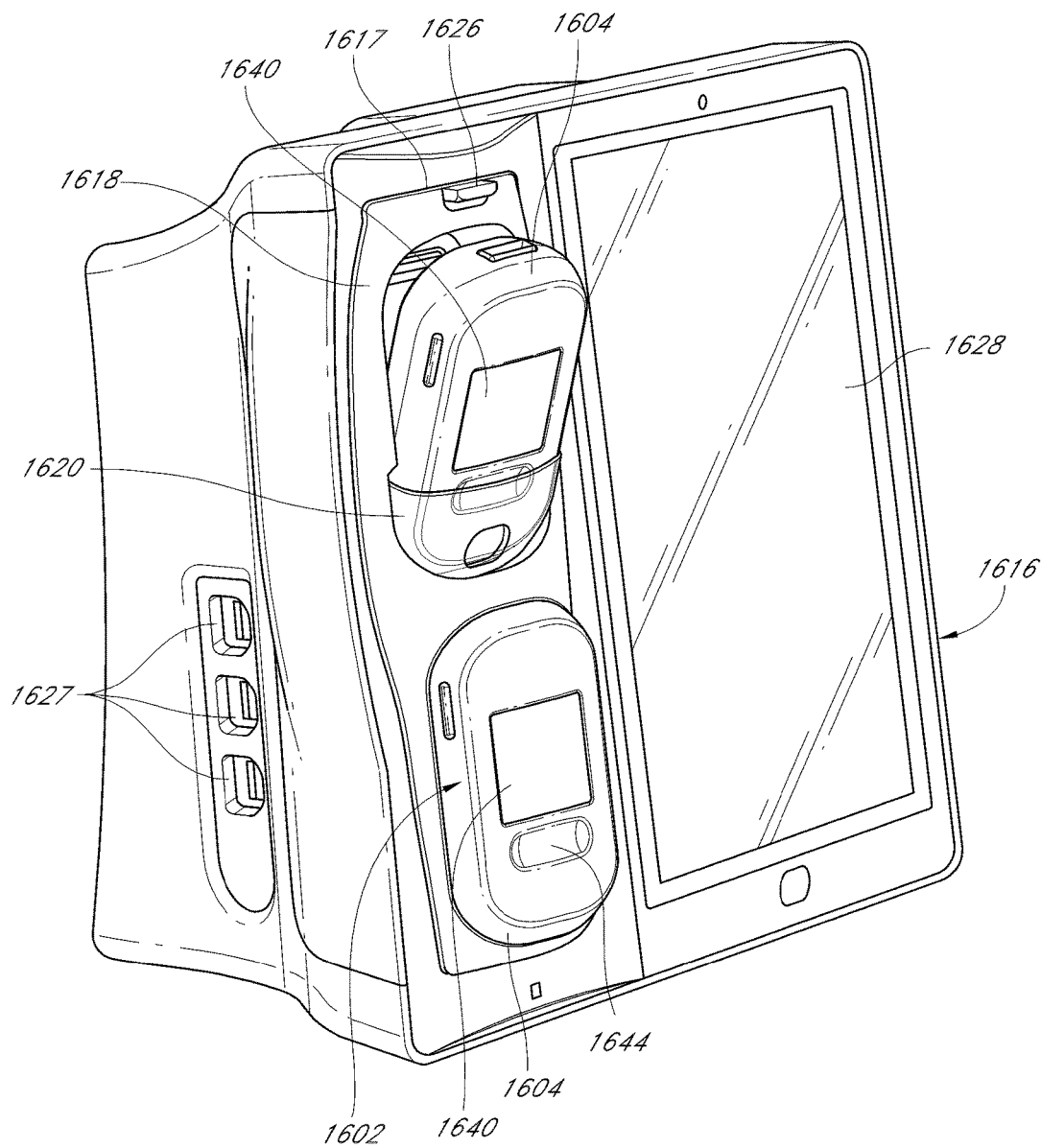

FIGS. 16D-16F illustrate a bedside monitor 1616 configured to receive the wireless monitor 1602. The bedside monitor can include one or more input ports 1627 configured to receive cables. In certain aspects, the bedside monitor 1616 can include a port 1617 configured to receive a handheld device, such as the handheld monitor 166 shown in FIG. 1D. Further details about the handheld device can be found in U.S. application Ser. No. 13/651,167, filed Oct. 12, 2012, entitled "Medical Monitoring Hub," which is hereby incorporated by reference in its entirety.

The port 1617 can removably engage an adapter 1618. For example, the adapter 1618 can include a release mechanism 1626 to release the adapter 1618 from the port 1617. In certain aspects, the release mechanism 1626 is studded, so a user must use one or more tools to release the release mechanism 1626.

The adapter 1618 can be configured to receive a battery 1604 and/or a wireless monitor 1602. The adapter 1618 can include a docking adaptor door 1620 configured to receive the stand alone battery 1604 and/or and a port for receiving a the wireless monitor 1602 including a battery 1604. In certain aspects, as shown in FIG. 16F, the docking adaptor door 1620 can pivot to facilitate insertion and removal of the wireless monitor 1602. When the battery 1604 and/or wireless monitor 1602 having a battery 1604 is physically connected to the adapter 1618, the batteries 1606 can charge and can communicate and/or receive information from the bedside monitor 1616 over a wired connection.

Figure 17A:
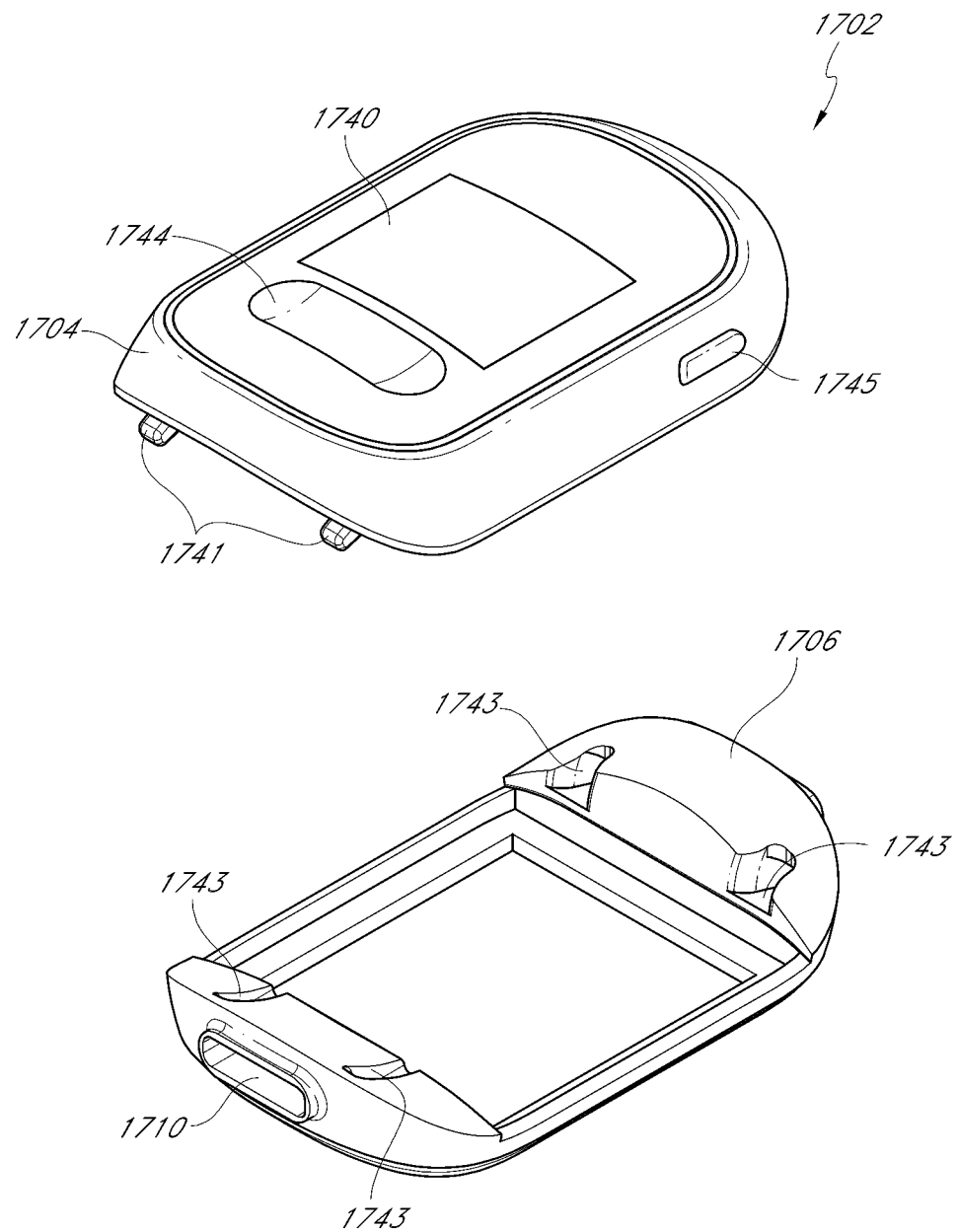
FIGS. 17A-17C illustrate another embodiment of a wireless patient monitoring system.
Figure 17B:
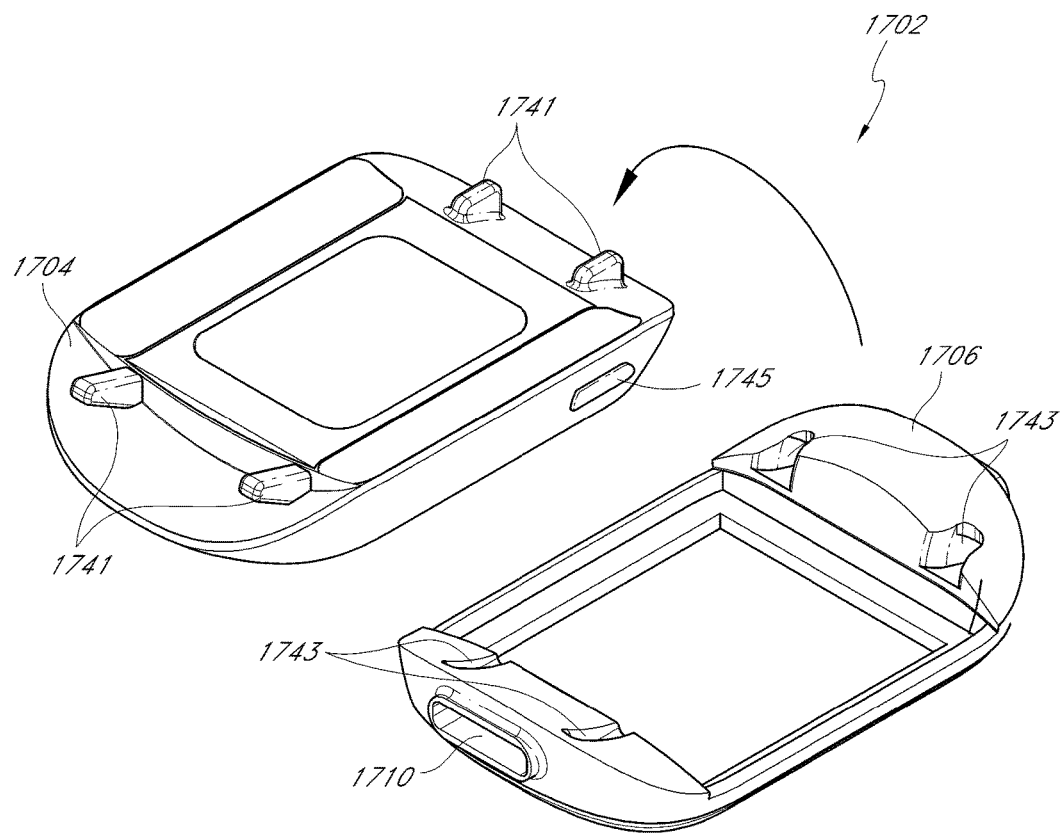
Figure 17C:
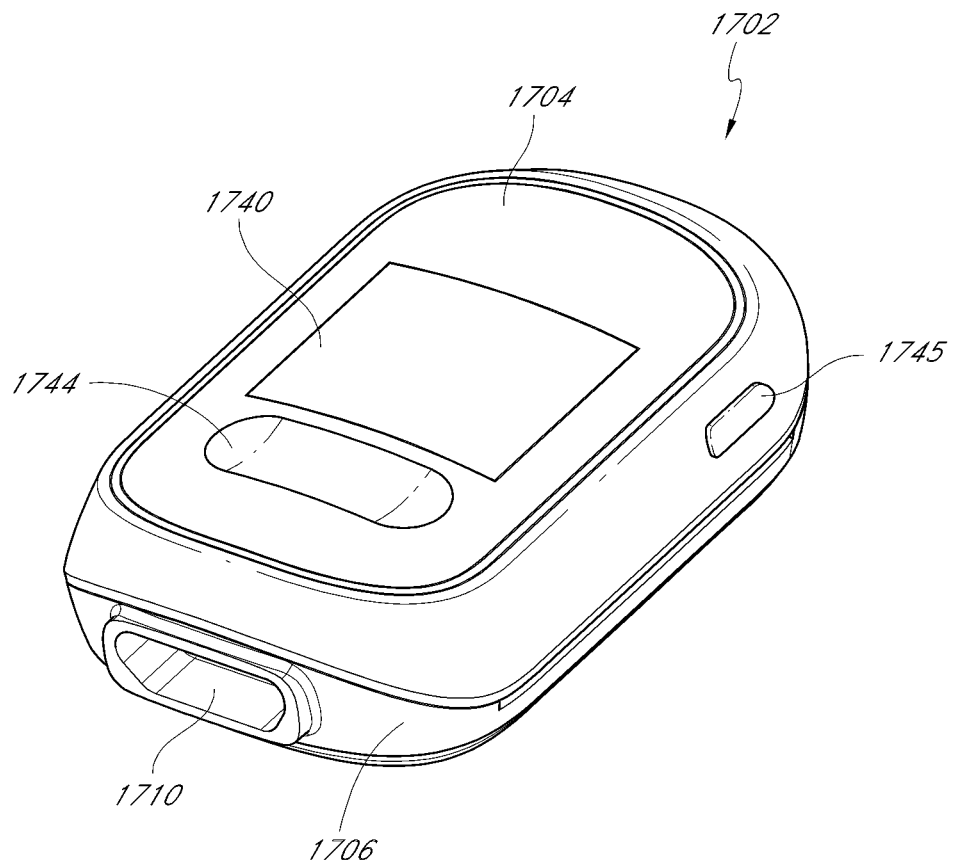

FIGS. 17A-17C illustrate another embodiment of a wireless monitor 1702. The wireless monitor 1702 can include any of the other wireless monitor features described herein. Likewise, any of the other wireless monitor embodiments discussed herein can include any of the features of the wireless monitor 1702.

The wireless monitor 1702 can include a battery 1704 removably engaged with a base 1706. The base 1706 can include processing and wireless transmission capabilities and/or share processing function with the battery 1704. FIG. 17A illustrates an exploded view of the wireless monitor 1702. The housing can include one or more outlets 1710 configured to connect to one or more sensors (not shown). The battery can include a display 1740 capable of displaying physiological parameters, connectivity information, and/or other content. The battery 1704 can include a touch pad 1744 or other user input device. The touch pad 1744 can permit the user to swipe right, swipe left, or tap to control the wireless monitor 1702. The battery 1704 can include an additional user input device (e.g., button 1745) that can activate/deactivate the wireless monitor or provide other functionality.

The battery can include one or more protrusions, ribs, struts, detents, or the like configured to be received in corresponding grooves, notches, recesses, openings, or the like in the base 1706. FIG. 17B illustrates views of an inner portion of the battery 1704 and an inner portion of the housing. The battery 1704 can include two protrusions 1741 on each end of the battery 1704 and along an inner portion of the battery 1704. One or more of the protrusions 1741 can be a different size or shape from the other protrusions 1741. The base 1706 can include two grooves 1743 on each end of the base 1706 and along an inner portion of the base 1706. Each of the grooves 1743 can be configured to receive one of the protrusions 1741. One or more of the grooves 1743 can be a different size or shape from the other grooves 1743. FIG. 17C illustrates a perspective view of the battery 1704 engaged with the base 1706.

The wireless monitor 1702 can include a wireless transceiver capable of transmitting data using any of a variety of wireless technologies, such as Wi-Fi (802.11x), Bluetooth (802.15.2), Zigbee (802.15.4), cellular telephony, infrared, RFID, satellite transmission, proprietary protocols, combinations of the same, and the like.

As described above, any of the wireless monitoring systems described herein can include an accelerometer or gyroscope that can be used to detect one or more of patient orientation, patient movement, whether the patient is falling, or the like. In certain aspects, the wireless monitoring system can include an alert system to alert the caregiver that the patient is falling, getting out of bed, or otherwise moving in a prohibited manner. The alert can be an audible and/or visual alarm on the monitoring system or transmitted to a caregiver (e.g., nurses' station, pager, home computer, or otherwise).

In certain aspects, the information received by the accelerometer or gyroscope can be used to create an indication and/or animation of patient movement. This animation can be displayed on the patient monitor or transmitted to a nurses station or other off-site location to enable the caregiver to monitor the patient. The animation can be viewed real time and/or be recorded for playback. For example, if an alarm alerts the caregiver that the patient has fallen out of bed, the caregiver can be presented playbacks of one or more of the patient's movement during that period of time.

Figure 18C:
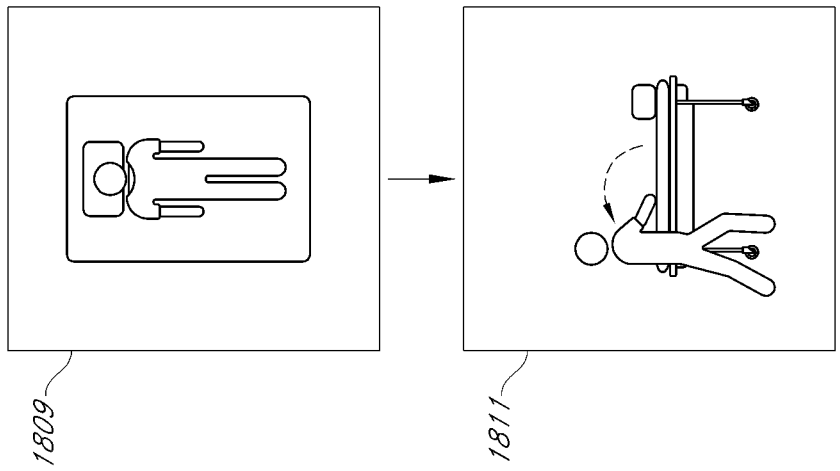
FIGS. 18A-18C illustrate an animation of patient movement created using a wireless patient monitor.
Figure 18B:
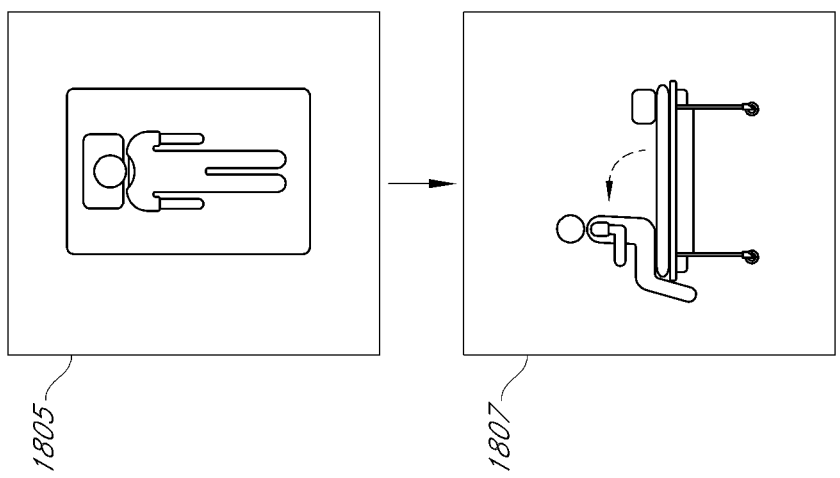
Figure 18A:
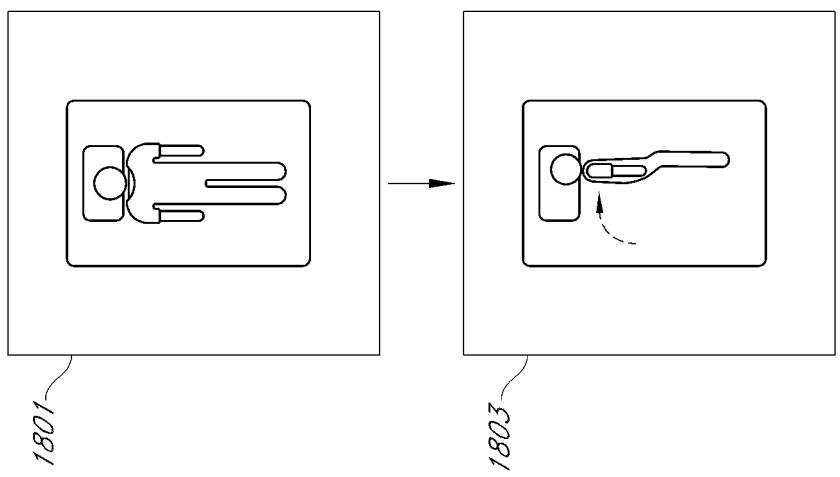

FIGS. 18A-18C illustrate examples of the animation that can be displayed on a bedside monitor, nurses' station monitor, or other display screen. FIG. 18A illustrates a patient lying in bed 1801, and the patient rolling over 1803. FIG. 18B illustrates the patient lying in bed 1805, and the patient sitting up 1807. FIG. 18C illustrates the patient lying in bed 1809, and the patient getting out of bed 1811. Other patient movements can also be illustrated, such as a patient falling, walking, or otherwise.

III. Additional Patient Movement Detection Embodiments

Sometimes unnecessary injuries occur to hospital patients due to falling, whether while walking or falling out of a patient bed. Patient falls can be difficult to detect because rarely do patients fall out of bed quickly, which might be easy to detect as an impact with an accelerometer. Rather, patients often tend to slide out of bed more slowly, resulting in accelerometer outputs that may not register any hard impact.

Another problem sometimes occurring in hospitals results from lack of patient movement, which can result in bedsores (sometimes called pressure sores). Bedsores often result from patients maintaining the same position in bed (or in a chair) over an extended period of time. If left untreated, bedsores can result in life-threatening staph infections. Nurses may attempt to prevent bedsores by instructing patients to turn over, get up, or manually turning patients with limited mobility from time to time. However, with increasingly large workloads, it can be difficult for hospital staff to keep track of each patient's turning/movement schedule to prevent bedsores.

Advantageously, in certain embodiments, a patient movement detector can address these and other issues. The patient movement detector may receive inputs from position sensors, a thermal imaging camera, a video camera, and/or triangulation data. Based on one or more of these inputs, the patient movement detector can perform one or more of the following: fall prevention detection, bedsore prevention analysis, patient location detection, and patient walk test scoring. The patient movement detector can, for example, output a fall warning alarm, a bedsore warning alarm, patient location information, and/or walk test scores.

Figure 19:
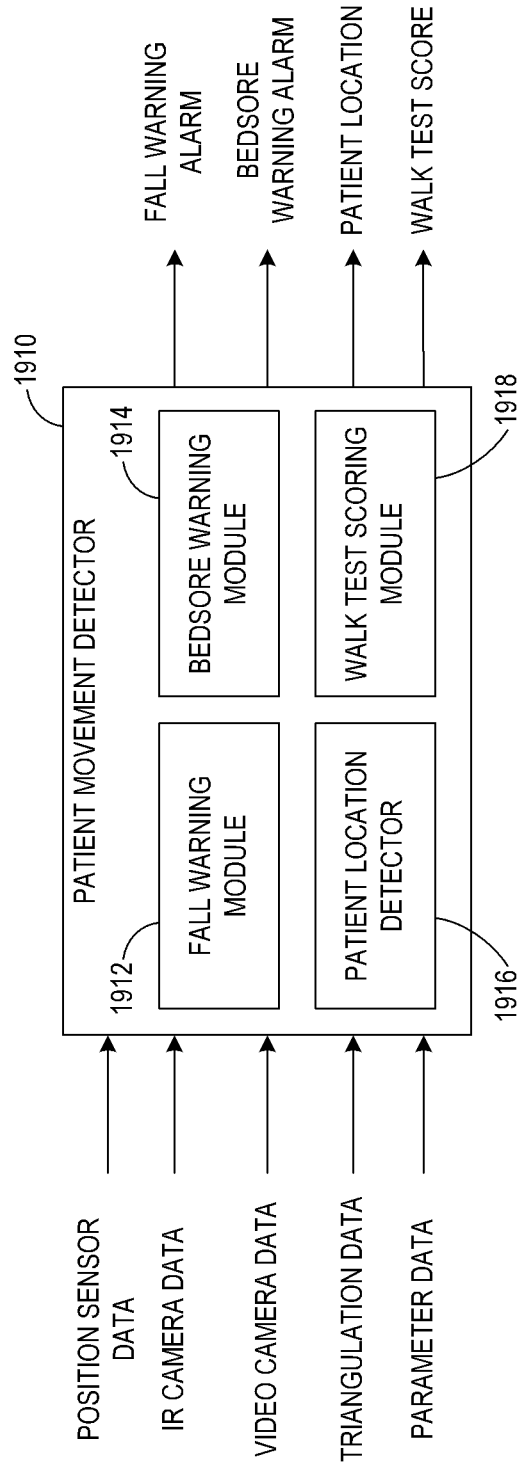
FIG. 19 depicts an embodiment of a patient movement detector.

An example patient movement detector 1910 is shown in FIG. 19. The patient movement detector 1910 includes a fall warning module 1912, a bedsore warning module 1914, a patient location detector 1916, and a walk test scoring module 1918. In addition, the patient movement detector 1910 receives inputs, including position sensor data, infrared (IR) or thermal imaging camera data, video camera data, triangulation data, and physiological parameter data. In response to one or more of these inputs, the patient movement detector 1910 outputs a fall warning alarm, bedsore warning alarm, the patient's location, and a walk test score. Some of the inputs to the patient movement detector 1910 may be omitted in some embodiments. Likewise, any of the modules may be omitted, and some of the outputs may be omitted as well.

In general, the patient movement detector 1910 can include hardware and/or software, such as hardware processor comprising digital logic circuitry, a memory, and the like for performing the tasks described herein, among possibly others. The patient movement detector 1910 can be implemented by any of the patient monitoring systems or devices, including wireless devices, described herein. In an embodiment, however, the patient movement detector 1910 is implemented by the multi-patient monitoring system 640 described above. For instance, the patient movement detector 1910 can be implemented in a central hospital server or clinical facility server or the like. In other embodiments, the patient movement detector 1910 can be implemented by a bedside device that communicates wirelessly with any of the patient-worn monitoring systems described above.

For instance, the patient-worn monitoring system can send the patient movement detector 1910 position sensor data from an accelerometer, gyroscope, or compass in the patient-worn monitoring system. The IR camera data and/or video camera data can be sent to the patient movement detector 1910 from an IR camera and/or video camera installed at or in the bedside device or elsewhere in the patient's room. The IR camera and video camera may be implemented in a single device. Triangulation data can be provided to the patient movement detector 1910 from wireless access points in a hospital, for example, wherever a patient's wireless transceiver (e.g., the patient-worn monitoring system) is detected. Further, the patient-worn monitoring system can transmit physiological parameter data to the patient movement detector 1910.

However, in other embodiments, the patient movement detector 1910 can operate at least in part without interacting with a patient-worn monitoring system. Instead, the patient may be coupled with a bedside monitoring device via sensors connected to the bedside monitoring device or wirelessly. The bedside monitoring device may implement the patient monitoring detector 1910. One or more position sensors may be integrated with one or more of the physiological sensors coupled with the patient. Alternatively, the position sensors are omitted and the patient movement detector 1910 uses IR camera data and/or video camera data to perform patient movement detection.

The fall warning module 1912 can help prevent patient falls by anticipating falls before they are about to occur. In an embodiment, the fall warning module 1912 performs fall prevention detection for patients who are marked as high risk for falling (e.g., in an EMR system). Alternatively, the fall warning module 1912 performs fall prevention detection for all patients. The fall warning module 1912 may also detect when a fall has occurred. In either case (actual fall or predicted potential fall), the fall warning module 1912 can issue an audible and/or visual alarm, which may also be sent over a network, to one or more clinicians regarding a possible fall or actual occurrence of a fall.

The fall warning module 1912 can analyze IR camera data to determine whether a fall has occurred in one embodiment. For instance, the fall warning module 1912 can monitor the IR image data for changes in thermal temperature in the IR image. If the temperature detected in the image, which may be represented by pixel intensity or luminosity, drops, then the fall warning module 1912 can sound an alarm. This drop in IR temperature can be indicative of the patient leaving the bed (e.g., by falling) or having already left the bed. Other embodiments are also described below with respect to FIG. 20.

The fall warning module 1912 may also detect potential falls based on position sensor data from an accelerometer, gyroscope, or compass. Any of these devices can provide outputs that reflect changes in patient position. For instance, the gyroscope can output motion data indicative of an orientation of the patient or a rotation of the patient. The fall warning module 1912 can analyze the changes in patient position, such as changes in the orientation or rotation of the patient, to predict an upcoming fall and alarm accordingly. In one example, the fall warning module 1912 can determine that the changes in the orientation or rotation of the patient suggest that the patient performed a sideways roll or partial sideways roll where the patient rotated in the bed while the patient's body remained parallel to the surface of the bed. Such a sideways roll or partial sideways roll can be indicative of an elevated risk that the patient subsequently leaves the bed in an unsafe manner. More generally, the fall warning module 1912 can determine whether a portion of the patient to which the position sensor is attached has rolled or turned a certain amount and alarm accordingly if that amount is indicative of a potential fall or actual fall.

Moreover, the fall warning module 1912 may also perform sensor fusion or parallel analysis of sensor inputs to improve fall prevention and/or fall detection. For instance, the fall warning module 1912 can analyze both position sensor data and IR camera data. If both the position sensor data and IR camera data indicate that the patient may be falling or has fallen, the fall warning module 1912 can have greater confidence that a fall has occurred or is about to occur. Accordingly, in one embodiment, the fall warning module 1912 alarms a fall warning alarm if both the position sensor data and the IR camera data indicate that a fall may have occurred or may be about to occur. In another embodiment, the fall warning module 1912 calculates an internal confidence value of a fall based on both the position data and the IR camera data. The fall warning module 1912 can analyze the confidence values to determine whether to alarm, for example, by averaging the confidence values and comparing the average value to a threshold (e.g., above a threshold indicates an alarm should be made). The fall warning module 1912 can also analyze the confidence values by determining that if one of the confidence values is over a threshold, a fall warning alarm should be made. Many other configurations are possible that combine the outputs of the position sensor(s), IR camera data, and the like.

Further, the fall warning module 1912 can use other inputs, such as the triangulation data and/or video camera data to detect falls that are about to occur or that have occurred. Triangulation data, as described above, can be used to detect a patient's position in the hospital or clinical facility (e.g., by the patient location detector 1916). If the triangulation data indicates that the patient is in a single location, not moving, and that position is other than the patient's bed, and the position sensor data indicates that the patient is not moving, and the IR camera data indicates that the bed is empty, or based on another combination of these inputs, the fall warning module 1912 may issue an alarm. IR cameras may also be placed in other locations of the hospital, such as the bathroom, to determine whether a patient is still on a toilet or whether the patient has fallen to the floor (e.g., by analyzing thermal image data of the toilet to determine whether the patient is still on the toilet).

Likewise, the fall warning module 1912 may analyze video camera data to compare images of the patient in the bed and out of the bed, for example, by comparing pixels to determine whether the patient has left the bed. However, if the patient covers himself or herself with a sheet, the video camera image data may be less useful than IR camera data, which can detect thermal energy given off by a patient even when a sheet is over the patient.

Thus, the fall warning module 1912 can use the various inputs to the patient movement detector 1910 to determine whether the patient 1) has left the bed, 2) has rolled over in the bed (and is possibly about to fall), 3) is rolling off the bed, or 4) is on the floor, among many other possibilities. Further, such analysis may also be applied to patients sitting in a chair. In an embodiment, the thermal camera and/or the video camera use motion-tracking algorithms to swivel and track the patient wherever the patient moves within a room. The cameras can output thermal imaging data and/or video camera images to a clinician over a network, for example, by sending the image data to a nurse's station computer, a clinician device, or to a server that can send the image data to the nurse's station computer or clinician device.

The bedsore warning module 1914 can perform similar analysis as the fall warning module 1912, with one difference being in one embodiment that the bedsore warning module 1914 looks for lack of movement in the patient to predict whether the patient has been in one place too long. If the patient has been in one place too long or in one position too long, the patient may be at risk for developing a bedsore, whether the patient is in a bed or in a chair. The bedsore warning module 1914 can therefore analyze the IR image data, position sensor data, and/or triangulation data (and/or video camera data) to determine whether the patient has not moved for a period of time. As above, the bedsore warning module 1914 can compute the change of a patient not moving based on one of these inputs or based on a plurality of these inputs. The bedsore warning module 1914 can also compute a confidence that the patient has not moved. Either the fall warning module 1912 or the bedsore warning module 1914 can output their respective calculated confidence values or scores for presentation on a display to a clinician.

The bedsore warning module 1914 can compare the amount of time that a patient has not moved or has moved only a small amount to a threshold. If the threshold is met or exceeded, the bedsore warning module 1914 can trigger an audible and/or visual alarm (which may also be sent to a clinician over a network). The alarm can remind the clinician to check the patient and possibly move the patient or instruct the patient to move (e.g., by rolling over in bed or by getting up) to reduce the risk of bedsores.

The patient location detector 1916 may perform any of the patient location detection techniques described above, such as triangulation using triangulation data obtained from different wireless access points in a clinical facility. The patient location detector 1916 can also perform dead reckoning to determine patient position based on the position sensor data. Accelerometer or gyroscope data can be integrated, for instance, by the patient location detector 1916 to detect approximate patient position, speed, distance traveled, and so forth. Likewise, the triangulation techniques described herein may detect approximate patient position, speed, distance traveled, and so forth. Sometimes, position sensors drift, and accordingly, position, distance, and/or speed can become inaccurate over time. Accordingly, the patient location detector 1916 can update the position, distance, and/or speed information obtained from the position sensor(s) with triangulation information. The triangulation information can therefore act to calibrate the position sensor data in an embodiment.

The walk test scoring module 1918 can compute a walk test score automatically based on an analysis of walking behavior of a patient. Hospitals often administer walk tests to patients to determine whether patients are fit for discharge. For example, a clinician may instruct a patient to walk down a hallway or walk for a set period of time (such as a few minutes). The clinician may then evaluate the patient's walking performance to see whether the patient is well enough to leave the hospital.

In an embodiment, the walk test scoring module 1918 can automate walk test scoring based on any of the inputs to the patient movement detector 1910 described above. For instance, the walk test scoring module 1918 can evaluate the position sensor data or triangulation data to determine a patient's location, distance traveled, and/or speed. If the patient walks a relatively longer distance in a period of time, or if the patient walks relatively faster, the walk test scoring module 1918 can assign a higher score to the patient than if the patient were to walk a shorter distance or walk slower. The walk test scoring module 1918 can be invoked in response to request from a clinician (e.g., through a user interface output on a display) or may instead programmatically monitor a patient whenever the patient walks and update a walk score accordingly. More generally, the walk test scoring module 1918 could instead calculate a general patient movement score, which can reflect any of a variety of factors, including distance traveled in a given time period (such as a day, an hour, etc.), walking speed, degree of patient movement within a bed (which data may be determined in part by the IR or video camera data in addition to or instead of position sensor data), and so forth.

In addition, the walk test scoring module 1918 can use the parameter data to adjust walk test scores. If a patient's respiratory rate or SpO2 are severely adversely affected by walking, the walk test scoring module 1918 can score the test lower than if the respiratory rate or SpO2 (or other parameter values) stay within normal expected limits for patient walking.

Further, in some embodiments, the walk test scoring module 1918 can compute a steadiness of the patient or use a steadiness calculation to adjust the walk test score. The walk test scoring module 1918 may, for instance, detect any wobbling or unsteadiness of the patient when walking or standing using output from a position sensor. The walk test scoring module 1918 may lower the walk test score if the patient is more wobbly or unsteady. Further, the walk test scoring module 1918 or patient location detector 1916 can output a fall warning alarm if the patient appears to be wobbling or unsteady as detected by the position sensor(s).

Figure 20:
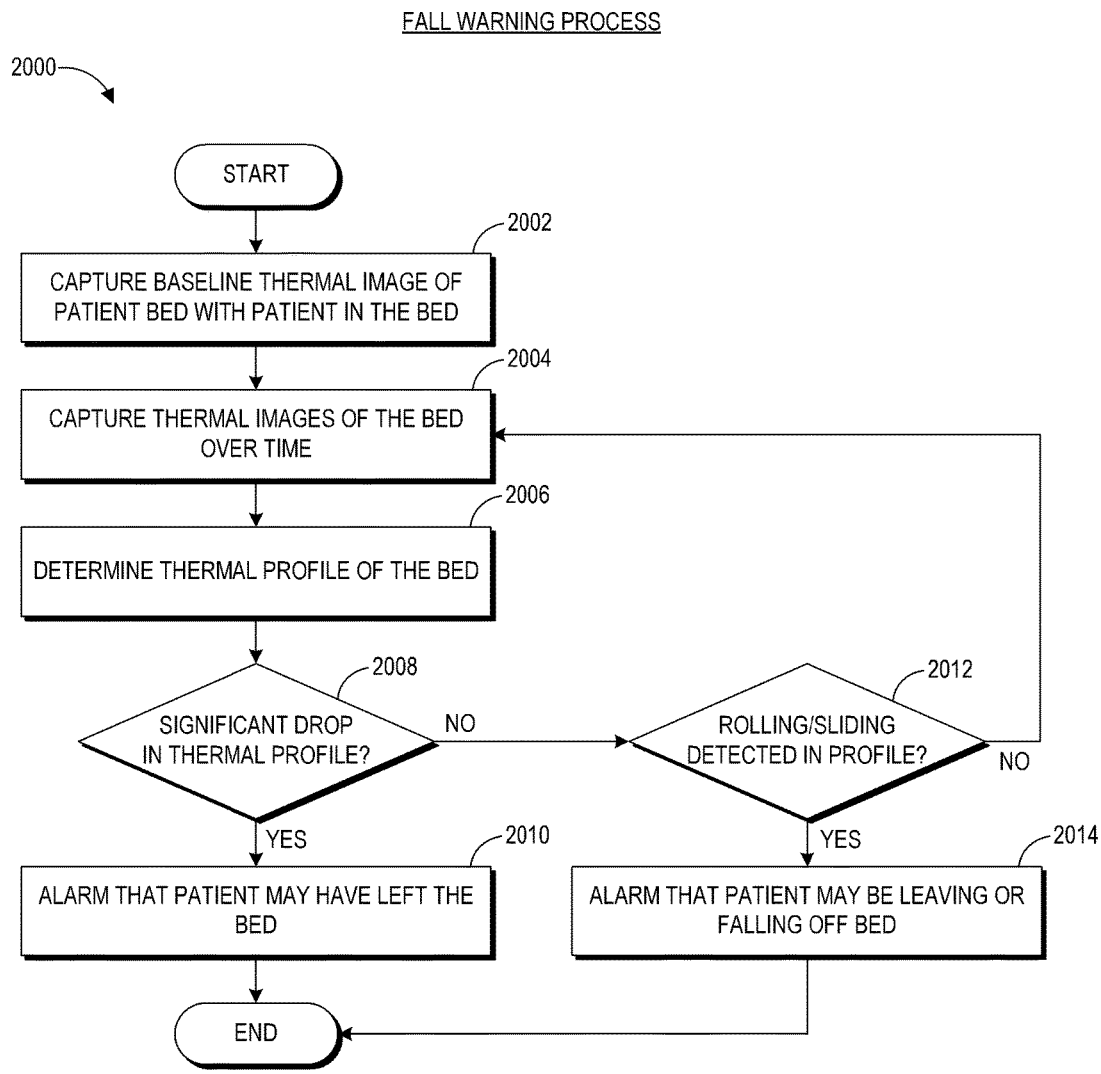
FIG. 20 depicts an embodiment of a fall warning process.

FIG. 20 depicts an embodiment of a fall warning process 2000, which may be implemented by the fall warning module 1912 or any other patient monitoring system.

At block 2002, the fall warning module 1912 captures a baseline thermal image of patient bed with patient in the bed. The fall warning module 1912 then can capture thermal images of the bed over time at block 2004.

At block 2006, the fall warning module 1912 can determine a thermal profile of the bed. The thermal profile may be a value that represents a sum of thermal values from a thermal image. Alternatively, the thermal profile may be represented as a thermal image map of the bed, or a spectrogram of thermal images (e.g., in the frequency or spectral domain).

The fall warning module 1912 can determine at block 2008 whether a significant drop or change in the thermal profile has occurred. For instance, if the sum of thermal values from the thermal image differs significantly from the baseline image, the change may be significant. This analysis may be performed in the frequency or spectral domain, e.g., by analyzing a spectrogram of the thermal imaging data.

If the significant change or drop has occurred, at block 2010, the fall warning module 1912 can trigger an alarm that the patient may have left the bed (or has fallen, or is falling). Thereafter, the process 2000 may end. Otherwise, if the significant change has not occurred, the fall warning module 1912 can detect rolling or sliding in the thermal profile at block 2012. If the patient has moved in the bed, rolling may be inferred, for instance. If the patient's thermal profile indicates movement off the bed, the fall warning module 1912 may infer that the patient is sliding or falling off the bed and alarm that the patient may be leaving the bed at block 2014. The process 2000 may be modified to perform block 2012 or 2008 but not both in one embodiment.

Figure 21:
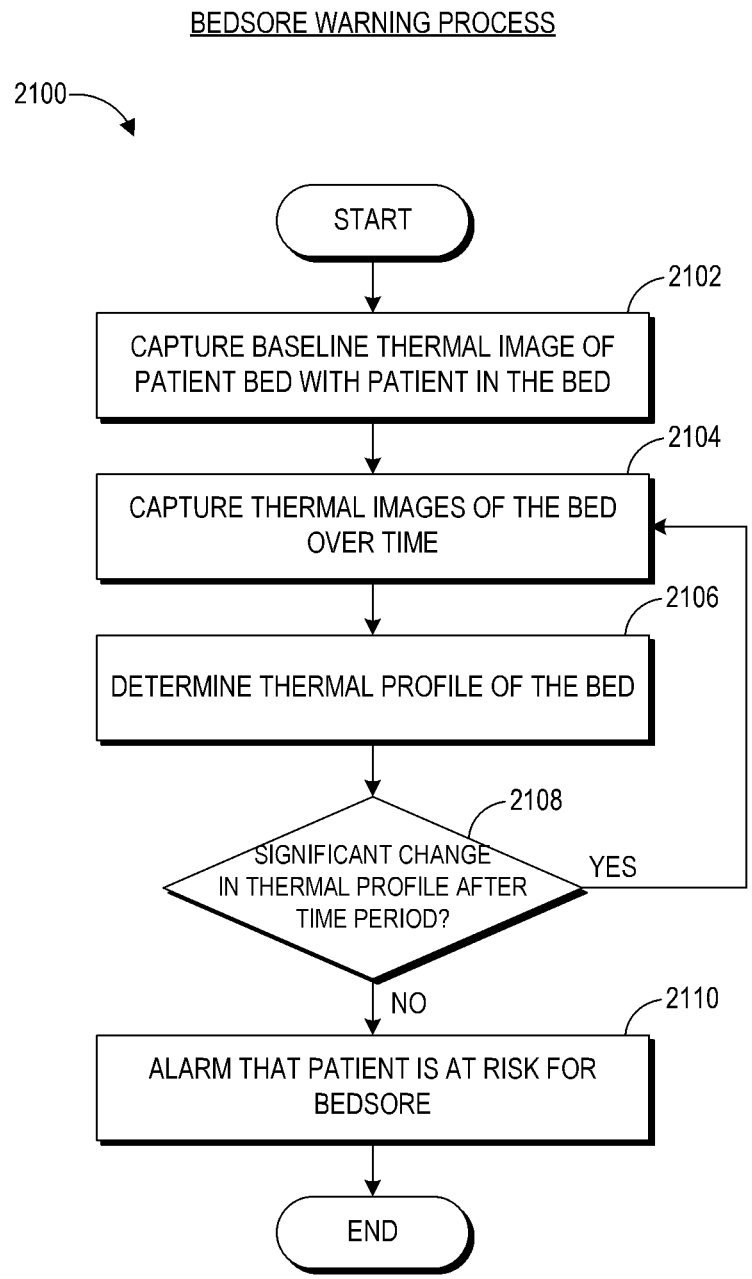
FIG. 21 depicts an embodiment of a bedsore warning process.

FIG. 21 depicts an embodiment of a bedsore warning process 2100, which may be implemented by the bedsore warning module 1912 or any other patient monitoring system.

Blocks 2102 through 2106 of the process 2100 can proceed similarly to blocks 2002 through 2006 of the process 2000. At block 2108, the bedsore warning module 1912 determines whether a significant change in the thermal profile has occurred after a certain time period, which may be minutes, an hour or hours, or the like. The significant thermal change can be indicated by the sum or spectrogram described above. If so, the process 2100 can loop back to block 2104, continuing to capture thermal images and thereby monitoring the patient. If not, the bedsore warning process 2100 can issue an alarm at block 2110.

Figure 22:
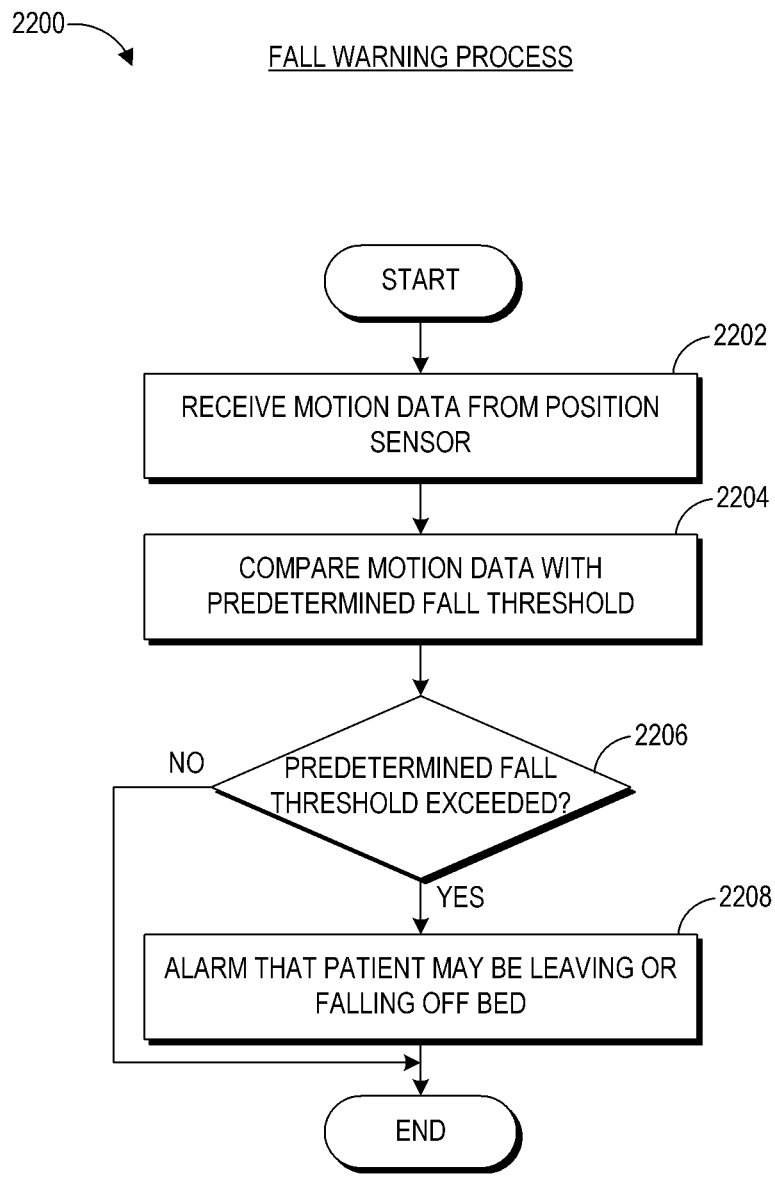
FIG. 22 depicts an embodiment of another fall warning process.

FIG. 22 depicts an embodiment of a fall warning process 2200, which may be implemented by the fall warning module 1912 or any other patient monitoring system.

At block 2202, the fall warning module 1912 receives motion data from a position sensor, such as a gyroscope. The motion data can be indicative of an orientation or a rotation of the patient while the patient is in the bed.

At block 2204, the fall warning module 1912 compares the motion data with a predetermined fall threshold indicative of a degree or significance of motion or rotation of the patient. In one example, the predetermined fall threshold can be a degree of rotation, such as 30°, 60°, 90°, 120°, 150°, or 180° (or some other value) of sideways rotation, by the patient while the patient's body remains parallel to the surface of the bed.

In response to the fall warning module 1912 determining at block 2206 that the predetermined fall threshold is not exceeded by the motion data, the process 2200 may end. For instance, if the motion data indicates that the patient rotated sideways by 20°, the fall warning module 1912 can determine that the 20° of sideways rotation does not exceed a predetermined fall threshold of (for example) 90° of sideways rotation, so the process 2200 ends.

On the other hand, in response to the fall warning module 1912 determining at block 2206 that the predetermined fall threshold is exceeded by the motion data, the fall warning module 1912 at block 2208 can trigger an alarm that the patient may leave the bed, may have left the bed, may have fallen, or is falling. In one example, if the motion data indicates that the patient rotated sideways by 100°, the fall warning module 1912 can determine that the 100° of sideways rotation exceeds the predetermined fall threshold of (e.g.) 90° of sideways rotation, so the fall warning module 1912 triggers the alarm. The alarm can, in some cases, be considered an early fall warning alarm that indicates a greater risk that the patient may subsequently leave the bed in an unsafe manner. Thereafter, the process 2200 may end.

The process 2200 may be modified to so that before an alarm is triggered at block 2208, the fall warning module 1912 also performs one or more additional checks before triggering the alarm. The fall warning module 1912 can, for instance, determine whether a significant drop or change in the thermal profile has occurred as described with respect to block 2008 of the process 2000, before triggering the alarm. Such one or more additional checks can advantageously, in certain embodiments, provide greater confidence that an alarm is triggered under conditions that may require or soon require the attention of a caregiver, and thereby reduce a number of false alarms. Moreover, in some instances, certain rolling motions (for example, a partial sideways roll) followed by leaving the bed can be more likely to indicate of a dangerous situation for the patient than other motions by the patient before the patient leaves the bed. Accordingly, the ability to detect such rolling motions followed by detecting leaving the bed can desirably enable caregivers to treat an alarm triggered under such conditions with an elevated priority because the alarm may likely reflect a greater need for urgent attention or for significant attention or resources to attend to the patient relative to one or more other conditions or alarms. In addition, the fall warning module 1912 may take into account how fast the motion data is changing in order to trigger an alarm. If the motion data changes quickly, or has a high rate of change, this may indicate that the patient is now falling or has fallen.

IV. Additional Embodiments

In certain embodiments, a method of triggering a medical monitoring alarm can include, under control of a hardware processor comprising digital logic circuitry: receiving, from a position sensor, movement data indicative of an orientation or rotation of a patient occupying a patient bed; receiving, from a thermal imaging camera, a baseline thermal image of the patient bed with the patient occupying the patient bed; receiving a second thermal image of the patient bed from the thermal imaging camera; determining whether a portion of the patient to which the position sensor is attached rotated sideways more than a threshold amount in the patient bed based at least on the movement data; determining a degree of change in thermal data between the second thermal image and the baseline thermal image; and triggering an alarm responsive to determining that the patient rotated sideways more than the threshold amount and the determined degree of change in the thermal data.

In certain embodiments, determining the degree of any change includes determining whether a temperature value of the thermal data has decreased to or below a threshold. The alarm can include a fall warning alarm indicating that the patient is at fall risk or has fallen. The alarm can include a fall warning alarm indicating that the patient has left the patient bed. Determining the degree of change can include determining whether the degree of change in the thermal data has not met or exceeded a threshold. The alarm can include a bedsore warning alarm. The position sensor can be an accelerometer, gyroscope, or compass.

V. Terminology

Many other variations than those described herein will be apparent from this disclosure. For example, depending on the embodiment, certain acts, events, or functions of any of the algorithms described herein can be performed in a different sequence, can be added, merged, or left out altogether (e.g., not all described acts or events are necessary for the practice of the algorithms). Moreover, in certain embodiments, acts or events can be performed concurrently, e.g., through multi-threaded processing, interrupt processing, or multiple processors or processor cores or on other parallel architectures, rather than sequentially. In addition, different tasks or processes can be performed by different machines and/or computing systems that can function together.

The various illustrative logical blocks, modules, and algorithm steps described in connection with the embodiments disclosed herein can be implemented as electronic hardware, computer software, or combinations of both. To clearly illustrate this interchangeability of hardware and software, various illustrative components, blocks, modules, and steps have been described above generally in terms of their functionality. Whether such functionality is implemented as hardware or software depends upon the particular application and design constraints imposed on the overall system. The described functionality can be implemented in varying ways for each particular application, but such implementation decisions should not be interpreted as causing a departure from the scope of the disclosure.

The various illustrative logical blocks and modules described in connection with the embodiments disclosed herein can be implemented or performed by a machine, such as a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be a controller, microcontroller, or state machine, combinations of the same, or the like. A processor can include electrical circuitry configured to process computer-executable instructions. In another embodiment, a processor includes an FPGA or other programmable device that performs logic operations without processing computer-executable instructions. A processor can also be implemented as a combination of computing devices, e.g., a combination of a DSP and a microprocessor, a plurality of microprocessors, one or more microprocessors in conjunction with a DSP core, or any other such configuration. A computing environment can include any type of computer system, including, but not limited to, a computer system based on a microprocessor, a mainframe computer, a digital signal processor, a portable computing device, a device controller, or a computational engine within an appliance, to name a few.

The steps of a method, process, or algorithm described in connection with the embodiments disclosed herein can be embodied directly in hardware, in a software module stored in one or more memory devices and executed by one or more processors, or in a combination of the two. A software module can reside in RAM memory, flash memory, ROM memory, EPROM memory, EEPROM memory, registers, hard disk, a removable disk, a CD-ROM, or any other form of non-transitory computer-readable storage medium, media, or physical computer storage known in the art. An example storage medium can be coupled to the processor such that the processor can read information from, and write information to, the storage medium. In the alternative, the storage medium can be integral to the processor. The storage medium can be volatile or nonvolatile. The processor and the storage medium can reside in an ASIC.

Conditional language used herein, such as, among others, "can," "might," "may," "e.g.," and the like, unless specifically stated otherwise, or otherwise understood within the context as used, is generally intended to convey that certain embodiments include, while other embodiments do not include, certain features, elements and/or states. Thus, such conditional language is not generally intended to imply that features, elements and/or states are in any way required for one or more embodiments or that one or more embodiments necessarily include logic for deciding, with or without author input or prompting, whether these features, elements and/or states are included or are to be performed in any particular embodiment. The terms "comprising," "including," "having," and the like are synonymous and are used inclusively, in an open-ended fashion, and do not exclude additional elements, features, acts, operations, and so forth. Also, the term "or" is used in its inclusive sense (and not in its exclusive sense) so that when used, for example, to connect a list of elements, the term "or" means one, some, or all of the elements in the list. Further, the term "each," as used herein, in addition to having its ordinary meaning, can mean any subset of a set of elements to which the term "each" is applied.

While the above detailed description has shown, described, and pointed out novel features as applied to various embodiments, it will be understood that various omissions, substitutions, and changes in the form and details of the devices or algorithms illustrated can be made without departing from the spirit of the disclosure. As will be recognized, certain embodiments of the inventions described herein can be embodied within a form that does not provide all of the features and benefits set forth herein, as some features can be used or practiced separately from others.

What is claimed is:

1. A system for triggering a medical bedsore warning alarm, the system comprising:
   a wireless monitor configured to couple to an armband attached to a patient occupying a patient bed, the wireless monitor configured to receive physiological information from a physiological sensor coupled with the patient and to wirelessly transmit physiological data reflective of the physiological information to a bedside monitor;
   a removable battery that powers the wireless monitor, the removable battery configured to connect with the wireless monitor and configured to be removed from the wireless monitor and then docked with the bedside monitor in order to recharge;
   a wireless position sensor disposed in the wireless monitor or in the armband such that the wireless position sensor is configured to be coupled with the patient; and
   a patient movement detector comprising one or more hardware processors configured to:
      wirelessly receive, from the wireless position sensor, movement data indicative of movement or lack of movement of the patient during a period of time, wherein the wireless position sensor includes at least one of:
   an accelerometer, a gyroscope, or a compass;
      update the movement data to produce updated movement data based on triangulation data received from a plurality of wireless access points;
      determine, based at least in part on the updated movement data, that a portion of the patient has not moved or has moved less than a threshold amount during the period of time;
      receive, from an optical-based sensor, a baseline optical-based profile of the patient;
      receive additional optical-based profiles of the patient from the optical-based sensor, wherein the additional optical-based profiles are captured during the period of time;
      determine whether a degree of change in profile data between the additional optical-based profiles and the baseline optical-based profile has not met or exceeded a threshold degree of change; and
      transmit, over a network, an indication of a bedsore warning alarm, wherein said transmitting is responsive to a combination of both of the following: determining that the degree of change in the profile data has not met or exceeded the threshold degree of change, and determining that the portion of the patient has not moved or has moved less than a threshold amount during the period of time based at least in part on the updated movement data received from the wireless position sensor.

2. The system of claim 1, wherein the patient movement detector is further configured to:
   determine, based at least in part on the updated movement data, a confidence that the patient has not moved or has moved less than a threshold amount during the period of time.

3. The system of claim 1, wherein the indication of the bedsore warning alarm is transmitted, over the network, to a remotely located caregiver for notification.

* * * * *